US011077138B2

(12) United States Patent
Kang

(10) Patent No.: US 11,077,138 B2
(45) Date of Patent: Aug. 3, 2021

(54) METHODS OF TISSUE REPAIR AND REGENERATION

(71) Applicant: INNOLIFE CO., LTD., Sichuan (CN)

(72) Inventor: Yujian James Kang, Sichuan (CN)

(73) Assignee: INNOLIFE CO., LTD., Sichuan (CN)

( * ) Notice: Subject to any disclaimer, the term of this patent is extended or adjusted under 35 U.S.C. 154(b) by 345 days.

(21) Appl. No.: 15/568,386

(22) PCT Filed: Apr. 8, 2016

(86) PCT No.: PCT/CN2016/078873
§ 371 (c)(1),
(2) Date: Oct. 20, 2017

(87) PCT Pub. No.: WO2016/169416
PCT Pub. Date: Oct. 27, 2016

(65) Prior Publication Data
US 2018/0099008 A1  Apr. 12, 2018

(30) Foreign Application Priority Data

Apr. 22, 2015 (WO) ............... PCT/CN2015/077136

(51) Int. Cl.
| A61K 33/34 | (2006.01) |
| A61K 33/30 | (2006.01) |
| A61K 9/00 | (2006.01) |
| A61K 9/50 | (2006.01) |
| A61K 33/04 | (2006.01) |
| A61K 33/26 | (2006.01) |
| A61K 35/12 | (2015.01) |

(52) U.S. Cl.
CPC ............ *A61K 33/34* (2013.01); *A61K 9/0009* (2013.01); *A61K 9/0019* (2013.01); *A61K 9/5052* (2013.01); *A61K 33/04* (2013.01); *A61K 33/26* (2013.01); *A61K 33/30* (2013.01); *A61K 35/12* (2013.01)

(58) Field of Classification Search
CPC ...... A61K 33/34; A61K 9/0019; A61K 33/26; A61K 33/30
See application file for complete search history.

(56) References Cited

U.S. PATENT DOCUMENTS

| 5,190,766 A | 3/1993 | Ishihara |
| 5,558,082 A | 9/1996 | Spencer |
| 5,580,575 A | 12/1996 | Unger |
| 6,896,659 B2 | 5/2005 | Conston |
| 2006/0100278 A1* | 5/2006 | Cooper ............... A61P 9/06 514/554 |
| 2007/0048387 A1 | 3/2007 | Edwards |
| 2008/0311165 A1 | 12/2008 | Gabbay |
| 2011/0014261 A1 | 1/2011 | Day |
| 2011/0165217 A1 | 7/2011 | Jung |
| 2014/0308745 A1 | 10/2014 | Sadiq |
| 2015/0064164 A1 | 3/2015 | Edwards |
| 2018/0296598 A1 | 10/2018 | Kang |

FOREIGN PATENT DOCUMENTS

| CN | 1688301 A | 10/2005 |
| CN | 101926821 A | 12/2010 |
| CN | 102302507 A | 1/2012 |
| CN | 103467578 A | 12/2013 |
| CN | 103502218 A | 1/2014 |
| CN | 102302507 B | 2/2014 |
| CN | 104582711 A | 4/2015 |
| CN | 105753719 A | 7/2016 |
| EP | 0888054 B1 | 9/2003 |
| JP | 2004-533299 A | 11/2004 |
| JP | 2012-100662 A | 5/2012 |
| JP | 2012-533352 A | 5/2015 |
| WO | WO200032225 A1 | 6/2000 |
| WO | WO-2002/100383 A1 | 12/2002 |
| WO | WO2004017956 A1 | 3/2004 |
| WO | WO-2011/008777 A1 | 1/2011 |
| WO | WO2012006938 A1 | 1/2012 |
| WO | WO2012121973 A1 | 9/2012 |
| WO | WO2014035465 A1 | 3/2014 |
| WO | WO2014132262 A1 | 9/2014 |
| WO | WO-2016/169416 A1 | 10/2016 |

(Continued)

OTHER PUBLICATIONS

Gould et al. "Chronic Wound Repair and Healing in Older Adults: Current Status and Future Research", Mar. 2015, J Am Geriatr Soc. vol. 63(3): 427-438. (Year: 2015).*
Unger et al. "Local Drug and Gene Delivery Through Microbubbles", 2001, Prog Cardiovascular Dis, vol. 44(1): 45-54. (Year: 2001).*
Burghardt et al. "A dual function of copper in designing regenerative implants" (2015), Biomaterials, vol. 44: 35-44. (Year: 2015).*
Glantzounis et al. The Contemporary Role of Antioxidant Therapy in Attenuating Liver Ischemia-Reperfusion Injury: A Review, (2005), Liver Transpl vol. 11, No. 9: 1031-47. (Year: 2005).*
Huuskonen et al. "The Copper bis(thiosemicarbazone) Complex Cu (astm) is Protective Against Cerebral Ischemia through Modulation of the Inflammatory Milieu" (2017), Neurotherapeutics, vol. 14: 519-532. (Year: 2017).*

(Continued)

*Primary Examiner* — Teresa E Knight
(74) *Attorney, Agent, or Firm* — Morrison & Foerster LLP; Yuying You

(57) ABSTRACT

The disclosure provides local delivery of a trace element to a site of tissue injury, which triggers the body' inherent tissue repair mechanism. Local delivery of copper to the site of injury induces migration (i.e., homing) of stem cells to the site of injury, triggers differentiation of stem cells at the site of injury, induces tissue regeneration at the site of injury, induces signaling molecules that trigger tissue regeneration, reverses damage at the site of injury, and/or reconstructs the microenvironment of neurofibril cells and neurosecretory cells at the site of injury. In another aspect, delivering a trace element (for example, copper) directly to the site of injury and associated methods are disclosed.

22 Claims, 41 Drawing Sheets

Specification includes a Sequence Listing.

(56) References Cited

FOREIGN PATENT DOCUMENTS

| WO | WO2016168993 A1 | 10/2016 |
|---|---|---|
| WO | WO2017050271 A1 | 3/2017 |

OTHER PUBLICATIONS

Mourino et al. "Metallic ions as therapeutic agents in tissue engineering scaffolds: an overview of their biological applications and strategies for new developments" (2012), J Royal Soc Interface, vol. 9: 401-419 (Year: 2012).*

Cai, Z. et al. (Feb. 1, 2008, e-pub. Oct. 11, 2007). "Complete Loss of Ischaemic Preconditioning-Induced Cardioprotection in Mice With Partial Deficiency Of HIF-1 Alpha," Cardiovasc. Res. 77(3):463-470.

Ceradini, D.J. et al. (Aug. 2004, e-pub. Jul. 4, 2004). "Progenitor Cell Trafficking is Regulated by Hypoxic Gradients Through HIF-1 Induction of SDF-1," Nat. Med. 10(8):858-864.

Ceradini, D.J. et al. (Feb. 2005). "Homing To Hypoxia: HIF-1 As A Mediator of Progenitor Cell Recruitment To Injured Tissue," Trends Cardiovasc. Med. 15(2):57-63.

Chevion, M. et al. (Feb. 1, 1993). "Copper And Iron Are Mobilized Following Myocardial Ischemia: Possible Predictive Criteria For Tissue Injury," Proc. Natl. Acad. Sci. U.S.A. 90(3)1102-1106.

Dimarino, A.M. et al. (Sep. 4, 2013). "Mesenchymal Stem Cells in Tissue Repair.", Frontiers In Immunology 4:1-9.

Dyson, A. et al. (Mar. 23, 2007). "Tissue Oxygen Monitoring in Rodent Models of Shock," Am. J. Physiol. Heart Circ. Physiol. 293:H526-H533.

Essop, M.F. (2007) "Cardiac Metabolic Adaptations In Response To Chronic Hypoxia," J. Physiol. 584:715-726.

European Extended Search Report dated Nov. 9, 2018 for EP Application No. 16782563.7 filed on Apr. 8, 2016, 8 pages.

Feng, W. et al. (2009). "Copper Regulation of Hypoxia-Inducible Factor-1 Activity," Molecular Pharmacology 75(1):174-182.

Friedewald, V.E. et al. (Sep. 15, 2012, e-pub. Jul. 19, 2012). "The Editor's Roundtable: Advances In Stem Cell Therapy For Treatment of Cardiovascular Disease," Am J Cardiol. 110(6):807-816.

Garrett, W.E. et al. (Sep. 1984). "Recovery of Skeletal Muscle After Laceration and Repair," J. Hand Surg. Am. 9A(5):683-692.

Giavaresi, G. et al. (2005, e-pub. Oct. 6, 2004). "Blood Vessel Formation After Soft-Tissue Implantation of Hyaluronanbased Hydrogel Supplemented with Copper Ions," Biomaterials 26:3001-3008.

Greco, V. et al. (Feb. 6, 2009). "A Two-Step Mechanism For Stem Cell Activation During Hair Regeneration," Cell Stem Cell 4(2):155-169.

Han, P. et al. (Apr. 1, 2015). "Improved Recovery After Myocardial Ischemic Infarction by Copper Supplementation," Experimental Biology Meeting 2015, Boston, MA, Mar. 28-Apr. 1, 2015, from BIOSIS/2017 Clarivate Analytics, The FASEB Journal 29, Abstract No. 630.5, 2 pages.

Haubner, B.J. et al. (Dec. 2012). "Complete Cardiac Regeneration In A Mouse Model Of Myocardial Infarction," Aging (Albany NY) 4(12):966-977.

Huang, L.E. et al. (Jul. 1998). "Regulation of Hypoxia-Inducible Factor 1α Is Mediated by an O2-Dependent Degradation Domain Via the Ubiquitin-Proteasome Pathway," Proc. Natl. Acad. Sci. USA 95:7987-7992.

International Search Report and Written Opinion of the International Searching Authority for PCT Application No. PCT/CN2015/077136 dated Jan. 25, 2016 filed Apr. 22, 2015, 9 pages.

International Search Report and Written Opinion of the International Searching Authority for PCT Application No. PCT/CN2016/078873 dated Jun. 22, 2016 filed Apr. 8, 2016, 12 pages.

Ivan, M. et al. (Apr. 20, 2001, e-pub. Mar. 22, 2001). "Hifα Targeted For VHL-Mediated Destruction By Proline Hydroxylation: Implications For O2 Sensing," Science 292(5516):464-468.

Jaakkola, P. et al. (Apr. 20, 2001, e-pub. Apr. 5, 2001). "Targeting of HIF-α to the Von Hippel-Lindau Ubiquitylation Complex By O2-Regulated Prolyl Hydroxylation," Science 292:468-472.

Jiang, Y. et al. (Mar. 19, 2007, e-pub. Mar. 5, 2007). "Dietary Copper Supplementation Reverses Hypertrophic Cardiomyopathy Induced by Chronic Pressure Overload in Mice," J. Exp. Med. 204(3):657-666.

Kajstura, J. et al. (Oct. 9, 2012, e-pub. Sep. 6, 2012). "Cardiomyogenesis in the Aging and Failing Human Heart," Circulation 126(15):1869-1881 (Retracted, Apr. 2014).

Kang, Y.J. et al. (Dec. 2, 2013). "Rejuvenation: An Integrated Approach to Regenerative Medicine," Regen. Med. Res. 1(7):1-8.

Kikuchi, K. et al. (2012). "Cardiac Regenerative Capacity and Mechanisms," Annu. Rev. Cell Dev. Biol. 28:719-741, 27 pages.

Kim, J.W. et al. (Mar. 2006). "HIF-1-Mediated Expression of Pyruvate Dehydrogenase Kinase: A Metabolic Switch Required for Cellular Adaptation to Hypoxia," Cell Metab. 3:177-185.

Lee, S.H. et al. (Mar. 2, 2000). "Early Expression of Angiogenesis Factors in Acute Myocardial Ischemia and Infarction," N. Engl. J. Med. 342(9):626-633.

Li, D. et al. (Jul. 1999) "Liver Fibrogenesis and the Role of Hepatic Stellate Cells: New Insights and Prospects for Therapy," Gastroenterol. Hepatol. 14:618-633.

Li, Q-F. et al. (Jan. 2014). "Copper Promotion of Angiogenesis in Isolated Rat Aortic Ring: Role of Vascular Endothelial Growth Factor," Journal of Nutritional Biochemistry 25:44-49.

Li, S. et al. (Jan. 1, 2012). "Copper Stimulates Growth of Human Umbilical Vein Endothelial Cells in a Vascular Endothelial Growth Factor-Independent Pathway," Experimental Biology and Medicine 237(1):77-82.

Lin, S.L. et al. (Mar. 2, 2010, e-pub. Feb. 16, 2010). "Macrophage Wnt7b is Critical for Kidney Repair and Regeneration," Proc. Natl. Acad. Sci. USA 107(9):4194-4199.

Masson, N. et al. (Sep. 17, 2001). "Independent Function of Two Destruction Domains in Hypoxia-Inducible Factor-α Chains Activated by Prolyl Hydroxylation," EMBO J. 20(18):5197-5206.

Maxwell, P.H. et al., (May 20, 1999) "The Tumour Suppressor Protein VHL Targets Hypoxia-Inducible Factors for Oxygen-Dependent Proteolysis," Nature 399:271-275.

Meng, L. et al. (Oct. 20, 2015). "Recovery of Mesenchymal Stem Cells Homing to Rabbit Myocardial Ischemic Infarct Area by Cu-Microbubble Treatment," Abstract No. GW26-e5347, Journal of The American College of Cardiology 66(16)(Supp. S):C76.

Mirastschijski, U. et al. (2013, e-pub. Apr. 18, 2013). "Zinc, Copper, and Selenium Tissue Levels and Their Relation to Subcutaneous Abscess, Minor Surgery, and Wound Healing in Humans," Biological Trace Element Research 153(1-3):76-83.

Moslehi, J. et al. (Sep. 7, 2010, e-pub. Aug. 23, 2010). "Loss of Hypoxia-Inducible Factor Prolyl Hydroxylase Activity in Cardiomyocytes Phenocopies Ischemic Cardiomyopathy," Circulation 122(10)1004-1016.

Nurchi, V.M. et al. (2013). "Complex Formation Equilibria of CuII and ZnII With Triethylenetetramine and its Mono-and Di-Acetyl Metabolites," Dalton Trans. 42:6161-6170.

Ohh, M et al., (Jul. 2000). "Ubiquitination of Hypoxia-Inducible Factor Requires Direct Binding to the β-Domain of the Von Hippel-Lindau Protein," Nat Cell Biol. 2:423-427.

Okuyama, H. et al. (Jun. 2, 2006). "Expression of Vascular Endothelial Growth Factor Receptor 1 in Bone Marrow-Derived Mesenchymal Cells is Dependent on Hypoxia-Inducible Factor 1," The Journal of Biological Chemistry 281(22):15554-15563.

Porrello, E.R. et al. (Feb. 25, 2011). "Transient Regenerative Potential of the Neonatal Mouse Heart," Science 331(6020):1078-1080.

Qiu, L. et al., (Aug. 2012). "Copper is Required for Cobalt-Induced Transcriptional Activity of Hypoxia-Inducible Factor-1," J. Pharmacol. Exp. Ther. 342(2):561-567.

Rey, S. et al. (May 1, 2010, e-pub. Feb. 17, 2010). "Hypoxia-Inducible Factor-1-Dependent Mechanisms of Vascularization and Vascular Remodeling," Cardiovasc. Res. 86:236-242.

Rodriguez, J.P. et al. (Dec. 31, 2002). "Modulation of the Proliferation and Differentiation of Human Mesenchymal Stem Cells by Copper," Journal of Cellular Biochemistry 85(1):92-100.

(56) References Cited

OTHER PUBLICATIONS

Sadeh, M. (Oct. 1988). "Effects of Aging on Skeletal Muscle Regeneration," J. Neurol. Sci. 87(1):67-74.

Sarkar, D. et al. (Nov. 2008, e-pub. Oct. 31, 2008). "Chemical Engineering of Mesenchymal Stem Cells to Induce a Cell Rolling Response," Bioconjugate Chemistry 19:2105-2109.

Shohet, R.V. et al. (Dec. 2007). "Keeping the Engine Primed: HIF Factors as Key Regulators of Cardiac Metabolism and Angiogenesis During Ischemia," J. Mol. Med 85(12):1309-1315.

Simşek, A. et al. (2006). "Is There a Correlation Between Severity of Trauma and Serum Trace Element Levels?" Acta Orthopaedica et Traumatologica Turcica 40(2):140-143. (English Translation of the Abstract).

Sun, X. et al. (Dec. 31, 2009). "The Role of Hypoxia-Inducible Factor in Osteogenesis and Chondrogenesis," Cytotherapy 11(3):261-267.

Tanimoto, K. et al. (Aug. 15, 2000). "Mechanism of Regulation of the Hypoxia-Inducible Factor-1α by the Von Hippel-Lindau Tumor Suppressor Protein," EMBO J. 19(16):4298-4309.

Tongxian, S. et al. (Mar. 2000). "Change and influence of Content of Zinc and Copper in Acute Myocardial Ischemic," Journal of Luoyang Medical College 18(1):15-17. (English Translation of the Abstract).

Wang, G.L. et al. (Jun. 1995). "Hypoxia-Inducible Factor 1 is a Basic-Helix-Loop-Helix-PAS Heterodimer Regulated by Cellular O2 Tension," Proc Natl. Acad. Sci. USA 92(12):5510-5514.

Wang, G.L. et al. (May 1993). "General Involvement of Hypoxia-Inducible Factor 1 in Transcriptional Response To Hypoxia," Proc. Natl. Acad. Sci. USA. 90(9):4304-4308.

Wilensky, R.L. et al. (Sep.-Oct. 1993). "Methods and Devices for Local Drug Delivery in Coronary and Peripheral Arteries," Trends Cardiovasc.. Med. 3(5):163-170.

Xie, H. et al. (2009). "Role of Copper in Angiogenesis and its Medicinal Implications," Curr. Med. Chem. 16(10):1304-1314.

Zhang, L. et al. (Dec. 31, 2013). "Protection of the Heart by Treatment with a Divalent-Copper-Selective Chelator Reveals a Novel Mechanism Underlying Cardiomyopathy in Diabetic Rats," Cardiovascular Diabetology 12(123):1-17.

Zheng, L. et al. (Apr. 1, 2015). "Recovery of Mesenchymal Stem Cells Homing to Rabbit Myocardial Ischemic Infarct Area by Cu-Microbubble Treatment," Experimental Biology Meeting 2015, Boston, MA, Mar. 28-Apr. 1, 2015, FASEB Journal 29(Supplement 1), Abstract No. 6703, 1 page.

Zheng, L. et al. (Apr. 2015, e-pub. Dec. 1, 2014). "Role of Copper In Regression of Cardiac Hypertrophy," Pharmacol. Ther. 148:66-84.

Zhou, Y. et al. (Jul. 2008, e-pub. Apr. 9, 2008). "Copper Reverses Cardiomyocyte Hypertrophy Through Vascular Endothelial Growth Factor-Mediated Reduction in the Cell Size," J. Mol. Cell Cardiol. 45(1):106-117, 18 pages.

\* cited by examiner

METHODS OF TISSUE REPAIR AND REGENERATION

CROSS REFERENCE TO RELATED APPLICATIONS

This application is a U.S. national phase application under 35 U.S.C. § 371 of PCT International Application No. PCT/CN2016/078873, filed Apr. 8, 2016, which claims priority benefit of International Application No. PCT/CN2015/077136, filed Apr. 22, 2015, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 739962000100SEQLIST.txt, date recorded: Oct. 16, 2017, size: 2 KB).

TECHNICAL FIELD

The present invention relates to methods of tissue repair and regeneration through delivery of trace elements such as copper.

BACKGROUND

Regenerative medicine is an important therapeutic approach involving the process of creating living, functional tissues to repair or replace tissue or organ function lost due to aging, disease, damage, or congenital defects. The biological system is equipped with a self-repair mechanism which is embodied via tissue injury signaling system to ensure that rescue takes place when an injury occurs in an organ in the body. When a tissue is injured, there are different kinds of signals, such as chemokine and cytokine signaling which is instantly initiated from the injury site for communicating the injury with the body's inherent repair mechanism. This communication is mediated by a series of transduction systems, such as the vascular transportation system. Once the injury signal is sensed by the repair mechanism, repairing materials involving stem cells, cytokines, growth factors, and/or chemokines are mobilized and then navigated to the injury site. Thus, the well-maintained vascular and/or lymph transportation systems not only ensure the communication between the injury site and the repair mechanism, but also serve as the essential conduit for the delivery of the repair materials to the injured site. The extent of the tissue injury and the amount of homing factors released to the circulation act as navigators for the transportation of repair materials. After homing to the injury site, stem cells or progenitor cells will differentiate into "target" cells. Multiple regulators, cytokines, growth factors, and chemokines activated by the repair mechanism create a friendly environment to facilitate cell differentiation, tissue regeneration and integration of regenerated tissue with the existing tissue. Therefore, these series of signal transductions and self-repair or self-renewal mechanism as termed are the "tissue injury signaling system." See, e.g., Kang et al., 2013, Regen Med Res, 1, 7. This system requires a well-connected network, and damage to any of the signal generation, signal transduction, signal reception, repairing materials recruitment, injury-directed transportation, homing, differentiation and regeneration processes would result in suppression of self-repair of the injured organ. See, e.g., Kang et al., 2013, Regen Med Res, 1, 7. Some organs (such as liver, bone, skeletal muscle, and pancreas) show a strong capability of self-regeneration when injured. However, during aging and under chronic injury conditions, the self-repairing capacity is diminished due to the dysfunction of tissue injury signaling system.

Myocardial infarction (MI) is a kind of ischemic heart disease (IHD) which results from an imbalance between myocardial oxygen supply and demand due to an inadequate supply of blood. The major causes of MI are atherosclerosis, thrombosis or embolus in the coronary arteries that lead to little perfusion in the region supplied by the culprit vessel. If impaired blood flow to the heart persists, the heart cells in the territory of the occluded coronary artery die, cardiac function is impaired and a collagen scar forms in their place, which puts the patient at risk for potentially life-threatening arrhythmias, and may result in the formation of a ventricular aneurysm that can rupture with catastrophic consequences.

During the contraction of heart, cardiac pump consumes a large amount of energy generated by aerobic metabolism to maintain the circulation, and sufficient blood supply to the cardiac tissues is essential for maintaining cardiac functions. See, e.g., Essop, 2007, J Physiol, 584, 715-726; Dyson et al., 2007, Am J Physiol Heart Circ Physiol, 293, H526-533. Myocardial ischemia is a leading cause of cardiac dysfunction. The detrimental influence from disruption of local coronary artery on myocardium is not only in initiating the ischemia injury to the territory of occluded coronary artery, but also in blocking the way of materials homing to the ischemia area for self-restoration which is motivated by human body's inherent tissue repair mechanism. The solution for promoting the recovery of blood supply is critical in myocardium regeneration.

Under ischemia condition, the initial and primary molecular response to reduction of blood supply is the accumulation of hypoxia inducible factors. Hypoxia-inducible factors (HIF-1, HIF-2 and HIF-3) play key roles in the transcriptional response to hypoxia. HIFs are heterodimers, comprising a unique oxygen-dependent α subunit and a common constitutively expressed β subunit. There are three HIFαs in humans and mammals. Hypoxic signaling plays an essential role in maintaining oxygen homeostasis and cell survival. Hypoxia-inducible transcription factors HIF-1 and HIF-2 are central mediators of the cellular response to hypoxia by regulating the expression of genes controlling metabolic adaptation, oxygen delivery, and survival in response to oxygen deprivation.

HIF-1 transcription factor comprises of HIF-1α and HIF-1β or ARNT (Aryl hydrocarbon nuclear translocator). See, e.g., Wang et al., 1995, PNAS, 92, 5510-5514. The accumulation of HIF-1α is a rate-limiting step for the activation of HIF-1; thus, the major regulation of HIF-1α is at the posttranslational level. See, e.g., Wang et al., 1993, PNAS, 90, 4304-4308; Huang et al., 1998, PNAS, 95, 7987-7992. The expression level of HIF-1α is undetectable in most cell types under normoxic conditions due to its degradation by the ubiquitin-proteasome pathway. In this process, one or both of the two conserved proline residues (Pro402 and Pro564) in HIF-1α are recognized by members of the prolyl hydroxylase domain-containing proteins (PHDs), which catalyze the reaction of proline hydroxylation. See, e.g., Huang et al., 1998, PNAS, 95, 7987-7992; Jaakkola et al., 2001, Science, 292, 468-472; Ivan et al., 2001, Science, 292, 464-468. The hydroxylated HIF-1α is recognized by a von Hippel-Lindau protein (pVHL), which is a constituent of an ubiquitin ligase complex, targeting HIF-1α subunit for degradation by proteasome in cytosol. See, e.g., Maxwell et al., 1999, Nature, 399, 271-275; Masson et al., 2001, EMBO J, 20, 5197-5206; Ohh et al., 2000, Nat Cell Biol, 2, 423-427; Tanimoto et al., 2000, EMBO J, 19, 4298-4309. Under hypoxic conditions, HIF-1α escapes from the degradation pathway, accumulates, and translocates into nucleus, where it dimerizes with HIF-1β and interacts with cofactors to assemble the HIF-1 transcriptional complex, leading to up-regulation of multiple genes involved in the response to the injury. See, e.g., Shohet et al., 2007, J Mol Med (Berl), 85, 1309-1315; Kim et al., 2006, Cell Metab, 3, 177-185. Among the genes regulated by HIF are those involved in the vasculogenesis, such as vascular endothelial growth factor (VEGF), stem cell factor (SCF), stromal cell-derived factor-1 (SDF-1), vascular endothelial growth factor receptor 1 (VEGFR-1), placental growth factor (PLGF), angiopoietin 1 (ANGPT1) and 2 (ANGPT2), and platelet-derived growth factor B (PDGFB). See, e.g., Rey et al., 2010, Cardiovasc Res, 86, 236-242. Under acute ischemia condition, HIF-1 induced angiogenesis is enhanced significantly. The activation of HIF-1 acts important role in angiogenesis and harmonizes ischemic tissue adaption to hypoxia condition. See, e.g., Lee et al., 2000, N Engl J Med, 342, 626-633.

However, under the chronic ischemic condition, injured myocardium is commonly characterized by decreased capillary density and depressed angiogenesis, rather than enhanced. The defending action as activated by accumulated HIF-1α under the acute ischemia insult does not work even HIF-1α levels increased persistently in ischemic myocardium sampled from patients with chronic ischemic cardiomyopathy. However, the expression of subsequent gene, such as VEGF, was depressed. See, e.g., Lee et al., 2000, N Engl J Med, 342, 626-33; Moslehi et al., 2010, Circulation, 122, 1004-1016.

The disclosures of all publications, patents, and patent applications referred to herein are hereby incorporated herein by reference in their entirety.

BRIEF SUMMARY OF THE INVENTION

The present application in one aspect provides a method of inducing at least two events of tissue repair in an individual having a tissue injury, comprising delivering to the site of injury an effective amount of a trace element. In some embodiments, at least one event of the tissue repair comprises inducing the migration of bone marrow mesenchymal stem cells to the site of injury. In some embodiments, at least one event of the tissue repair comprises inducing differentiation of stem cells at the site of injury. In some embodiments, at least one event of the tissue repair comprises inducing tissue regeneration at the site of injury. In some embodiments, at least one event of the tissue repair comprises inducing a signaling molecule that triggers tissue regeneration. In some embodiments, at least one event of the tissue repair comprises reversing damage at the site of injury. In some embodiments, at least one event of the tissue repair comprises reconstruction of the microenvironment of neurofibril cells and neurosecretory cells at the site of injury. In some embodiments, at least one event of the tissue repair comprises restoring and/or enhancing the injury signal. In some embodiments, at least one event of the tissue repair comprises signal transduction and/or reception of the injury signal. In some embodiments, at least one event of the tissue repair comprises restoring and/or enhancing the recruitment of a repair material to the injury site. In some embodiments, at least one event of the tissue repair comprises restoring and/or enhancing injury-directed transportation and/or homing of a repair material. In some aspects, the repair material comprises a cell such as a stem cell, a cytokine, a growth factor, and/or a chemokine. In some embodiments, at least one event of the tissue repair comprises restoring and/or enhancing differentiation of a stem cell or a progenitor cell and tissue regeneration at the injury site. In some embodiments, the individual is human. In some embodiments, the individual has a compromised tissue repair system.

In another aspect, there is provided a method of inducing migration of stem cells (such as mesenchymal stem cells, for example bone marrow mesenchymal stem cells) to a site of injury in a tissue of an individual having a tissue injury, comprising delivering to the site of injury an effective amount of a trace element. In some embodiments, the individual is human. In some embodiments, the individual has a compromised tissue repair system.

In another aspect, there is provided a method of inducing tissue repair in an individual having a tissue injury, comprising: a) delivering to the site of injury an effective amount of a trace element and b) administering to the individual an effective amount of stem cells (such as mesenchymal stem cells, such as bone marrow mesenchymal stem cells). In some embodiments, the individual is human. In some embodiments, the individual has a compromised tissue repair system.

In another aspect, there is provided a method of inducing tissue repair in an individual having a compromised tissue repair system, comprising delivering to the site of injury an effective amount of a trace element. In some embodiments, the individual is human.

In some embodiments according to any one of the methods described above, wherein the individual has a chronic tissue injury. In some embodiments, the individual is at least 60 years old. In some embodiments, the individual is deficient in bone marrow mesenchymal stem cells.

In some embodiments according to any one of the methods described above, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element.

In some embodiments according to any one of the methods described above, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury.

In some embodiments according to any one of the methods described above, the tissue is heart, liver, brain, lung, kidney, skin, digestive tract, reproductive organs, bone, or skeletal muscle. In some embodiments, the tissue is heart.

The present application in one aspect provides a method of inducing tissue repair in an individual having a tissue injury, comprising delivering an effective amount of a trace element directly to the site of injury. In another aspect, there is provided a method of inducing blood vessel growth towards the site of injury in an individual having a tissue injury, comprising delivering an effective amount of a trace element directly to the site of the injury.

In some embodiments according to any one of the methods described above, the trace element is delivered via injection and stays concentrated at the injection site upon injection (for example injection via a catheter). In some embodiments, the trace element is delivered via an implant containing the trace element (for example an implant coated with the trace element, for example an implant selected from the group consisting of a stent, a place, and a membrane).

In some embodiments according to any one of the methods described above, the method further comprises administering to the individual an effective amount of stem cells. In some embodiments, the method further comprises administering to the individual an effective amount of an inducer of stem cells.

In some embodiment according to any one of the methods described above, the individual has a compromised tissue repair system. In some embodiments, the individual having a compromised tissue repair system is an individual having a chronic tissue injury or an acute tissue injury. In some embodiments, the individual having a compromised tissue repair system is an individual who is at least 60 years old. In some embodiments, the individual having a compromised tissue repair system is an individual who is deficient in stem cells.

In some embodiments according to any one of the methods described above, the trace element is selected from the group consisting of copper, iron, zinc, and selenium. In some embodiments, the trace element is copper. In some embodiments according to any one of the methods described above, the tissue is heart, liver, brain, lung, kidney, skin, digestive tract, reproductive organs, bone, or skeletal muscle. In some embodiments, the tissue is heart.

Also provided are kits and articles of manufacture useful for the methods described herein.

BRIEF DESCRIPTION OF THE FIGURES

FIG. 1A shows decreased cardiac infarction area. FIG. 1B shows decreased cardiac infarction area. FIG. 1C shows improved left ventricular ejection fraction. FIG. 1D shows increased capillary density in infarction area.

FIG. 44A shows effects of varying concentrations of copper on VEGF protein levels. FIG. 44B shows the effect of TEPA on VEGF protein levels.

DETAILED DESCRIPTION OF THE INVENTION

Figure 1:
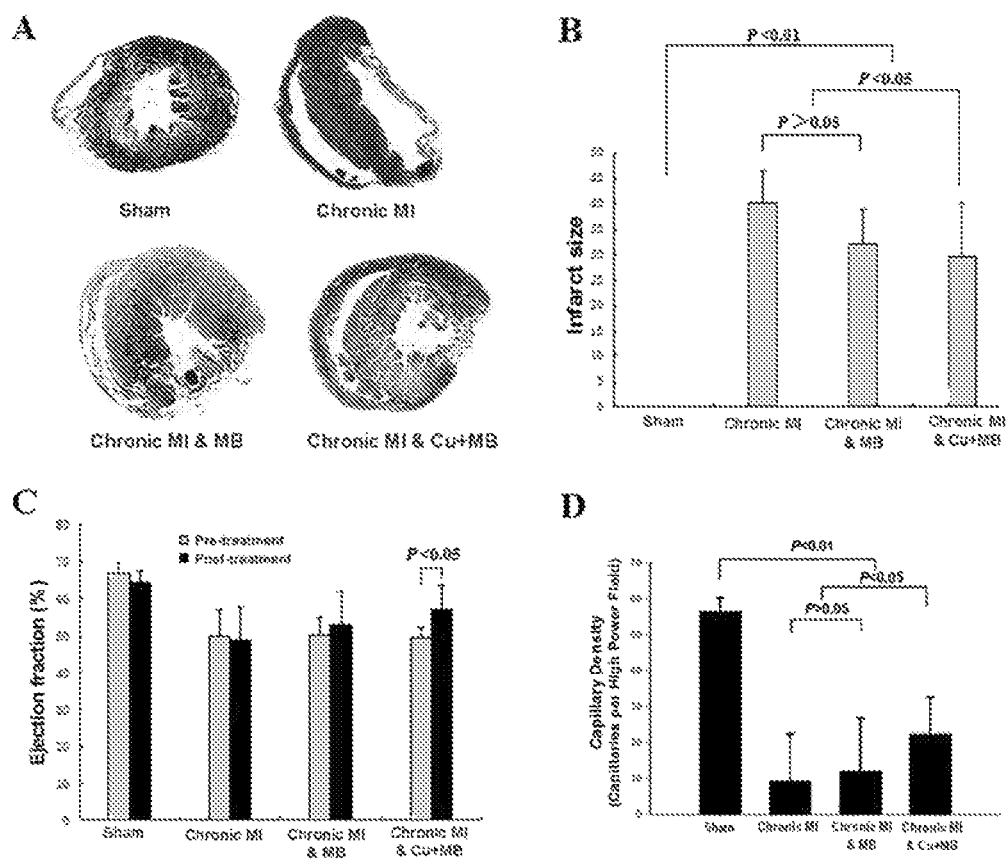
FIGS. 1A-1D show results of Cu-MB treatment of chronic myocardial infarction in the New Zealand rabbit model.

HIF-1 transcriptional activity was previously shown to require the participation of trace element copper. See, e.g., Jiang et al., 2007, J Exp Med, 04, 657-666; Feng et al., 2009, Mol Pharmacol, 75, 174-182; Qiu et al., J Pharmacol 2012, Exp Ther, 342, 561-567. Deprivation of copper from cells reduced HIF-1α binding to the HRE sequence of target genes and to P300, a component of HIF-1 transcriptional complex, and suppressed expression of VEGF and other genes regulated by HIF-1, although the production and stabilization of HIF-1α were not affected. Importantly, the copper concentration was lower in the heart of people who died from chronic heart disease. It was known that copper mobilization depart from myocardium was triggered by ischemia prolongation. See, e.g., Chevion et al., PNAS, 90, 1102-1106. The loss of copper correlated well with the degree of the cardiac dysfunction.

Therefore, the dramatically outpouring of myocardial copper is believed to be the leading cause of the depression of accumulated HIF-1α transcriptional activity accompanied with prolonged myocardial ischemia. Accordingly, even under the condition of HIF-1 protein levels elevation, the up-regulation of the HIF-1 controlled genes did not occur due to the loss of cardiac copper. Delivery of copper to the site of injury effectively is thus expected to restore the HIF-1 transcription activity and actually reverses myocardial ischemic infarction. Trace elements such as copper, when delivered to the site of injury of a tissue to activate the HIF-1 transcription activity, would be particularly effective in inducing tissue repair and self-regeneration.

Thus, the present application in one aspect provides a method of inducing at least two events of tissue repair in an individual having a tissue injury, comprising delivering to the site of injury an effective amount of a trace element. This is based on inventors' insight that delivery of a trace element such as copper to a site of tissue injury triggers the body's inherent tissue repair mechanism, composed of a series of events that lead to tissue repair. It is believed that local delivery of copper to the site of injury via microbubbles would induce migration (i.e., homing) of bone marrow mesenchymal stem cells (BMSC) to the site of injury, even after the tissue in the individual has otherwise lost the inherent ability to spontaneously recruit BMSC cells. Local delivery of copper to the site of injury would also trigger a series of other events leading to tissue repair, including for example inducing differentiation of stem cells at the site of injury, inducing a signaling molecule that triggers tissue regeneration, inducing tissue regeneration at the site of injury, reversing damage at the site of injury, and reconstructing the microenvironment of neurofibril cells and neurosecretory cells at the site of injury. It is believed that copper and other trace elements have a central role in tissue repair, and the present disclosure opens up new therapeutic opportunities for effective treatment of diseases involving tissue damage.

In another aspect, the present invention provides methods of inducing tissue repair in an individual having a tissue injury, comprising delivering an effective amount of a trace element directly into the site of injury. This is based on inventor's insight that trace elements such as copper, when delivered directly to the site of injury of a tissue, are particularly effective in inducing tissue repair. For example, it is believed that trace elements present at the site of injury can attract the growth of blood vessel towards the site of injury, thus facilitating the regeneration of the blood microvessel environment at the site of injury and consequently regeneration of the tissue. It is further believed that the effect of copper (or other trace elements) on tissue repair and blood vessel formation depend on a specific concentration of copper (or other trace elements) at the local injury site. Direct delivery of copper (or other trace elements) to the injury site may provide better control of the desired copper concentration at the local injury site, thus allowing more precise intervention and treatment.

Accordingly, the present application in some embodiments provides a method of inducing at least two events of tissue repair in an individual having a tissue injury, comprising delivering to the site of injury an effective amount of a trace element.

In some embodiments, there is provided a method of inducing migration of a stem cell (such as a mesenchymal stem cell (MSC), for example a bone marrow mesenchymal cell (BMSC)) to a site of injury in a tissue of an individual having a tissue injury, comprising delivering to the site of injury an effective amount of a trace element.

In some embodiments, there is provided a method of inducing tissue repair in an individual having a tissue injury, comprising delivering to the site of injury an effective amount of a trace element and an effective amount of stem cells (such as MSC, for example BMSC) or an inducer of stem cells (such as MSC, for example BMSC).

In some embodiments, there is provided a method of inducing tissue repair in an individual having a compromised tissue repair system, comprising delivering to the site of injury an effective amount of a trace element.

In some embodiments, there is provided a method of inducing tissue repair in an individual having a tissue injury, comprising delivering an effective amount of a trace element directly into the site of injury.

In some embodiments, there is provided a method of inducing blood vessel growth towards the site of injury in an individual having a tissue injury, comprising delivering an effective amount of a trace element directly to the site of the injury.

Also provided are kits and article of manufactures useful for the methods described herein.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

The term "about X-Y" used herein has the same meaning as "about X to about Y."

As used herein and in the appended claims, the singular forms "a," "or," and "the" include plural referents unless the context clearly dictates otherwise.

As is apparent to one skilled in the art, an individual assessed, selected for, and/or receiving treatment is an individual in need of such activities.

Methods of Inducing One or More Events of Tissue Repair

The present application in one aspect provides a method of inducing at least one (including for example at least any of 2, 3, 4, 5, 6, or more) events of tissue repair in an individual having a tissue injury, comprising delivering to the site of injury an effective amount of a trace element. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element.

An "individual" described herein refers to a mammal such as mice, rats, rabbits, cats, dogs, pigs, cows, ox, sheep, goats, horses, monkeys and other non-human primates, and humans, a vertebrate such as fish, and a bird such as chicken. Mammals can include farm animals, sport animals, rodents, and pets. In some embodiments, the individual is human.

In some embodiments, at least one event of the tissue repair comprises inducing the migration of stem cells to the site of injury, including but not limited to mesenchymal stem cells (MSCs), bone marrow mesenchymal stem cells (BMSCs), multipotent stem cells, induced pluripotent stem cells (iPS), or various tissue-derived stem cells. In some aspects, the tissue-derived stem cell is an adipose tissue-derived stem cell, a cardiac tissue-derived stem cell, or an umbilical cord tissue-derived stem cell. In other embodiments, the stem cell disclosed herein is an adult stem cell. In particular aspects, the adult stem cell is a hematopoietic stem cell, a mammary stem cell, an intestinal stem cell, a mesenchymal stem cell in the placenta, adipose tissue, lung, bone marrow, blood, Wharton's jelly of the umbilical cord, or teeth (such as the perivascular niche of dental pulp and periodontal ligament), an endothelial stem cell, a neural stem cell, an olfactory adult stem cell, a neural crest stem cell, or a germline stem cell (for example, a stem cell in the testicle).

In some embodiments, at least one event of the tissue repair comprises inducing differentiation of stem cells at the site of injury. In some embodiments, at least one event of the tissue repair comprises inducing tissue regeneration at the site of injury. In some embodiments, at least one event of the tissue repair comprises inducing a signaling molecule that triggers tissue regeneration. In some embodiments, at least one event of the tissue repair comprises reversing damage at the site of injury. In some embodiments, at least one event of the tissue repair comprises reconstruction of the microenvironment of neurofibril cells and neurosecretory cells at the site of injury. In some embodiments, the trace element is copper. In some embodiments, the tissue is heart, liver, brain, lung, kidney, skin, digestive tract, reproductive organs, bone, or skeletal muscle. In some embodiments, the tissue is heart.

An individual having a tissue injury described herein include, but re not limited to, individuals having one or more of: myocardial injury, brain injury, spinal cord injury, muscular injury, skeletal injury, acute tubular necrosis, bowel injury, lung injury, liver injury, kidney injury, bone injury, skin injury, hernia repair, vascular anastomoses, atherosclerotic plaque, hemangioma, and after blunt or penetrating traumatic injury.

In some embodiments, there is provided a method of inducing migration (i.e., homing) of stem cells to a site of injury in a tissue of an individual having a tissue injury, comprising delivering to the site of injury an effective amount of a trace element. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element. In some embodiments, the tissue is heart, liver, brain, lung, kidney, skin, digestive tract, reproductive organs, bone, or skeletal muscle. In some embodiments, the tissue is heart.

In some embodiments, the stem cell is a mesenchymal stem cell (MSC), a bone marrow mesenchymal stem cell (BMSC), a multipotent stem cell, an induced pluripotent stem cell (iPS), or a tissue-derived stem cell. In some aspects, the tissue-derived stem cell is an adipose tissue-derived stem cell, a cardiac tissue-derived stem cell, or an umbilical cord tissue-derived stem cell. In other embodiments, the stem cell is an adult stem cell. In particular aspects, the adult stem cell is a hematopoietic stem cell, a mammary stem cell, an intestinal stem cell, a mesenchymal stem cell in the placenta, adipose tissue, lung, bone marrow, blood, Wharton's jelly of the umbilical cord, or teeth (such as the perivascular niche of dental pulp and periodontal ligament), an endothelial stem cell, a neural stem cell, an olfactory adult stem cell, a neural crest stem cell, or a germline stem cell (for example, a stem cell in the testicle).

In some embodiments, the stem cells migrate in vivo from an organ or tissue compartment to a site of injury in another organ or tissue compartment of an individual having a tissue injury. For example, the MSCs can migrate from the bone marrow (BM), umbilical cord blood (UCB), umbilical cord stroma (Wharton's jelly), placenta, and adipose tissue (AT). In other embodiments, MSCs can be isolated from an organ or tissue compartment, enriched and/or treated in vitro, and then used in vivo for migration to the site of tissue or organ injury.

In other embodiments, cell migration assays used herein include biomarkers, bioluminescence, fluorescence, positron emission tomography (PET)/CT, and magnetic resonance imaging (MRI) in vivo. The in vivo assays can be validated and corroborated with other methods, for example, IHC on tissue sections.

In vivo, noninvasive imaging techniques for assaying stem cell migration include imaging gold-dextran coated particles that are loaded into MSCs, which can be visualized using X-ray, Raman spectroscopy, computed tomography (CT), or ultrasound (US) modalities. In some embodiments, biocompatible nanoparticle constructs, tracers, or superparamagnetic particles are loaded into stem cells such as MSCs with properties to enable cell visualization by X-ray, CT, US, PET, or MRI. In some embodiments, migration of stem cells can be assayed using techniques such as cecal ligation and puncture (CLP). For example, performing CLP on a GFP chimeric mouse allows one to observe the behavior of BMSC in the setting of abdominal sepsis. FACS, flow cytometry and immunohistochemistry can be used to track the migration of BMSC into peripheral blood, lung, liver, the cutaneous wound, and the primary site of injury. BMSC behavior can be correlated to time of injury as well as to local (using RT-PCR) and systemic levels of cytokines and chemokines. Tracking migration of the stem cells can help elucidate the contribution of BMSC to local and distant organ and tissue repair and regeneration following a tissue injury.

In some embodiments, the migration of stem cells can be monitored using labeled cells administered to an individual. Approaches such as isotopic labelling and dyeing are used to label stem cells. In some embodiments, the labeling approaches include: injecting stem cells of male animals to the female, so the Y chromosome could be the tracker; injecting stem cells of A species to B species, so the specific genes of A species could be the cell tracker; labeling the stem cells with pKH26, BrdU or other dyes, so the stem cells could be tracked by the dyes or specific enzymatic reactions to the tracker.

The most common approach of tracking in vivo is isotopic labeling. The stem cells could be tracked by the isotopes that label the cells. But it is worth noticing that the safety issues and radioactive half-life has to be considered. Other in vivo tracking approaches of stem cells include: cell dyeing by cell dyes such as DID, live imaging of body surface cells by Two-photon excited fluorescence microscopy, live imaging of specific body surface cells of transgenic animals by Two-photon excited fluorescence microscopy, labeling cells with SPIO and tracking the tracker by MRI, etc. Stem cells could be labeled by multiple fluorescent dyes, and then injected into animals. When reaching to check point, target organs could be frozen sliced and observed directly through confocal laser scanning microscopy. This tracking approach does not take too many labeled cells (10○6 cell/rabbit), so the autologous cells could be used as the tracker in the natural state of the organs and cells.

Labeling of stem cells can be achieved, for example, by one sole tracker like pKH26. pKH26 is a liposoluble dye, the labeling by which does not penetrate the cell membrane, so that fits for the live cell tracking. The tracking process mentioned here is multiple labeling by 2 or 3 dyes. One selected labeling approach is through nucleus tracker (DAPI, Hoechst) plus membrane tracker. Nucleus tracker affirms the nucleus of the cells, and echoes the membrane tracker pKH26 at the same time. Another approach is multiple labeling by 2 membrane trackers, e.g. Dio (3) & pKH26. These trackers label the cells through similar mechanisms, but have different excitation and emission wavelengths. Thus the homing signals include 2 different fluorescent signals, the two of which prove the homing BMSCs simultaneously. In this tracking method, only the overlapped signals of different wavelengths (such as red and green signals) are considered the homing signals.

Many kinds of animal tissues are auto-fluorescent, and the most common auto-fluorescence in natural tissues is green fluorescence. Hearts is relatively less fluorescent, but is fluorescent enough to make interference in the observation. The cut edge of the slices is always the most strongly fluorescent. To cope with the disturbance, only the green and red overlapped signals could be recognized as the tracking signals. Red fluorescence is more suitable for the statistical analysis with IOD value for its specificity (except for obvious inaccuracy in red fluorescent signals).

In some embodiments, there is provided a method of inducing differentiation of stem cells and/or inducing tissue regeneration at the site of injury, comprising delivering to the site of injury an effective amount of a trace element. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element. In some embodiments, the tissue is heart, liver, brain, lung, kidney, skin, digestive tract, reproductive organs, bone, or skeletal muscle. In some embodiments, the tissue is heart. In certain aspects, the stem cell is capable of differentiating into a mesenchymal cell type, including osteoblasts, adipocytes, chondrocytes, endothelial cells, epithelial cells, enterocytes, osteocytes, neurocytes, hepatocytes, nephrocytes, myocytes (skeletal muscle and smooth muscle), and cardiomyocytes. In other aspects, the stem cell is capable of differentiating into cells of nonmesodermal origin including beta cells, hepatocytes, and neurons.

Assays known in the art can be used to elucidate the process of stem cell differentiation and the phenotypes of differentiated stem cells (such as MSCs, for example BMSC), including alkaline phosphatase and alizarin red S staining for osteoblasts, oil red O staining for adipocytes, and alcian blue staining for chondrogenesis. Differentiation of stem cells such as MSCs into various cell types can also be assayed by gene expression profiling. For example, transcription profiling has identified specific genes implicated in osteogenic differentiation (FHL2, ITGA5, Fgf18), chondrogenesis (FOXO1A), and tenogenesis (Smad8). In some embodiments, MSCs can give rise to high cell numbers by large-scale expansion. In some embodiments, there is provided a method of inducing tissue regeneration at the site of injury in an individual, comprising delivering to the site of injury an effective amount of a trace element. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element. In some embodiments, the tissue is heart, liver, brain, lung, kidney, skin, digestive tract, reproductive organs, bone, or skeletal muscle. In some embodiments, the tissue is heart. In some embodiments, the method induces cell proliferation at the site of injury. In some embodiments, the method induces angiogenesis at the site of the injury. In some embodiments, the method induces blood vessel maturation at the site of injury. In some embodiments, the method results in two or more of the effects described above.

Tissue regeneration disclosed herein can be assayed, for example, in an organism in which a portion of a tissue is damaged or removed. A trace element with or without a stem cell as described herein is then administered to the organism and the rate of tissue regeneration is determined. The rate of tissue regeneration can be compared to the rate observed when an organism is administered a control or is not treated. Other parameters that can be determined during a tissue regeneration assay include, but are not limited to, symptoms or outcomes such as pain or makers of pain, signs or symptoms of inflammation, final degree of regeneration, and quality of regeneration. In other embodiments, a tissue regeneration assay herein comprises assessing one or more organ functional parameters, such as one or more heart functional markers, one or more kidney functional markers, and one or more liver functional markers.

In some embodiments, one or more of the following parameters in the analysis of cardiac regeneration and repair can be used for evaluation of the methods described herein: (1) amount of reconstituted tissue or myocardium mass and coronary vasculature; (2) number and size of restored myocytes and vessels; (3) integration of newly formed myocytes and vessels with the surrounding myocardium; and (4) origin of the regenerated myocardial structures. In one aspect, magnetic resonance imaging (MRI) can be performed to study the scar area, the global left ventricular function, the regional function (wall motion and thickening) and regional ventricular perfusion. In another aspect, MRI is used to detect and/or confirm the presence of new vessels, tissue or cells that improve ventricular function. In yet another aspect, histopathology can be performed to determine the scar area and the identification and quantification of c-kit positive cardiac stem cells. Histopathology also provides data on distribution, size and density of new vessels and cardiomyocytes. Histopathology allows documenting the repair process at the tissue and cellular level. For example, tests are performed to evaluate, within the infarct sections, the microvessel density (vWF-positive vessels/$mm^2$), BrdU positive cells and c-kit positive cells. The quantification of microvessel density using von Willebrand factor (vWF) allows determining the amount of new blood vessels created in the infarct zone. BrdU positive cells represent the proliferation of cells, including cardiac cells. C-kit positive cell tests show the amount of stem cells within the selected infarct sections.

In some embodiments, there is provided a method of inducing a signaling molecule that triggers tissue regeneration in a tissue of an individual having a tissue injury, comprising delivering to the site of injury an effective amount of a trace element. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element. In some embodiments, the tissue is heart, liver, brain, lung, kidney, skin, digestive tract, reproductive organs, bone, or skeletal muscle. In some embodiments, the tissue is heart.

Suitable signaling molecules described herein include, but are not limited to, HIF-1, VEGF, SDF-1, CXCR4, CXCL12 (also termed SDF-1α), MMPs, HGF/c-met, TGF-β1, IL-1β, TNF-α, CCR1, CCR4, CCR7, CCR10, CCR9, CXCR5, CXCR6, CD44, CD54, CD56, CD106, E-cadherin, P-selectin, integrins such as integrin-beta1 and CD49a, b, c, e, f (integrins a1, 2, 3, 4, 6), and integrin ligands such as VCAM and ICAM.

SDF-1/CXCR4 axis is one of the most important mechanisms of stem cell homing. SDF-1 (Stromal cell-derived factor 1 or CXCL12), belonging to the CXC-chemokine family, is a kind of small molecular secreted protein. The expression of SDF-1 is regulated by HIF-1 (Hypoxia inducible factor-1). HIF-1 is composed of HIF-1α and HIF-10/ARNT (aryl hydrocarbon nuclear translocator, ARNT). HIF-1β is stable in the cytoplasm, so the expression and accumulation of HIF-1α is determinate for the activity of HIF-1. Under normoxia, HIF-1α protein is synthesized and degraded rapidly by the ubiquitin-proteasome system. Prolyl hydroxylases (PHDs) hydroxylate HIF-1α and hydroxylated HIF-1α is recognized by the von Hippel-Lindau tumor suppressor protein (pVHL), which constitutes an ubiquitin-protein ligase that targets HIF-1α protein degradation. When injured, the harmed region is hypoxic, which inhibits the activity of PHDs, enabling HIF-1α accumulation and translocation into the nucleus, where in dimerizes with HIF-1β to form HIF-1, combine with other factors and initiates the target gene transcription. Injured tissues express and high level of SDF-1 and release it into the circulation, building a concentration gradient from the injured region to the far-end of circulation. The gradient thus attracts CXCR4 expressed stem cells, including BMSCs, to the injured tissues.

When the heart is under chronic hypoxia, the blood that coronary arteries cannot meet the demand of myocardium. So the chronic ischemia would induce the myocardial fibrosis, decrease of micro arteries, harm to the blood pumping, and finally the ischemic cardiac infarction. Under chronic ischemia, the activity of HIF-1 is limited, resulting in the inhibition of the expression of angiogenic factors that are regulated by HIF-1. The blood supply thus could not be rebuilt and the infarction would appear.

Usually, the HIF-1 activity in injured tissues is temporally limited. Both animal experiments and clinical trials have proved that, under cardiac ischemia, HIF-1α in injured tissues accumulates instantly after the injury, but gradually decreases afterward. The activity of HIF-1 drops even faster than the content, causing the drop of the expression of HIF-1 regulated factors, like VEGF and SDF-1, after the transient increase. Due to the regulation of HIF-1, the expression of SDF-1 peaks at the first or second day after cardiac infarction. It then decreases gradually, and reduces to the baseline in about one month. For that SDF-1 is one of the stem cells homing mobilizer, the decrease of SDF-1 leads to the receding and even disappearing of stem cells homing.

Importantly, the defending action induced by HIF-1α as activated under the acute ischemia condition works differently from under prolonged ischemic conditions. Under a long term ischemia condition, HIF protein levels are increased in the ischemic myocardium, whereas, genes regulated by HIF (such as VEGF) are suppressed, which lead to diminished revascularization and impaired regeneration. Copper deprivation reduces HIF-1α binding to the HRE sequence of target genes and to P300, a component of HIF-1 transcriptional complex. Moreover, copper is substantially mobilized from myocardium to blood immediately following prolonged ischemia. This mobilization of copper in the coronary flow sensitively follows prolonged, but not short, cardiac ischemia. The loss of myocardium copper correlates with the degree of the loss of cardiac function. Therefore, even under the condition of elevated HIF protein level, the up-regulation of the HIF controlled genes does not occur due to the loss of myocardium copper. Trace elements such as copper can lead to the activation of HIF-1, including HIF-1α synthesis, stabilization, translocation from cytosol to nucleus, binding to the HRE sequence of target genes, and HIF-1 transcriptional complex formation. The methods described herein are useful for inducing one or more signaling molecules, such as HIF-1α.

In some embodiments, there is provided a method of reversing damage at the site of injury in a tissue of an individual, comprising delivering to the site of injury an effective amount of a trace element. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element. In some embodiments, the tissue is heart, liver, brain, lung, kidney, skin, digestive tract, reproductive organs, bone, or skeletal muscle. In some embodiments, the tissue is heart.

Reversal of tissue damage can be assayed by any suitable method, for example, detection of cellular markers of normal tissue homeostasis and/or of persistent tissue damage (for example, by immunohistochemistry or measuring DNA and transcript levels), measuring the area of damage or volume of damage, or assessing any clinically relevant indicators. For example, reversal of heart tissue damage of infracted tissue can be measured by quantitation of cell number, such as the number of myocytes, fibroblast, or amount of scarring, or with functional assays for output or structural aspects of heart function including, LVEDP, LVDP, max dp/dt, min dp/dt, LV Weight, Chamber Volume, and Diastolic Wall Stress. In general, a method disclosed herein is said to revers damage in the damaged tissue if it results in a significant (e.g., at least 2-fold) change in any such clinical assessment or any combination thereof. In some embodiments, the method reverses fibrosis at the site of injury in the tissue. Fibrosis is the abnormal accumulation of fibrous tissue that can occur as a part of the wound-healing process in damaged tissue. Such tissue damage may result from physical injury, inflammation, infection, exposure to toxins, and other causes. Liver (hepatic) fibrosis, for example, occurs as a part of the wound-healing response to chronic liver injury. Fibrosis occurs as a complication of hemochromatosis, Wilson's disease, alcoholism, schistosomiasis, viral hepatitis, bile duct obstruction, exposure to toxins, and metabolic disorders. This formation of scar tissue is believed to represent an attempt by the body to encapsulate the injured tissue. Liver fibrosis is characterized by the accumulation of extracellular matrix that can be distinguished qualitatively from that in normal liver. Left unchecked, hepatic fibrosis progresses to cirrhosis (defined by the presence of encapsulated nodules), liver failure, and death. As summarized by Li and Friedman (Gastroenterol. Hepatol. 14:618-633, 1999), actual and proposed therapeutic strategies for liver fibrosis include removal of the underlying cause (e.g., toxin or infectious agent), suppression of inflammation (using, e.g., corticosteroids, IL-1 receptor antagonists, or other agents), down-regulation of stellate cell activation using, e.g., gamma interferon or antioxidants), promotion of matrix degradation, or promotion of stellate cell apoptosis.

Fibrotic tissues accumulate in the heart and blood vessels as a result of hypertension, hypertensive heart disease, atherosclerosis, and myocardial infarction. High blood pressure, or hypertension, can be cause by a variety of factors and often leads to the development of Hypertensive Heart Disease (HHD) with progression to cardiac arrest and myocardial infarction. Similarly, atherosclerosis and other ischemic heart diseases often also result in cardiac arrest. These cardiovascular diseases all exhibit an accumulation of extracellular matrix or fibrotic deposition which results in stiffening of the vasculature and stiffening of the cardiac tissue itself. This deposition of fibrotic material is a response to the damage induced by the hypertensive and/or sclerotic state, but the effects of this response also result in the negative effects of vascular and cardiac stiffening as well as ventricle enlargement. In some instances, the increased cardiac fibrosis in cardiovascular disease disrupts or alters the signals transmitted to cardiomyocytes via the tissue scaffolding of the heart, further leading to disruption of efficient cardiac function and promoting cardiac arrest and myocardial infarction.

In accordance with the present disclosure, expression profiles of genes differentially regulated during tissue damage can be used to assess reversal of tissue damage in a method of treatment disclosed herein. For example, microarray-based analysis of gene expression can be based on the analysis of human cells (such as fibroblasts and cardiomyocytes) subject to selected stimuli resulting in changes in extracellular collagen accumulation and proliferation, the hallmarks of fibrosis. The stimuli can be selected to mimic those in the tissue-specific fibrosis process. Gene expression files associated with fibrosis (e.g., liver fibrosis, lung fibrosis, heart tissue fibrosis, diabetic nephropathy, and kidney fibrosis) can then be used to assay fibrosis and reversal of fibrotic damages to the tissue. In other embodiments, gene expression files associated with reversal of fibrosis (e.g., under a treatment known to at least partially reverse fibrosis) can be used to assay fibrosis and reversal of fibrotic damages to the tissue.

In some embodiments, there is provided a method of reconstructing the microenvironment of neurofibril cells and neurosecretory cells at the site of injury in a tissue of an individual having a tissue injury, comprising delivering to the site of injury an effective amount of a trace element. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element. In some embodiments, the tissue is heart, liver, brain, lung, kidney, skin, digestive tract, reproductive organs, bone, or skeletal muscle. In some embodiments, the tissue is heart.

The microenvironment is an intricate network of both structural and inflammatory cells, cytokines, proteins, and growth factors. In the case of heart fibrotic diseases or conditions, the heart comprises resident structural cells such as cardiomyocytes, epithelial cells, fibroblasts, and resident cardiomyocyte progenitors and cytokine secreting cells. These cells interact with fibrotic factors during the pathogenesis of fibrosis. In certain aspects, fibroblasts and myofibroblasts play an important role in creating a fibrotic environment, as they secrete excess collagen and matrix materials that lead to irreversible scarring. Cell-to-cell adhesion molecules and extracellular matrix ligands are important factors in the fibrotic microenvironment and promote fibrosis and fibroblast differentiation. In some embodiments, adhesion-mediated signaling is assayed in the tissue microenvironment. For example, cell differentiation and migration occurs in response to mechanic cues from the microenvironment, such as stiffness of the surrounding matrix. In one aspect, elasticity of the tissue or culture matrices of mesenchymal stem cells (MSCs) are assayed and modulated to promote stem cell homing to the injured tissue, stem cell differentiation at the injury site, tissue repair, and/or reversal of tissue damages. In one embodiment, soft matrices result in differentiation of MSCs into neuron-like cells, whereas stiff matrices result in differentiation of MSCs into myogenic. In one aspect, the extracellular matrix and its components of the injury site are assayed to indicate whether the microenvironment promotes stem cell migration to the site, stem cell differentiation at the injury site, tissue repair, and/or reversal of tissue damages.

In some embodiments, changes in cells in the context of their natural environment are measured to indicate efficacy and/or toxicity of a therapeutic method disclosed herein. In some aspects, stem cell microenvironment of a donor tissue or organ (such as the bone marrow) and of an injury site are assayed and/or modulated to promote stem cell migration to the site, stem cell differentiation at the injury site, tissue repair, and/or reversal of tissue damages. Local tissue microenvironment can be assayed by protein stains (IHC and IF) and RNA staining with both chromogenic and fluorescent ISH. For example, hypoxic microenvironment can be indicated by hypoxic marker staining, endothelial cell marker staining, micro-vessel density analysis, and proximity analysis. Tissue microenvironment can also be studied using organ cultures or organotypic cultures as disclosed in Benbrook, 2006, Drug Discovery Today: Disease Models, 3(2): 143-148.

In some embodiments, there is provided a method of inducing at least two (including for example at least any of 3, 4, 5, 6, or more) events of tissue repair in an individual having a tissue injury, comprising delivering to the site of injury an effective amount of a trace element, wherein the at least two events of tissue repair are selected from the group consisting of: inducing the migration of stem cells such as bone marrow mesenchymal stem cells to the site of injury, inducing differentiation of stem cells at the site of injury, inducing tissue regeneration at the site of injury, inducing a signaling molecule that triggers tissue regeneration, reversing damage at the site of injury, and reconstructing the microenvironment of neurofibril cells and neurosecretory cells at the site of injury. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element. In some embodiments, the tissue is heart, liver, brain, lung, kidney, skin, digestive tract, reproductive organs, bone, or skeletal muscle. In some embodiments, the tissue is heart.

In some embodiments, there is provided a method of inducing the migration of stem cells (such as MSC, for example BMSC) to the site of injury and inducing differentiation of stem cells at the site of injury, comprising delivering to the site of injury an effective amount of a trace element. In some embodiments, there is provided a method of inducing the migration of stem cells (such as MSC, for example BMSC) to the site of injury and inducing tissue regeneration at the site of injury, comprising delivering to the site of injury an effective amount of a trace element. In some embodiments, there is provided a method of inducing the migration of stem cells (such as MSC, for example BMSC) to the site of injury, inducing differentiation of stem cells at the site of injury, and inducing tissue regeneration at the site of injury, comprising delivering to the site of injury an effective amount of a trace element. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element.

Methods of Inducing tissue repair and blood vessel growth via directly delivery

The present application in one aspect provides a method of inducing tissue repair in an individual having a tissue injury, comprising delivering an effective amount of a trace element directly into the site of injury. In some embodiments, the trace element is copper. In some embodiments, the tissue is heart, liver, brain, lung, kidney, skin, digestive tract, reproductive organs, bone, or skeletal muscle. In some embodiments, the tissue is heart.

In some embodiments, there is provided a method of inducing tissue repair in an individual having a tissue injury without increasing the expression of VEGF at the site of injection, comprising delivering an effective amount of a trace element directly into the site of injury. In some embodiments, the trace element is copper. In some embodiments, the tissue is heart, liver, brain, lung, kidney, skin, digestive tract, reproductive organs, bone, or skeletal muscle. In some embodiments, the tissue is heart.

In some embodiments, there is provided a method of inducing blood vessel growth towards the site of injury in an individual having a tissue injury, comprising delivering an effective amount of a trace element directly into the site of injury. In some embodiments, the trace element is copper. In some embodiments, the tissue is heart, liver, brain, lung, kidney, skin, digestive tract, reproductive organs, bone, or skeletal muscle. In some embodiments, the tissue is heart.

In some embodiments, there is provided a method of inducing blood vessel growth towards the site of injury in an individual having a tissue injury without increasing the expression of VEGF at the site of the injection, comprising delivering an effective amount of a trace element directly into the site of injury. In some embodiments, the trace element is copper. In some embodiments, the tissue is heart, liver, brain, lung, kidney, skin, digestive tract, reproductive organs, bone, or skeletal muscle. In some embodiments, the tissue is heart.

The formation and growth of blood vessels within a tissue may occur by angiogenesis and/or vasculogenesis. In one aspect, blood vessels include capillary-like structures that are fully functional to support the transport of blood. In some embodiments, angiogenesis includes a process involving the growth of new blood vessels from pre-existing vessels, sprouting angiogenesis, the formation of new blood vessel by sprouting off existing ones, or splitting angiogenesis (intussusception), the formation of new blood vessel by splitting off existing ones. In some embodiments, vasculogenesis includes a process involving the de novo production of new blood-vessels by proliferating endothelial stem cells, such as the formation of new blood vessels when there were no pre-existing ones.

In some embodiments, blood vessel formation and growth requires signals from growth factors and other proteins that directly control the process, such as angiopoietins (like Ang-1 and Ang-2), ephrin (Eph), vascular endothelial growth factors (like VEGF-A and VEGF-C), platelet derived growth factor (PDGF), fibroblast growth factors (like FGF-1 and FGF-2), tumor necrosis factor-α (TNF-α), interleukin (IL), monocyte chemotactic protein-1 (MCP-1) (also known as CCL-2), transforming growth factor-α (TGF-α), transforming growth factor-βs (like TGF-β1, TGF-β2, TGF-β3, and TGF-β4), endostatin, vasohibin, chemokines, thrombospondin, angiostatin, vascular cell adhesion molecules (like VCAM-1), matrix metalloproteinases (like MMP-2 and MPP-9), integrins, cadherins, plasminogen activators, and plasminogen activator inhibitors.

In some embodiments, blood vessel growth is assayed by measuring endothelial cell proliferation, which is needed for developing capillaries in the intact animal. In some embodiments, the action of a trace element directly delivered into the site of injury on endothelial proliferation can be assessed by direct cell counts, DNA synthesis, and/or metabolic activity. For example, endothelial cells can be isolated from the site of injury and assayed for their proliferation rate after treatment with a trace element. In other embodiments, the proliferation of endothelial cells at the site of injury can be monitored by labeling the cells and measuring cell counts, DNA synthesis, and/or metabolic activity in situ. In other embodiments, labeled endothelial cells can be administered to a subject, and the proliferation of labeled endothelial cells at the site of injury can be monitored in situ. In some embodiments, endothelial cells are labeled with a radioisotope, a fluorescent moiety, or a marker that can be specifically detected, for example, by an antibody. In specific embodiments, the cells are labeled with [$^3$H]thymidine or bromodeoxyuridine (BrdU).

In some embodiments, blood vessel growth is assayed by measuring migration of endothelial cells, which degrade the basement membrane and migrate along chemical gradients established by proangiogenic growth factors, for example, during sprouting angiogenesis. In certain embodiments, endothelial cells at the site of injury are labeled and cell migration is monitored in vivo. In other aspects, labeled endothelial cells are administered to a subject, and their migration toward the site of injury is monitored in vivo. In other aspects, the endothelial cells at the site of injury can be isolated and their migratory properties can be assayed by a number of in vitro assays including the Boyden chamber assay, under-agarose assay, wound healing assay, Teflon fence assay, phagokinetic track assay, and like assays.

In some embodiments, blood vessel growth is assayed by measuring endothelial cells forming tubes with lumens to conduct the flow of blood, i.e., tubulogenesis. In some embodiments, blood vessel growth is assayed by an aortic ring assay. An aortic ring assay for assaying blood vessel growth is disclosed in Li et al., "Copper promotion of angiogenesis in isolated rat aortic ring: role of vascular endothelial growth factor," Journal of Nutritional Biochemistry 25(2014) 44-49, the disclosure of which is incorporated herein by reference in its entirety. The sprouting microvessels from the aortic ring interact closely with resident macrophages, pericytes, and fibroblasts in an orderly sequence that emulates angiogenesis in the intact animal. In some aspects, the endothelial cells have not been preselected by passaging and are thus in a quiescent state similar to that of the intact animal. Other angiogenesis assays that incorporate angiogenic functions (such as matrix degradation, migration, proliferation, tube formation) include the embryoid assay, mouse metatarsal assay, and like assays.

In some embodiments, an in vivo assay is used to measure blood vessel growth after a trace element is directly delivered into the site of injury. These assays include and are not limited to the corneal angiogenesis assay, chick chorioallantoic membrane assay, and Matrigel plug assay. For example, the cornea is the only tissue of the body that is both avascular and transparent, making it ideal for observation of angiogenesis. In one aspect, pellets or sponges containing proangiogenic molecules (for example, a trace element as disclosed herein) can be implanted into stromal pockets created surgically. The ingrowth of new vessels from the peripheral limbal vasculature can be monitored daily, allowing rates of angiogenesis to be determined. In a Matrigel plug assay, a Matrigel containing a trace element as disclosed herein can be implanted in a subject at or near the site of injury, and the Matrigel plug is later removed for visualization of blood vessels. In some embodiments, the endothelial cells are labeled with one or more markers, and their proliferation, migration, tubulogenesis, blood vessel formation, and/or blood vessel growth at the site of injury are assayed in vivo, for example, using a suitable imaging technique.

In some embodiments, there is provided a method of inducing migration (i.e., homing) of stem cells (such as MSC, for example BMSC), to a site of injury in a tissue of an individual having a tissue injury, comprising delivering an effective amount of a trace element directly to the site of injury.

In some embodiments, there is provided a method of inducing differentiation of stem cells and/or inducing tissue regeneration at the site of injury, comprising delivering an effective amount of a trace element directly to the site of injury.

In some embodiments, there is provided a method of inducing tissue regeneration at the site of injury in an individual, comprising delivering an effective amount of a trace element directly to the site of injury.

In some embodiments, there is provided a method of reversing damage at the site of injury in a tissue of an individual, comprising delivering an effective amount of a trace element directly to the site of injury.

In some embodiments, there is provided a method of reconstructing the microenvironment of neurofibril cells and neurosecretory cells at the site of injury in a tissue of an individual having a tissue injury, comprising delivering an effective amount of a trace element directly to the site of injury.

In some embodiments, there is provided a method of inducing at least two (including for example at least any of 3, 4, 5, 6, or more) events of tissue repair in an individual having a tissue injury, comprising delivering an effective amount of a trace element directly into the site of injury, wherein the at least two events of tissue repair are selected from the group consisting of: inducing the migration of stem cells (such as MSC, for example BMSC) to the site of injury, inducing differentiation of stem cells at the site of injury, inducing tissue regeneration at the site of injury, inducing a signaling molecule that triggers tissue regeneration, reversing damage at the site of injury, and reconstructing the microenvironment of neurofibril cells and neurosecretory cells at the site of injury. In some embodiments, the trace element is copper. In some embodiments, the tissue is heart, liver, or skeletal muscle. In some embodiments, the tissue is heart.

In some embodiments, there is provided a method of inducing the migration of stem cells (such as MSC, for example BMSC) to the site of injury and inducing differentiation of stem cells at the site of injury, comprising delivering an effective amount of a trace element directly to the site of injury. In some embodiments, there is provided a method of inducing the migration of stem cells (such as MSC, for example BMSC) to the site of injury and inducing tissue regeneration at the site of injury, comprising delivering an effective amount of a trace element directly to the site of injury. In some embodiments, there is provided a method of inducing the migration of stem cells (such as MSC, for example BMSC) to the site of injury, inducing differentiation of stem cells at the site of injury, and inducing tissue regeneration at the site of injury, comprising delivering an effective amount of a trace element directly to the site of injury.

Combination Therapy with Stem Cells or Inducers

The present application in another aspect provides a method of inducing tissue repair (or improving the function of the tissue) in an individual having a tissue injury, comprising: a) delivering to the site of injury an effective amount of a trace element; and b) administering to the individual an effective amount of stem cells (such as mesenchymal stem cells (MSC), for example bone marrow mesenchymal stem cells (BMSC)) or an inducer of stem cells. In some embodiments, the method comprises administering to the individual an effective amount of stem cells (such as MSC, for example BMSC). In some embodiments, the method comprises administering to the individual an effective amount of inducer of stem cells. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element.

In some embodiments, the stem cell disclosed herein is a mesenchymal stem cell (MSC), a bone marrow mesenchymal stem cell (BMSC), a multipotent stem cell, an induced pluripotent stem cell (iPS), or a tissue-derived stem cell. In some embodiments, the tissue-derived stem cell is an adipose tissue-derived stem cell, a cardiac tissue-derived stem cell, or an umbilical cord tissue-derived stem cell. In some embodiments, the stem cell is an inducer of an adult stem cell. In some embodiments, the adult stem cell is a hematopoietic stem cell, a mammary stem cell, an intestinal stem cell, a mesenchymal stem cell in the placenta, adipose tissue, lung, bone marrow, blood, Wharton's jelly of the umbilical cord, or teeth (such as the perivascular niche of dental pulp and periodontal ligament), an endothelial stem cell, a neural stem cell, an olfactory adult stem cell, a neural crest stem cell, or a germline stem cell (for example, a stem cell in the testicle).

In some embodiments, the inducer of the stem cell disclosed herein is an inducer of a mesenchymal stem cell (MSC), a bone marrow mesenchymal stem cell (BMSC), a multipotent stem cell, an induced pluripotent stem cell (iPS), or a tissue-derived stem cell, such as an adipose tissue-derived stem cell, a cardiac tissue-derived stem cell, or an umbilical cord tissue-derived stem cell. In some embodiments, the inducer of stem cell is an inducer of an adult stem cell, such as a hematopoietic stem cell, a mammary stem cell, an intestinal stem cell, a mesenchymal stem cell in the placenta, adipose tissue, lung, bone marrow, blood, Wharton's jelly of the umbilical cord, or teeth (such as the perivascular niche of dental pulp and periodontal ligament), an endothelial stem cell, a neural stem cell, an olfactory adult stem cell, a neural crest stem cell, or a germline stem cell (for example, a stem cell in the testicle).

In some embodiments, an inducer of mesenchymal stem cells of the present disclosure is an agent that induces mesenchymal stem cell formation in a tissue, for example, in the bone marrow. In certain aspects, an inducer of mesenchymal stem cells induces mesenchymal stem cell formation from an undifferentiated stem cell or a pluripotent stem cell. In some aspects, the stem cell is an embryonic stem cell or an induced pluripotent stem cell (iPS). The stem cell can be in vivo, in vitro, or ex vivo. In other aspects, the stem cell is a human embryonic stem cell or a human induced pluripotent stem cell.

In some aspects, an inducer of mesenchymal stem cells of the present disclosure is selected from the group consisting of a BMP protein, basic fibroblast growth factor (bFGF), BMP 4, BMP 2, activin A, a BMP 4 antagonist, Noggin, Chordin, Tsg, a BMP soluble receptor, BMPRIA, BMPRIB, a small molecule which acts or functions like BMP antagonist, Dorsomorphin, an inhibitor of retinoic acid signaling pathway, a pan-retinoic acid receptor antagonist, a retinoic acid antagonist, a retinoic acid receptor antagonist, a retinoic X receptor antagonist, Wnt-3a, dickkopf homolog 1 (DKK1), and a small molecule which acts or functions like Wnt-3a, such as Bio or CHIR99021. In one aspect, a mesenchymal stem cell inducer comprises one or more inducers disclosed herein. In one aspect, a mesenchymal stem cell inducer increases mesenchymal stem cells in the blood.

In some embodiments, there is provided a method of inducing tissue repair (or improving the function of the tissue) in an individual having a tissue injury and is administered with stem cells (such as MSC, for example BMSC), comprising delivering to the site of injury an effective amount of a trace element. In some embodiments, there is provided a method of inducing migration of stem cells (such as MSC, for example BMSC) to the site of injury in an individual having a tissue injury, comprising delivering to the site of injury an effective amount of a trace element, wherein the stem cells are administered to the individual. In some embodiments, there is provided a method of inducing differentiation of stem cells (such as MSC, for example BMSC) to the site of injury in an individual having a tissue injury, comprising delivering to the site of injury an effective amount of a trace element, wherein the stem cells are administered to the individual. In some embodiments, the method further comprises administering to the individual an effective amount of inducer of stem cells (such as MSC, for example BMSC). In some embodiments, the trace element is copper. In some embodiments, the tissue is heart, liver, brain, lung, kidney, skin, digestive tract, reproductive organs, bone, or skeletal muscle. In some embodiments, the tissue is heart.

In some embodiments, there is provided a method of inducing tissue repair (or improving the function of the tissue) in an individual having a tissue injury and is administered with an inducer of a stem cell (such as MSC, for example BMSC), comprising delivering to the site of injury an effective amount of a trace element. In some embodiments, there is provided a method of inducing migration of stem cells (such as MSC, for example BMSC) to the site of injury in an individual having a tissue injury, comprising delivering to the site of injury an effective amount of a trace element, wherein an inducer of the stem cells is administered to the individual. In some embodiments, there is provided a method of inducing differentiation of stem cells (such as MSC, for example BMSC) to the site of injury in an individual having a tissue injury, comprising delivering to the site of injury an effective amount of a trace element, wherein an inducer of the stem cells is administered to the individual. In some embodiments, the method further comprises administering to the individual an effective amount of stem cells (such as MSC, for example BMSC). In some embodiments, the trace element is copper. In some embodiments, the tissue is heart, liver, brain, lung, kidney, skin, digestive tract, reproductive organs, bone, or skeletal muscle. In some embodiments, the tissue is heart.

The methods described herein are generally suitable for inducing homing of stem cells to an injury site, which can includes migration of endogenous stem cells to the injury site, migration of exogenous stem cells to the injury site, or both.

In some embodiments, the stem cell used herein is modified to enhance its homing response. In one embodiment, the stem cells migrate to the injury site via a blood vessel and/or via local migration. For example, the stem cells (such as MSCs) can be chemically, enzymatically, and/or genetically modified to enhance their migration and homing responses.

In one aspect, sialyl Lewis$^x$ (SLeX) moiety, a cell rolling ligand, is covalently coupled onto the surface of stem cells through biotin-streptavidin chemical modifications. In some embodiments, the SLeX engineered MSCs exhibit a rolling response in vitro on substrates coated with P-selectin. Sarkar et al., 2008, Bioconjugate Chemistry 19, 2105-2109. It is to be understood that other suitable chemical, enzymatic, and/or genetic modifications can be used to enhance stem cell migration and homing to injured tissue sites.

In some embodiments, the stem cells are from multiple different tissues with differences in the phenotype of the cells. These differences may in part due to differences in the native microenvironment from where they are isolated. Apart from the source of the stem cells, culture methods greatly influence stem cells characteristics, including their homing potential. In certain embodiments, freshly isolated stem cells home better than their cultured counterparts. In one aspect, the CXCR4 chemokine receptor that recognizes SDF-1α is highly expressed on BMSCs, but is lost upon culturing. In some embodiments, stem cells are cultured with cytokines (such as HGF, SCF, IL-3, and IL-6), and/or under hypoxic conditions, resulting in reestablishment of CXCR4 expression. In other embodiments, matrix metalloprotease (MMP) signaling is regulated using a method disclosed herein to regulate cell migration. Expression of MMPs in MSCs is influenced by factors such as hypoxia and increased culture confluence. Moreover, inflammatory cytokines TGF-β1, IL-1β, and TNF-α also enhance migration by upregulation of MMPs (MMPs) affecting homing of MSCs.

Tissue repair can be assessed, for example, by the area of damage or volume of damage. The repair of damaged tissue in a patient can be assessed using any clinically relevant standard. For example, repair of infracted tissue can be measured by quantitation of cell number, such as the number of myocytes, fibroblast, or amount of scarring, or with functional assays for output or structural aspects of heart function including, LVEDP, LVDP, max dp/dt, min dp/dt, LV Weight, Chamber Volume, and Diastolic Wall Stress. In general, a method disclosed herein is said to repair damaged tissue if it results in a significant (e.g., at least 2-fold) change in any such clinical assessment or any combination thereof.

Any appropriate method(s) can be performed to assay tissue repair. For example, methods can be performed to assess tissue healing, to assess functionality of repaired tissue, and to assess cellular growth in the tissue. To determine the extent of tissue healing, histology and cell staining can be performed to detect seeded cell propagation and/or improved histological appearance. In some cases, tissue portions can be collected and treated with a fixative such as, for example, neutral buffered formalin. Such tissue portions can be dehydrated, embedded in paraffin, and sectioned with a microtome for histological analysis. Sections can be stained with hematoxylin and eosin (H&E) and then mounted on glass slides for microscopic evaluation of morphology and cellularity. In some cases, physiological tests can be performed to assess tissue movement and functionality following treatment according to the methods and materials provided herein. For example, in vitro mechanical assays can be performed to measure the work of flexion (WOF) or flexion angle of a repaired tendon tissue or of a repaired joint. In vivo assays can include functional evaluation of the organs, symptom assessment, or imaging techniques.

In some embodiments, tissue and/or organ function before, during, or after administering a therapeutic method disclosed herein can be assessed by any one or more of the following methods: biochemical analysis of at least one biomarker indicative of improved tissue function by methods such as flow cytometry, immunofluorescence, ELISA, phosphor-labeling, hybridization, nucleic acid amplification, or Western blot; cellular function assays, such as cell apoptosis assays, necrosis assays, and cell viability assays, including Annexin V staining by immunofluorescence or flow cytometry, detection of caspase activity, hypoxia assays, TUNEL assay, cell DNA laddering, number of rod-shaped cells in response to $H_2O_2$, qPCR assessment of gene expression, and measuring necrotic area by H&E staining; scar formation assays, including measuring number of fibroblastic cells in a damaged or infarct area, measuring collagen deposition and level of other matrix proteins associated with scar formation; migration of stem cells or progenitor cells into the damaged area; and any other clinically relevant organ function tests.

In some embodiments, cardiac function can be assessed by any one or more of the following parameters: myocyte mechanics and cell fusion, for example, frequency of distribution of myocyte size, peak shortening, velocity of shortening and re-lengthening, and assessment of cell fusion (number of X chromosomes); output or structural aspects of heart function including, LVEDP, LVDP, +dp/dT, LV Weight, Chamber Volume, Diastolic Wall Stress, and comparison of MI-treated and MI-untreated subjects; myocardial regeneration, such as composition of regenerated myocardium, assessment of BrdU positive cells in infarct area in treated versus untreated subjects, and myosin positive cells in the infarct area in treated versus untreated subjects; cardiac structural, such as infarct size, amount of fibrosis, and cardiomyocyte hypertrophy. In certain embodiments, a method disclosed herein further comprises measuring one or more indicia of cardiac function, wherein said indicia of cardiac function are chest cardiac output (CO), cardiac index (CI), pulmonary artery wedge pressure (PAWP), cardiac index (CI), % fractional shortening (% FS), ejection fraction (EF), left ventricular ejection fraction (LVEF); left ventricular end diastolic diameter (LVEDD), left ventricular end systolic diameter (LVESD), contractility (dP/dt), a decrease in atrial or ventricular functioning, an increase in pumping efficiency, a decrease in the rate of loss of pumping efficiency, a decrease in loss of hemodynamic functioning, or decrease in complications associated with cardiomyopathy, as compared to a control.

In some embodiments, brain function before, during, or after administering a therapeutic method disclosed herein can be assessed by a neurological testing, or electrophysiologically, for example by a decreased signal to noise ratio, or biochemically, for example, by analysis of at least one biomarker indicative of organ function, tissue function, and/or cellular function of the central or peripheral nervous system. Exemplary electrophysiological techniques include electroencephalography (EEG), electrocardiography (EKG), electromyography (EMG), event-related potentials (ERPs), evoked potentials (EPs), magnetoencephalography (MEG), and nerve conduction study (NCS). In other embodiments, brain function can be assessed by any one or more of the following methods or parameters: general intellectual function, such as Wechsler Abbreviated Scale of Intelligence and Wechsler Adult Intelligent Scale-III; basic attention, such as Digit Span, Spatial span subtests from the Wechsler Memory Scale-III; complex attention (working memory), such as Digit Span, Letter Number Sequencing and Arithmetic subtests from the Wechsler Adult Intelligence Scale-III; executive functions, such as Wisconsin Card Sorting Test, Trail Making Test B, Stroop Test, Tower of London Test, Gambling Test, Frontal System Behavior Scale, and Iowa Scales of Frontal Lobe Function; memory (visual and verbal), such as Wechsler Memory Scales-III, Rey Auditory, Verbal Learning Test, California Verbal, Learning Test-II, Brief Visual Memory Test Revised; affect regulation, such as Minnesota Multiphasic Personality Inventory-2, Affective Stroop Test, Frontal System Behavior Scale, and Iowa Scales of Frontal Lobe Function; interpretation of emotion stimuli, such as DANVA (Diagnostic Analysis of Nonverbal Behavior); processing speed, such as Processing Speed index (Symbol Search, Coding) from the Wechsler Adult Intelligent Scale-III, Trail Making Test, and Symbol Digit Modalities Test; language, such as Boston Naming Test; Controlled Oral Word Association Test; Semantic Word Fluency Test; and Multilingual Aphasia Examination; visuo-constructional tests, such as Rey-Osterrieth Complex Figure Test, Block Design, and Object Assembly subtests from the Wechsler Adult Intelligence Scale-III; and visuo-spatial tests, such as Matrix Reasoning from the WAIS-III, and Judgment of Line Orientation Test.

In some embodiments, skeletal muscle health before, during, or after administering a therapeutic method disclosed herein is tested. In some embodiments, skeletal muscle health includes muscle soreness, muscle damage, metabolic changes to exercise, and cytoskeletal re-organization. The skeletal muscle function can be muscle strength, muscle endurance, training adaption, a normal state of the muscle that will allow movement of the joints, or standard physiological metabolism and function of skeletal muscle in a healthy mammal. Any functional variable of the skeletal muscle can be measured, including muscle strength (maximal force generated in a specific movement), muscle endurance (the maximal number of contractions which can be performed at a set frequency and force), and muscle power (force/time, the maximal effect generated by the muscle). While not exhaustive, typical muscle-specific functions include myoblast differentiation, myoblast determination, muscle development, muscle contraction, sarcomeric changes, myoblast fusion, somatic muscle development, and myogenesis.

In certain embodiments, skeletal muscle fibrosis of a patient is assessed. A number of methods are available to determine the state of skeletal muscle fibrosis, including obtaining a biopsy of muscle tissue from the patient, and evaluating the biopsy with histochemical or immuno-histochemical stains sensitive to detect the existence of fibrotic tissue. Examples of histochemical stains include, for example, hematoxylin and eosin (H&E), trichrome and ATPase (e.g., at pH 4.3, 4.65 and 10.4). Representative antibodies which can be used to label muscle fibers for immuno-histochemical staining include, for example, myosin, type IV collagen, laminin, fibronectin and dystrophin. Alternatively, a functional method of determining the extent to which fibrosis pervades a patient's skeletal muscle can be employed. The functional method involves subjecting the patient to one or more of a battery of tests and physical measurements. Such tests and measurements typically include neurological strength tests, muscle strength, balance, gait, posture, sensory coordination evaluations, and pulmonary function tests, e.g., vital capacity and forced expiratory capacity, all of which can be carried out by methods known in the art. In some embodiments, tissue repair can be assessed based on the expression level(s) of one or more signaling molecules described herein. Suitable biomarkers as indicators of tissue repair include, but are not limited to, a DNA-damage biomarker, an inflammatory-response biomarker, a tissue-damage biomarker, a tissue-damage repair biomarker, or a hematology-surrogate marker, such as p53, p21, GADD45a, ATM, phosphorylated H2AX histone, IL-6, CRP, SAA, IL-1, IL-5, IL-10, KC/GRO, IFN, IL-2, IL-4, TNF-alpha, IL-12, IL-3, IL-7, IL-6, salivary beta-amylase, citrulinated proteins, S100B, SP-D, BPI, TSP, CA15-3, CDBB, CKMB, CKMM, FABP2, GFAP, NSE, CDS, CD-16b, CD20, CD177, CD26, CD27, CD40, CD45, Flt-3L, G-CSF, KFG, EPO, TPO, GM-CSF, or SDF-1α.

In some embodiments, a trace element disclosed herein is a regulator of one or more factors (for example, transcriptional factors) involved in repair of tissue damage and/or in tissue regeneration. Copper regulated factors include but are not limited to: Cu homeostasis proteins, such as Ctr 1, Ctr 3, DMT1, Atox 1, ATP7A/7B, Cox 17, CCS, Sco 1/2, Cox 11, Glutamatergic N-methyl D-aspartate receptors (NMDAR), Amyloid precursor protein (APP), Copper metabolism gene MURR1 domain (COMMD1), X-linked inhibitor of apoptosis (XIAP), homocysteine (Hcy), subunit II of cytochrome c oxidase (COX II), subunit I of cytochrome c oxidase (COX I), FGF-1, VEGF, angiopoietin (such as ANG1 or ANG2), fibronectin, collagenase, MMPs-TIMPs, elastin, PDGF, and eNOS; intracellular Cu binding proteins, such as Cytochrome C oxidase (CCO), Superoxide dismutase (SOD), Metallothionein (MT), Glutathione (GSH), Dopamine-β-monooxygenase (DBH), Peptidylglycine-α-amidating monooxygenase (PAM), Tyrosinase, Phenylalanine hydroxylase, Diamine oxidase, Hephaestin, and Cartilage matrix glycoprotein; extracellular Cu binding proteins, such as Ceruloplasmin (CP), Lysyl oxidase (LOX), Albumin (ALB), Transcuprein, Amine oxidase, Blood clotting factors V and VIII, Ferroxidase II, Extracellular superoxide dismutase, and Extracellular metallothionein. Copper regulated factors are disclosed in Zheng et al., Role of copper in regression of cardiac hypertrophy, Pharmacol. Ther. doi: 10.1016/j.pharmthera.2014.11.014 (2014), which is incorporated herein by reference. In particular aspects, the trace element regulates the transcriptional activity of one or more of HIF-1, SP1, MT, Atox 1, CCS, and COMMD1, and the signaling networks regulated by these transcriptional factors.

In some aspects, the level and/or activity of one or more factors regulated by a trace element disclosed herein are analyzed in an individual following treatment with a therapeutic or preventive composition disclosed herein. In particular aspects, the level and/or activity of one or more of HIF-1, SP1, MT, Atox 1, CCS, and COMMD1 are determined, and then correlated with a response of the individual to the therapeutic or preventive composition. In some aspects, the response is detected by measuring cellular markers of normal tissue homeostasis and/or of persistent tissue damage (for example, by immunohistochemistry or measuring DNA and transcript levels), measuring the area of damage or volume of damage, or assessing any clinically relevant indicators. Thus, in certain aspects, the level and/or activity of one or more trace element regulated factors (such as HIF-1, SP1, MT, Atox 1, CCS, and COMMD1) can be used as an end-point biomarker of an individual's response to a therapeutic or preventive regimen disclosed herein.

In some embodiments, one or more factors regulated by a trace element disclosed herein can be used to analyze and predict a response to a composition or treatment or preventive method disclosed herein. For example, the level and/or activity of one or more of HIF-1, SP1, MT, Atox 1, CCS, and COMMD1 can indicate a likelihood that an individual will respond positively to a treatment or preventive composition disclosed herein, the treatment or preventive composition may be administered to the individual. Conversely, if the level and/or activity of one or more of HIF-1, SP1, MT, Atox 1, CCS, and COMMD1 indicate that an individual is likely not to respond or to respond negatively to the treatment or preventive composition, an alternative course of treatment may be prescribed. A negative response may be defined as either the absence of an efficacious response or the presence of toxic side effects. The response to a therapeutic or preventive treatment can be predicted in a background study in which subjects in any of the following populations are genotyped: a population that responds favorably to a treatment regimen, a population that does not respond significantly to a treatment regimen, and a population that responds adversely to a treatment regimen (e.g. exhibits one or more side effects). These populations are provided as examples and other populations and subpopulations may be analyzed. Based upon the results of these analyses, a subject is genotyped to predict whether he or she will respond favorably to a treatment regimen, not respond significantly to a treatment regimen, or respond adversely to a treatment regimen. Thus, in certain aspects, the level and/or activity of one or more of HIF-1, SP1, MT, Atox 1, CCS, and COMMD1 can be used as response indicators of an individual to a therapeutic or preventive regimen disclosed herein. The response indicators can be assessed before, during, and/or after administering the therapeutic or preventive regimen. For example, one or more response indicators can be assessed during the intervals between doses of a continuous administration, to evaluate whether the subject is likely to benefit from continued treatment or an alternative treatment is needed.

The prognostic tests described herein also are applicable to clinical trials. One or more response indicators (such as HIF-1, SP1, MT, Atox 1, CCS, and COMMD1) may be identified using the methods described herein. Thereafter, potential participants in clinical trials of a trace element composition may be screened to identify those individuals most likely to respond favorably to the composition and exclude those likely to experience side effects. In that way, the effectiveness of treatment may be measured in individuals who respond positively to the trace element composition, without lowering the measurement as a result of the inclusion of individuals who are unlikely to respond positively in the study and without risking undesirable safety problems.

In some embodiments, the stem cells or inducer of stem cells are administered systemically. In some embodiments, the stem cells or inducer of stem cells are administered locally to the site of injury. In some embodiments, the stem cells or inducer of stem cells are administered locally to a site other than the site of injury.

In some embodiments, the stem cells (or inducer of the stem cells) and the trace element are administered simultaneously. In some embodiments, a stem cell disclosed herein (or inducer of the stem cells) and the trace element are administered sequentially in any suitable order.

In specific embodiments, the stem cells (such as MSC, for example BMSC) are administered with other stem cells (such as stem cells that are not BMSCs), myoblasts, myocytes, cardiomyoblasts, cardiomyocytes, or progenitors of myoblasts, myocytes, cardiomyoblasts, and/or cardiomyocytes.

Once the stem cells (or inducer of stem cells) and trace elements described herein are administered to a mammal (e.g., a human), the presence and/or biological activity of the cells in some aspects are monitored by any of a number of known methods. In other embodiments, the cells migrate in vivo from a tissue of a subject, and the presence and/or biological activity of the cells en route to a tissue damage site is monitored and/or regulated.

In some embodiments, the trace element is delivered directly to the injury site. For example, in some embodiments, there is provided a method of inducing tissue repair (or improving the function of the tissue) in an individual having a tissue injury, comprising: a) delivering an effective amount of a trace element directly into the site of injury, and b) administering to the individual an effective amount of stem cells (such as MSC, for example BMSC) or an inducer of stem cells (such as MSC, for example BMSC). In some embodiments, the stem cell disclosed herein is a mesenchymal stem cell (MSC), a multipotent stem cell, or a tissue-derived stem cell. In some aspects, the tissue-derived stem cell is an adipose tissue-derived stem cell, a cardiac tissue-derived stem cell, or an umbilical cord tissue-derived stem cell. In some embodiments, the inducer of stem cells is an inducer of mesenchymal stem cells (MSCs), bone marrow mesenchymal stem cells (BMSCs), multi-potent stem cells, or tissue-derived stem cells, including but not limited to adipose tissue-derived stem cells, cardiac tissue-derived stem cells, and umbilical cord tissue-derived stem cells. In other embodiments, the inducer of stem cells is an inducer of an adult stem cell. In particular aspects, the adult stem cell is a hematopoietic stem cell, a mammary stem cell, an intestinal stem cell, a mesenchymal stem cell in the placenta, adipose tissue, lung, bone marrow, blood, Wharton's jelly of the umbilical cord, or teeth (such as the perivascular niche of dental pulp and periodontal ligament), an endothelial stem cell, a neural stem cell, an olfactory adult stem cell, a neural crest stem cell, or a germline stem cell (for example, a stem cell in the testicle). In some embodiments, the method comprises administering to the individual an effective amount of stem cells (such as MSC, for example BMSC). In some embodiments, the method comprises administering to the individual an effective amount of inducer of bone marrow mesenchymal stem cells. In some embodiments, the trace element is copper. In some embodiments, the tissue is heart, liver, or skeletal muscle. In some embodiments, the tissue is heart.

In some embodiments, there is provided a method of inducing tissue repair (or improving the function of the tissue) in an individual having a tissue injury and is administered with stem cells (such as MSC, for example BMSC), comprising delivering an effective amount of a trace element directly to the site of injury. In some embodiments, there is provided a method of inducing migration of stem cells (such as MSC, for example BMSC) to the site of injury in an individual having a tissue injury, comprising delivering an effective amount of a trace element directly to the site of injury, wherein the stem cells (such as MSC, for example BMSC) are administered to the individual. In some embodiments, there is provided a method of inducing differentiation of stem cells (such as MSC, for example BMSC) to the site of injury in an individual having a tissue injury, comprising delivering an effective amount of a trace element directly to the site of injury, wherein the stem cells (such as MSC, for example BMSC) are administered to the individual. In some embodiments, the method comprises administering to the individual an effective amount of inducer of bone marrow mesenchymal stem cells. In some embodiments, the trace element is copper. In some embodiments, the tissue is heart, liver, or skeletal muscle. In some embodiments, the tissue is heart.

While the methods described herein are generally applicable to all aspects of tissue repair, it is to be understood that the combination therapy methods can be used for the purpose of any one or more of the following: inducing the migration of bone marrow mesenchymal stem cells to the site of injury, inducing differentiation of stem cells at the site of injury, inducing tissue regeneration at the site of injury, inducing a signaling molecule that triggers tissue regeneration, reversing damage at the site of injury, and reconstructing the microenvironment of neurofibril cells and neurosecretory cells at the site of injury.

Further, while the methods described herein focus on combination therapy, it is to be understood that discussions about tissue repair is equally applicable to other sections in the present application (for example the sections immediately below).

Methods of Treating an Individual Having a Compromised Tissue Repair System

The present application in another aspect provides a method of inducing tissue repair (or improving the function of the tissue) in an individual having a compromised tissue repair system, comprising delivering to the site of injury an effective amount of a trace element. In some embodiments, the tissue is heart, liver, or skeletal muscle. In some embodiments, the tissue is heart. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element.

In some embodiments, the individual is more than about 30, about 35, about 40, about 45, about 50, about 55, about 60, about 65, about 70, about 75, about 80, about 85, or about 90 years old. In other embodiments, the individual is younger than about 30 years old. In some embodiments, the individual is at least about 60 (including for example at least about any of 65, 70, 75, 80, 85, 90, or more) years old. In some embodiments, the individual has chronic tissue injury, i.e., has had tissue injury for at least about any of 6, 7, 8, 9, 10, 11, 12, 18, or 24 months. In some embodiments, the individual is deficient in stem cells. In some embodiments, the individual has a defective tissue repair system. In some embodiments, the individual has two or more of the characteristics described above. In some aspects, the individual suffers from one or more of the following symptoms or conditions: loss of memory, low or reduced locomotive ability (including but not limited to force ability, speed endurance, flexibility, and joint moveability), hypoaesthesia, muscle weakness, hearing loss, and chronic strain.

When a biological system is injured, a set of self-repair system is activated. Different organs possess different self-repair ability: liver and muscles trigger better repair than the heart and nerve systems; the younger repair better than the elder. But all biological tissues possess the self-repair system. See, e.g., Kikuchi et al., Annu Rev Cell Dev Biol, 2012, 28:719-41; Garrett et al., J Hand Surg Am, 1984, 9(5):683-92; Porrello et al., Science, 2011, 331(6020): 1078-80; Lin et al., PNAS, 2010, 107(9):4194-9; Greco et al., Cell Stem Cell, 2009, 4(2):155-69; Kajstura et al., Circulation, 2012, 126(15):1869-81; Haubner et al., 2012, 4(12):966-77; J Neurol Sci, 1988, 87(1):67-74; and Friedewald et al., Am J Cardiol, 2012, 110(6):807-16. One of the most crucial components is stem cell homing. Stem cell homing is the oriented migration to the target tissues and surviving of endogenous or exogenous stem cells under complex but organized circumstances. Homing is vital for stem cells to protect the injured tissues.

Under short period of cardiac ischemia, injured tissues initiate the homing of various kinds of stem cells (including bone marrow mesenchymal stem cells, BMSC). Stem cells repair and protect the tissues after their homing. Take BMSCs as an example, homed BMSCs could proliferate and differentiate into myocardium, or repair the injured through paracrine. Some cases have shown that, blocking the homing of stem cells diminished the protection of pretreatment of the heart. Cai et al., Cardiovasc Res, 2008, 77(3): 463-70. Compared with the acute injured ones, tissues with chronic diseases need the repair ability more urgently. However, their self-repair ability is decreased or even lost. Like cardiac ischemia, chronic ischemia results in heart infarction. Both the cardiac function and blood supply constantly decreases, leading to the deterioration of the disease and finally heart failure. The progression of disease is accompanied with the degeneration of the tissue structures and physiological functions. It is obvious that chronic ischemic hearts require structural and functional repair. Nevertheless, with the elongation of ischemia, the spontaneous homing of stem cells diminishes and the heart loses its self-repair ability.

Copper efflux from the heart when the heart is under ischemia. Chevion et al., PNAS, 1993, 90(3):1102-6; Jiang et al., J Exp Med, 2007, 204(3):657-6. Copper inhibits FIH-1 (factor inhibiting HIF-1) within the nucleus, thus is indispensable for the transcriptional activity of HIF-1. When copper is lacking, HIF-1 could not form functional transcription complexes, losing the ability to initiate the expression of HIF-1 regulated genes, such as the homing related chemokine SDF-1. Feng et al., Mol Pharmacol, 2009, 75(1): 174-82; Xie et al., Curr Med Chem, 2009, 16(10):1304-14; Ceradini et al., Nat Med, 2004, 10(8):858-64; Ceradini et al., Trends Cardiovasc Med, 2005, 15(2):57-63. In one aspect, the present disclosure connects stem cell homing with copper efflux, showing that the diminishment of stem cell homing is due to copper efflux during chronic cardiac ischemia. In one aspect, replenishment of copper reverses heart failure. Jiang et al., J Exp Med, 2007, 204(3):657-6; Zhou et al., J Mol Cell Cardiol, 2008, 45(1):106-17. In another aspect, supplement of copper to the heart brings stem cell homing back to the ischemic heart for that copper elevates HIF-1 activity thus promotes the expression of SDF-1.

To target the copper supplement to an injured tissue, in one aspect, Cu-albumin-microbubble is designed and used. After being located and irradiated with ultrasound, copper could be released from the bubble to the target area of heart, increasing copper concentration in the ischemic region. As shown in the present disclosure, treating the heart with Cu-albumin-microbubble can relieve the symptoms caused by chronic cardiac ischemia (FIG. 1): the infarct size was decreased (FIG. 1A, FIG. 1B), EF (ejection fraction) was increased (FIG. 1C) and the vascular density was also lifted (FIG. 1D).

Methods of assessing tissue repair are described in the section above and are not repeated solely for the sake of brevity.

Any of the methods or combination therapy methods described in the section above is generally applicable to an individual having a compromised tissue repair system. For example, in some embodiments, there is provided a method of inducing tissue repair in an individual having a tissue injury and having a compromised tissue repair system, comprising: a) delivering to the site of injury an effective amount of a trace element and b) administering to the individual an effective amount of stem cells (such as MSC, for example BMSC) or an inducer of stem cells. In some embodiments, there is provided a method of inducing migration of stem cells (such as MSC, for example BMSC) to a site of injury in a tissue of an individual having a tissue injury and having a compromised tissue repair system, comprising delivering to the site of injury an effective amount of a trace element, optionally in combination with the administration of an effective amount of stem cells (such as MSC, for example BMSC) or an inducer of stem cells. In some embodiments, the tissue is heart, liver, brain, lung, kidney, skin, digestive tract, reproductive organs, bone, or skeletal muscle. In some embodiments, the tissue is heart. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element.

In some embodiments, there is provided a method of inducing differentiation of stem cells at the site of injury, inducing tissue regeneration at the site of injury and having a compromised tissue repair system, in a tissue of an individual having a tissue injury and having a compromised tissue repair system, comprising delivering to the site of injury an effective amount of a trace element, optionally in combination with the administration of an effective amount of stem cells such as BMSCs or an inducer of stem cells. In some embodiments, the tissue is heart, liver, brain, lung, kidney, skin, digestive tract, reproductive organs, bone, or skeletal muscle. In some embodiments, the tissue is heart. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element.

In some embodiments, there is provided a method of inducing tissue regeneration at the site of injury in a tissue of an individual having a tissue injury and having a compromised tissue repair system, comprising delivering to the site of injury an effective amount of a trace element, optionally in combination with the administration of an effective amount of stem cells such as BMSCs or an inducer of stem cells. In some embodiments, the tissue is heart, liver, brain, lung, kidney, skin, digestive tract, reproductive organs, bone, or skeletal muscle. In some embodiments, the tissue is heart. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element.

In some embodiments, there is provided a method of inducing a signaling molecule that triggers tissue regeneration in a tissue of an individual having a tissue injury and having a compromised tissue repair system, comprising delivering to the site of injury an effective amount of a trace element, optionally in combination with the administration of an effective amount of stem cells such as BMSCs or an inducer of stem cells. In some embodiments, the tissue is heart, liver, brain, lung, kidney, skin, digestive tract, reproductive organs, bone, or skeletal muscle. In some embodiments, the tissue is heart. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element.

In some embodiments, there is provided a method of reversing damage at the site of injury in a tissue of an individual having a tissue injury and having a compromised tissue repair system, comprising delivering to the site of injury an effective amount of a trace element, optionally in combination with the administration of an effective amount of stem cells such as BMSCs or an inducer of stem cells. In some embodiments, the tissue is heart, liver, brain, lung, kidney, skin, digestive tract, reproductive organs, bone, or skeletal muscle. In some embodiments, the tissue is heart. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element.

In some embodiments, there is provided a method of reconstructing the microenvironment of neurofibril cells and neurosecretory cells at the site of injury in a tissue of an individual having a tissue injury and having a compromised tissue repair system, comprising delivering to the site of injury an effective amount of a trace element, optionally in combination with the administration of an effective amount of stem cells such as BMSCs or an inducer of stem cells. In some embodiments, the tissue is heart, liver, brain, lung, kidney, skin, digestive tract, reproductive organs, bone, or skeletal muscle. In some embodiments, the tissue is heart. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element.

In some embodiments, there is provided a method of inducing at least two (including for example at least any of 3, 4, 5, 6, or more) events of tissue repair in an individual having a tissue injury and having compromised tissue repair system, comprising delivering to the site of injury an effective amount of a trace element, optionally in combination with the administration of an effective amount of stem cells such as BMSCs or an inducer of stem cells, wherein the at least two events of tissue repair are selected from the group consisting of: inducing the migration of stem cells to the site of injury, inducing differentiation of stem cells at the site of injury, inducing tissue regeneration at the site of injury, inducing a signaling molecule that triggers tissue regeneration, reversing damage at the site of injury, and reconstructing the microenvironment of neurofibril cells and neurosecretory cells at the site of injury. In some embodiments, the tissue is heart, liver, brain, lung, kidney, skin, digestive tract, reproductive organs, bone, or skeletal muscle. In some embodiments, the tissue is heart. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element and/or a complex thereof is administered by intravenous injection. In some embodiments, the trace element is selected from the group consisting of copper, iron, zinc, and selenium. In some embodiments, the trace element is copper (such as $CuSO_4$ or $CuCl_2$). In some embodiments, the trace element is complexed with a molecule that binds to the trace element. In some embodiments, the trace element is not complexed with any molecule that binds to the trace element.

Methods of Prevention and Prophylactic Use

Also provided herein are methods of preventing tissue injury in an individual comprising administering to the individual an effective amount of a trace element. In some embodiments, the tissue is heart, liver, brain, lung, kidney, skin, digestive tract, reproductive organs, bone, or skeletal muscle. In some embodiments, the tissue is heart. In some embodiments, the trace element is delivered via a microbubble. In some embodiments, the microbubble comprising the trace element is administered intravenously, and the trace element is released through site-directed bursting of the microbubble at the site of the injury. In some embodiments, the site-directed bursting of the microbubble is by ultrasound. In some embodiments, the trace element is delivered by directly administering the trace element to the site of the injury. In some embodiments, the trace element is selected from the group consisting of copper, iron, zinc, and selenium. In some embodiments, the trace element is copper (such as $CuSO_4$). In some embodiments, the trace element is complexed with a molecule that binds to the trace element. In some embodiments, the trace element is not complexed with any molecule that binds to the trace element.

Also provided herein are methods of preventing tissue injury in an individual by directly injecting a trace element to the site where tissue injury is to be prevented.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease such as tissue injury.

For the prevention or treatment of disease, the appropriate dosage or route of administration depend on the type of disease to be treated, the severity and course of the disease, whether the cells are administered for preventive or therapeutic purposes, previous therapy, the subject's clinical history and response to the compositions and/or the cells, and the discretion of the attending physician. The trace element compositions and cells are in some embodiments suitably administered to the subject at one time or over a series of treatments.

In some aspects, tissue damage is caused by depletion of potentially mitotic cells (for example, depletion of stem cells), vascular injury causing hypoxia and other effects, normal host repair responses including induction of immediate early genes such as Jun and EGR1, induction of proinflammatory cytokines such as interleukins and TNF, induction of inflammatory cytokines such as TGFβ, PDGF, BFGF, and induction of secondary cytokine cascade(s), effects of inflammatory responses, and/or interactions between multiple cell types such as inflammatory cells, stromal functional cells and fibroblasts. In other aspects, damage to normal tissue occurs as a consequence of exposure to cytotoxic agents, such as radiation and chemotherapeutics. Radiation may be accidental, environmental, occupational, diagnostic, and therapeutic exposure to radiation. Tissue damage is also a common side effect of cancer treatment such as radiotherapy, chemotherapy, and combination radiotherapy and chemotherapy. In some aspects, the present disclosure provides compositions and methods for treating and preventing tissue damage. In some embodiments, the trace element compositions and/or cells disclosed herein are administered prior to, during, and/or after a treatment which will or likely will cause tissue damage in a subject, and the administration prevents or reduces tissue damage associated with the treatment, such as cancer radiotherapy and chemotherapy.

In some aspects, a composition or method disclosed herein prevents a tissue damage or reduces the area, volume, or duration of a tissue damage, by inducing migration (e.g., homing) of a stem cell to the tissue site, even after the tissue in the individual has otherwise lost the inherent ability to spontaneously recruit stem cells. In other aspects, administration of a composition and/or cell of the present disclosure triggers a series of other events leading to enhanced resistance to tissue damage, including for example inducing differentiation of stem cells at the tissue site, inducing tissue regeneration at the tissue site, inducing a signaling molecule that triggers tissue regeneration, reversing damage at the site of an initial injury before additional damage is done, and/or reconstructing the microenvironment of neurofibril cells and neurosecretory cells at the tissue site.

For example, myocardial ischemia or infarction can lead to irreversible loss of functional cardiac tissue with possible deterioration of pump function and death. Occlusion of a coronary vessel leads to interruption of the blood supply of the dependent capillary system. Without nutrition and oxygen, cardiomyocytes die and undergo necrosis. An inflammation of the surrounding tissue occurs with invasion of inflammatory cells and phagocytosis of cell debris. A fibrotic scarring occurs, and the former contribution of this part of the heart to the contractile force is lost. Without intervention, the only way for the cardiac muscle to compensate for the tissue loss is hypertrophy of the remaining cardiomyocytes (accumulation of cellular protein and contractile elements inside the cell). Endocrine, metabolic (alcohol) or infectious (virus myocarditis) agents and cancer treatment agents also lead to cell death, with a consequently reduced myocardial function. In some aspects, a composition or method disclosed herein prevents cardiac tissue damage or reduces the area, volume, or duration of cardiac tissue damage. In one aspect, the trace element composition disclosed herein induces migration (e.g., homing) and/or retention of mesenchymal stem cells (e.g., BMSCs) to the cardiac tissue. In one aspect, in cases of myocardial ischemia or infarction, cardiac muscle can compensate for the tissue loss via differentiation of the stem cells to cardiomyocytes, thereby avoiding or reducing cardiac hypertrophy and further cardiac tissue damage.

Delivery of Trace Elements

"Trace element" used herein refers to a chemical element found in small quantities in plants, animals, and/or the earth and which is used by organisms, including plants and animals, and is essential or beneficial, to their physiology. "Trace metals", "trace elements" and "trace compounds" are used interchangeably. While in many cases, the trace element of interest will be present as a complex ion, it includes the various species of ions resulting from introducing the trace element into a cell, tissue, or organism according to the present disclosure. Each of these terms includes the reaction products resulting from their use in a cell, tissue, or organism according to the present disclosure. Suitable trace elements include, but are not limited to, B, Sc, Ti, V, Cr, Mn, Mg, Fe, Co, Ni, Cu, Zn, Ga, Ge, As, Se, Br, Al, Si, P, Y, Zr, Nb, Mo, Tc, Ru, Rh, Rb, Ce, Ag, Pd, Ag, Cd, In, Sn, Sb, F, Te, Au, Pt, Bi, Ir, Os, Re, W, Ta, and Hf. In some embodiments, the trace element is selected from the group consisting of Al, Cd, Rb, Zr, Co, Sn, Cr, Ni, F, Mn, Mg, Mo, Ge, V, Br, I, Ba, Ag, Ti, Se, Cu, and Zn. In some embodiments, the trace element is copper (for example in the form of $CuSO_4$ or $CuCl_2$). In some embodiments, the trace element is in a salt form. In other embodiments, the trace element forms a compound or complex with a protein, peptide, amino acid, or mono-, di-, or polysaccharide. In some embodiments, the trace element forms a compound or complex with one or more polymers. In other embodiments, the trace element is in an organometallic compound, such as a small molecule organometallic compound. In one embodiment, a trace element disclosed herein regulates the transcriptional activity of HIF-1. In one aspect, a trace element, such as copper, is an inducer of HIF-1 transcriptional activity. An inducer of HIF-1 transcriptional activity disclosed herein may comprise one or more metal elements including a trace element.

The trace element in some embodiments can be delivered via microbubbles. The use of ultrasound contrast agents serving also as drug carriers has been described for gas-filled liposomes in U.S. Pat. No. 5,580,575. A quantity of liposomes containing drug is administered into the circulatory system of a patient and monitored using ultrasonic energy at diagnostic levels until the presence of the liposomes is detected in the region of interest. Ultrasonic energy is then applied to the region that is sufficient to rupture the liposomes to release drugs locally for therapeutic purposes. The ultrasonic energy is described in U.S. Pat. No. 5,558,082 to be applied by a transducer that simultaneously applies diagnostic and therapeutic ultrasonic waves from therapeutic transducer elements located centrally to the diagnostic transducer elements.

The use of gas-filled microcapsules (or microbubbles as used herein) to control the delivery of drugs to a region of the body has also been described in U.S. Pat. No. 5,190,766 in which the acoustic resonance frequency of the drug carrier is measured in the region in which the drug is to be released and then the region is irradiated with the appropriate sound wave to control the release of drug. Separate ultrasound transducers are described for the imaging and triggering of drug release in the target region. CN 102302507 B discloses compositions for directional controlled release of trace elements and preparation method and application, including compositions comprising microbubbles.

Exemplary microbubbles used herein include, for example, stabilized microbubbles, sonicated albumin, gas-filled microspheres, gas-filled liposomes, and gas-forming emulsions. A variety of methods have been developed for their manufacture. These methods usually involve spray drying, emulsion, or interfacial polymerization techniques. Typically, the result is a microbubble population having a range of diameters with either a fixed or an arbitrarily variable wall thickness. An ultrasonic contrast agent produced by one methodology, for example, may contain microbubbles where each has a shell wall of the same thickness regardless of its diameter. Alternatively, a different method of production may result in a microbubble population with wall thickness varying even between those microbubbles having the same diameter. Microbubble can be prepared via any of following pharmaceutical methods: ultrasound acoustic-vibration, freeze-drying, spray-drying method, "living"/controlled radical polymerization, precipitation polymerization, suspension polymerization, emulsion polymerization, seed polymerization, dispersion polymerization and precipitation polymerization heterogeneous polymerization system, ion cross-linking, ion emulsified-gel, ion precipitation and chemical cross-linking, emulsion chemical cross-linking, duplicate emulsification-co-cross-linking, thermal cross-linking, coacervation, emulsification-solvent evaporation, or any combination thereof. In some embodiments, the microbubble disclosed herein is a carrier for therapeutics and internally loaded with a drug. The microbubbles are then injected intravenously and allowed to circulate systemically. An ultrasound signal of sufficient energy to rupture the drug-containing microbubbles is applied to a region where the delivery of the drug is desired. The insonating beam destroys the microbubbles and thus releases its payload.

In some embodiments, the microbubble disclosed herein has a controlled fragility, i.e., being rupturable only when exposed to acoustic energy equal to or greater than a predetermined intensity. That is, below this acoustic intensity threshold, substantially all the microbubbles remain intact while above the acoustic intensity threshold the microbubbles rupture. While in the unruptured state, bubble agents can still be seen ultrasonically in the larger blood pool so that the sonographer can position and focus the scanner transducer on the region of interest prior to increasing ultrasound intensity to initiate agent rupture and concomitant delivery of drug. Thus, the agent can be turned-on or turned-off by controlling the intensity of the insonating signal.

In one embodiment, a microbubble can be produced by an emulsion solvent evaporation process. First, two solutions are prepared. One is an aqueous solution containing an appropriate surfactant material which may be an amphiphilic biopolymer such as gelatin, collagen, albumin, or globulins. Viscosity enhancers may additionally be included. This becomes the outer continuous phase of the emulsion system. The second is made from the dissolution of a wall-forming polymer in a mixture of two water immiscible organic liquids. One of the organic liquids is a relatively volatile solvent for the polymer and the other is a relatively non-volatile non-solvent for the polymer. The relatively non-volatile non-solvent is typically a C6-C20 hydrocarbon such as decane, undecane, cyclohexane, cyclooctane and the like. The relatively volatile solvent is typically a C5-C7 ester such as isopropyl acetate. Other polymer solvents, methylene chloride for example, may be used so long as they are miscible with the accompanying non-solvent. Typically about three parts of the organic polymer solution having a concentration of about 0.5 to 10 percent of the polymer is added to one part of the aqueous biomaterial solution having a concentration of about 1 to 20 percent of the biomaterial. The wall forming polymer may be selected for its modulus of elasticity and elongation which define the mechanical properties of the polymer. Preferred polymers useful in the fabrication of drug-carrying microbubble ultrasound contrast agent would be biodegradable polymers such as polyvinylalcohol (PVA), polycaprolactone, polylactic acid, polylactic-polyglycolic acid copolymers, co-polymers of lactides and lactones such as epsilon-caprolactone, delta valerolactone, polyamides, polyhydroxybutyrates, polydioxanones, poly-beta-aminoketones, polyanhydrides, poly-(ortho)esters, and polyamino acids, such as polyglutamic and polyaspartic acids or esters of same, and any suitable combination thereof. The polymer solution (inner organic phase) is added to the aqueous solution (outer phase) with agitation to form an emulsion. A variety of devices can be used to produce the emulsion, e.g. colloid mills, rotor/stator homogenizers, high pressure homogenizers, and sonicating homogenizers. The emulsification step is carried out until the inner phase droplets are in the desired size spectrum. It is this droplet size that will determine the size of the microbubble.

A trace element (for example, copper) could be incorporated into the microbubble agent by a number of techniques. In one method, for example, the drug is dissolved or otherwise incorporated into the organic polymer solution during microbubble fabrication. Alternatively, the drug may be incorporated into the microbubbles through a series of secondary steps where the finished product is reconstituted with a solution containing the drug, the suspended microbubbles are made to flood with the drug containing solution, and the result dried, typically by lyophilization. Finally, the drug may be affixed by chemical means to the surface of the microbubble. Preferred methods of incorporation produce a drug-carrying microbubble that would, upon rupture with insonation, allow ready desolution of the active agent into the blood or other body fluids as required. Those methods which incorporate the drug into the wall structure of the microbubble or provide attachment to the surface may also be useful. In this case it is envisioned that the mechanical properties of the wall would be such that microbubble rupture would result in ultra-small wall fragments which would then carry drug to the local site. Additional disclosures regarding ultrasound triggered drug delivery using hollow microbubbles can be found in U.S. Pat. No. 6,896,659.

In some embodiments, the trace element is delivered via peptide-based nanoparticles comprising copper. In some embodiments, a peptide-based nanoparticle disclosed herein comprises self-assembled peptides (e.g., aromatic dipeptides). The peptides assemble into nanoparticles, such as hydrogel nanoparticles, which can be efficiently utilized, for example, as carriers for delivery of bioactive agents for therapeutic and diagnostic applications. In some aspects, hydrophilic and hydrophobic bioactive substances, small drug molecules, imaging agents such as magnetic or gold nanoparticles, as well as high molecular weight biomolecules such as peptides, proteins, siRNA and DNA, can be delivered via peptide-based nanoparticles according to the present disclosure. In some aspects, the nanoparticles are modified with a biological or synthetic molecule to improve stability, efficiency and/or bioavailability. In certain embodiments, the average diameter of the nanoparticles ranges from 10 nm to 1000 nm, or from 10 nm to 500 nm. In some embodiments, the nanoparticle comprises an ultrastructure with, improved targeting and prolonged in vivo stability, and/or other functionalities. Additional disclosures of peptide-based nanoparticles can be found at WO 2014132262 A1.

A vehicle (such as nanoparticles) containing a trace element can be targeted (e.g., specific chemical interactions such as antigen-antibody binding, etc.) or delivered to the site of injury. In some aspects, treatment of the tissue may be accomplished by non-targeted delivery, for example, by bathing tissue in a nanoparticle material, using a pipette or micropipette to apply a nanoparticle material to tissue, injecting a nanoparticle material into tissue, painting a nanoparticle material onto tissues, or combining nanoparticles with other ingredients such as one or more polymers and/or one or more proteins or combinations thereof. Examples include, but are not limited to albumin, fibrinogen, collagen, elastin, fibronectin, laminin, chitosan, basic fibroblast growth factor, or vascular endothelial cell growth factor, platelet-derived growth factor, epidermal growth factor, or insulin-like growth factor. In other aspects, one or more other chemical entities or moieties to be used in conjunction with the nanoparticles containing a trace element. These species may have a complimentary or additional therapeutic or diagnostic utility. The nanoparticles may be chemically bound to these other components or may be delivered as a simple mixture with them. For example, the nanoparticles may be bound to antibody. The method of repair may involve only one type of nanoparticle or may involve more than one type of nanoparticle. The nanoparticles may contain one or more trace elements.

In one aspect, passive targeting or delivery can be realized via a physical effect inducing release or delivery to the site of injury through a nanoparticle (or microsphere). For example, magnetic albumin microspheres can be synthetized by wrapping both trace elements and magnetic substance into albumin shelled microsphere. After injected into body, magnetic albumin microspheres can be guided to site of injury by outside magnetic field forces. Target sustained release of trace elements can be achieved to increase therapeutic effect and avoid toxic side effect. In another aspect, positive targeting or delivery can be realized by synthesis vehicles with capability of automatic recognizing target organ or tissue cells. For example, antigen-antibody reaction mediated albumin microspheres automatic recognition. Such microsphere surface can be equipped with specific antibody or polypeptide, which has ability of binding with certain cells for target delivery of trace elements. In addition to microsphere, liposome and nanoparticles mediated passive target delivery, and receptoral or polypeptide structure induced positive target delivery can also be used to transport trace elements for reaching the effective concentration. In some embodiments, the trace element is delivered by directly administering the trace element to the site of injury. Other suitable methods include in vitro, ex vivo, or in vivo methods of administration. In some aspects, a trace element composition disclosed herein is orally administered to the site of a tissue injury. In some embodiments, a trace element or a compound containing the trace element (for example, a copper ion, a copper atom, or chelated copper) is absorbed via the digestive track. In one aspect, the absorbed trace element is targeted (by active targeting or passive targeting) to an injury site, and is released locally at the injury site to provide an effective local concentration of the trace element for tissue repair. In some embodiments, the orally delivered trace element forms a compound or complex with a protein, peptide, amino acid, or mono-, di-, or polysaccharide. In some embodiments, the trace element forms a compound or complex with one or more polymers. In other embodiments, the trace element is in an organometallic compound, such as a small molecule organometallic compound.

In some embodiments, the trace element is delivered to an injury site by using a coated implant, stent, or plate, or an implant impregnated with the trace element. In one embodiment, the trace element is delivered to an injury site by slowly releasing the trace element from an intravascular stent attached with the trace element. In other embodiments, the trace element is delivered to the injury site by a positive targeting liposome or an acceptor-donor complex. In some aspects, the trace element is delivered to the injury site using physicotherapeutics, ultrasound, iontophoresis, ultrasound penetration enhancement, electroporation, and/or sponge application. Application of the composition and/or cells to the injury site may be topical (e.g., through the skin), may be to some location at the injured tissue that is interior to the body surface, or both. For example, the trace element may be delivered via iontophoresis through the blood vessel, an endothelial cell layer, or other interior tissues, to the injury site to provide an effective local concentration of the trace element for tissue repair.

In one aspect, disclosed herein is an applicator for delivering a trace element composition and/or cells disclosed herein to an injury site. The applicator may be any appropriate device for delivering compositions of the variety disclosed herein. The applicator may be configured for contacting the body surface with a composition by spraying, dripping, painting, propelling, misting, atomizing, or injecting, or may be configured for applying the composition and/or cells by any combination of such methods. The application of the composition and/or cells to the injury site may be topical, may be to some location at the injured tissue that is interior to the body surface, or both, and the applicator may be configured accordingly. In some embodiments, applicator is configured to deliver a composition that is a fluid onto the site of injury. Nozzles for dripping, misting, atomizing, or stream-spraying (e.g., in a flat or round stream) a fluid are well known in the art. The applicator may be configured for "painting" a composition onto the body surface, for example, as a brush, roller, or roller ball. Applicators for injecting a composition at the injury site include needles, such as nano- or micro-injection needles. The applicator may be configured for applying a composition by iontophoresis, ultrasound penetration enhancement, electroporation, sponge application, or by any other suitable process. Preferably, the applicator is configured so that the delivery of the composition to the location of the injury site is spatially precise within a therapeutically acceptable margin of error.

In some aspects, a trace element composition disclosed herein is orally administered to the site of a tissue injury. In some embodiments, a trace element or a compound containing the trace element (for example, a copper ion, a copper atom, or chelated copper) is absorbed via the digestive track. In one aspect, the absorbed trace element is targeted (by active targeting or passive targeting) to an injury site to provide an effective local concentration of the trace element for tissue repair. In some embodiments, the orally delivered trace element forms a compound or complex with a protein, peptide, amino acid, or mono-, di-, or polysaccharide. In some embodiments, the trace element forms a compound or complex with one or more polymers. In other embodiments, the trace element is in an organometallic compound, such as a small molecule organometallic compound.

When used in vivo for therapy, the trace element composition and/or cells are administered to the subject in effective amounts (i.e., amounts that have desired therapeutic and/or prophylactic effect). The dose and dosage regimen will depend upon the degree of the injury in the subject, the characteristics of the particular trace element composition and/or cells used, e.g., its therapeutic index, the subject, and the subject's history.

The effective amount may be determined during pre-clinical trials and clinical trials by methods familiar to physicians and clinicians. An effective amount of a trace element composition and/or cells useful in the methods may be administered to a mammal in need thereof by any of a number of well-known methods for administering pharmaceutical compounds, either systemically or locally.

Delivery of Trace Elements Directly into the Site of Injury

In one aspect, the trace elements are delivered directly into the site of injury, either via direct injection into the injured tissue, or via a coated implant placed in physical contact with the site of the injury. This allows the trace element to stay at the delivery site for a long period of time, creating a gradient of the trace element with the highest concentration at the site of injury. Such gradient of the trace element allows growth of blood vessels towards the site of injury, thus facilitating the regeneration of the blood microvessel environment at the site of injury and consequently regeneration of the tissue. In one embodiment, a trace element disclosed herein regulates the transcriptional activity of HIF-1. In one aspect, a trace element, such as copper, is an inducer of HIF-1 transcriptional activity. An inducer of HIF-1 transcriptional activity disclosed herein may comprise one or more metal elements including a trace element.

In some embodiments, direct delivery of a trace element into the injured tissue avoids or reduces adverse side effects associated with systemic administration. In certain aspects, direct delivery at the injury site avoids systemic toxicity associated with the drug or agent and/or induction of systemic inflammatory responses such as a cytokine storm.

In some embodiments, a trace element is delivered to an injury site by using a coated implant, stent, or plate, or an implant impregnated with the trace element. In some aspects, direct delivery to the site of injury comprises localized delivery to a treatment site inside a blood vessel or tissue. Suitable delivery systems include but are not limited to dual balloon delivery systems that have proximal and distal balloons that are simultaneously inflated to isolate a treatment space within an arterial lumen. In this case, a catheter extends between the two balloons to locally deliver a therapeutic agent. Other balloon-based localized delivery systems include porous balloon systems, hydrogel-coated balloons and porous balloons that have an interior metallic stent. Other systems include locally placed drug-loaded coated metallic stents and drug-filled polymer stents. Wilensky et al., Methods and Devices for Local Drag Delivery in Coronary and Peripheral Arteries, Trend Cardiovasc Med, vol. 3 (1993).

In one aspect, sustained delivery of a trace element at the injury site provides relatively small quantities of the agent administered over an extended period of time to the injured tissue. In one embodiment, the extended treatment achieves results not available by acute treatment with high doses of the agent, with smaller and less toxic doses. In one aspect, the sustained delivery of a trace element at the injury site release the agent for longer than about 12 hours, about one day, about two days, about one week, about two weeks, about one month, about two months, about six months, about nine months, about one year, about one year and a half, or about two years.

In some embodiments, a sustained delivery composition disclosed herein includes long-acting injectables (e.g., oil-based injections, injectable suspensions, injectable microspheres, and injectable in situ systems) containing a trace element, agents and polymers for depot injections, commercially available depot injections, and injectable sustained-release delivery systems. In certain embodiments, a sustained delivery composition disclosed herein comprises a polymeric matrix from which an agent is released by diffusion and/or degradation of the polymer matrix. Hence, the release pattern of the agent is principally determined by the polymer matrix, as well as by the percent loading and method of manufacture. In some embodiments, the sustained release preparations use a biodegradable polymer. In this case, the sustained release preparations do not require the surgical removal of the preparations from the subject. Typically, such preparations are slowly degraded and absorbed by the patient's body, and ultimately disposed of along with other soluble metabolic waste products.

In one aspect, a polymeric injectable depot system is used to deliver an in-situ-forming implant containing a trace element at the site of injury. In situ-forming implant systems are typically made of biodegradable products, which can be injected via a syringe into the body, and once injected, congeal to form a solid biodegradable implant. In some embodiments, the implant is formed by thermoplastic pastes, in situ cross-linked polymers, in situ polymer precipitation, thermally induced gelling, or in situ solidifying organogels. The mechanism of depot formation of thermoplastic pastes is to form a semisolid upon cooling to body temperature after injection into the body in the molten form. Cross-linked polymer networks can be achieved in situ in various ways, forming solid polymer systems or gels. Methods for in situ cross-linked systems include free radical reactions, usually initiated by heat or absorption of photons, or ionic interactions between small cations and polymer anions. In situ formings can be produced by causing polymer precipitation from solution. A water-insoluble and biodegradable polymer is solubilized in a biocompatible organic solvent to which a drug is added which forms a solution or suspension after mixing. When this formulation is injected into the body, the water-miscible organic solvent dissipates and water penetrates into the organic phase. This leads to phase separation and precipitation of the polymer forming a depot at the site of injection. Thermally induced gelling systems show thermo-reversible sol/gel transitions and are characterized by a lower critical solution temperature. They are liquid at room temperature and produce a gel at and above the lower critical solution temperature. In situ solidifying organogels comprises water-insoluble amphiphilic lipids, which swell in water and form various types of lyotropic liquid crystals.

In some embodiments, a sustained release composition disclosed herein comprises a biodegradable polymer for controlled delivery of a trace element. Suitable biodegradable polymers typically include polylactides (PLA), polyglycolides (PGA), poly(lactide-co-glycolide) (PLGA), poly(ε-caprolactone) (PCL), polyglyconate, polyanhydrides, polyorthoesters, poly(dioxanone), and polyalkylcyanoacrylates. In some embodiments, the sustained release composition comprises injectable biodegradable microspheres such as PLGA microspheres, PCL microspheres, polyanhydride microspheres, polyorthoesters microspheres, and polyalkylcyanoacrylate microspheres.

In some embodiments, the direct delivery is effected by injection of nanoparticle materials containing copper (or other trace elements) to the site of injury. In some aspects, a nanoparticle material disclosed herein comprises a particle having dimensions of from about 1 to about 5,000 nanometers. In some aspects, the dimensions of the nanoparticles can vary widely, with largest dimensions (e.g., the diameter for a sphere, the width for a plate, the length for a rod, etc.) ranging anywhere from 1 to 1,000 nm, and smallest dimensions (e.g., the diameter of a rod, the thickness of a plate, etc.) ranging anywhere from 0.1 to 100 nm.

The nanoparticles may have any shape or morphology. For example, they may be metal colloids such as gold colloid or silver colloid. The nanoparticles may be fullerenes which are available in both nanosphere and nanotube structures. In some embodiments, the nanoparticle may have a core/shell structure, such as a nanoshell. In some embodiments, the nanoparticles can be spheres, flat or bent plates, and linear or bent elongate particles which can be any cross section including circular, annular, polygonal, irregular, and so forth (e.g., elongated cylinders, tubes, columnar shapes with polygonal cross-sections, ribbon-shaped particles, etc.), as well as other regular or irregular geometries.

The nanoparticle materials containing a trace element can be targeted (e.g., specific chemical interactions such as antigen-antibody binding, etc.) or directly delivered to the site of injury. In some aspects, treatment of the tissue surfaces may be accomplished by non-targeted delivery, for example, by bathing tissue in a nanoparticle material, using a pipette or micropipette to apply a nanoparticle material to tissue, injecting a nanoparticle material into tissue, painting a nanoparticle material onto tissues, or combining nanoparticles with other ingredients such as one or more polymers and/or one or more proteins or combinations thereof. Examples include, but are not limited to albumin, fibrinogen, collagen, elastin, fibronectin, laminin, chitosan, basic fibroblast growth factor, or vascular endothelial cell growth factor, platelet-derived growth factor, epidermal growth factor, or insulin-like growth factor. In other aspects, one or more other chemical entities or moieties to be used in conjunction with the nanoparticles containing a trace element. These species may have a complimentary or additional therapeutic or diagnostic utility. The nanoparticles may be chemically bound to these other components or may be delivered as a simple mixture with them. For example, the nanoparticles may be bound to antibody. The method of repair may involve only one type of nanoparticle or may involve more than one type of nanoparticle. The nanoparticles may contain one or more trace elements.

Polymers from which the nanoparticles can be formed include polymers which are natural and synthetic, biodegradable or non-biodegradable, homopolymeric or copolymeric, thermoplastic or non-thermoplastic, and so forth. Suitable polymers for forming the nanoparticles can be selected, for example, from the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-maleic anhydride copolymers, styrene-butadiene copolymers, styrene-ethylene-butylene copolymers (e.g., a polystyrene-polyethylene/butylene-polystyrene (SEBS) copolymer, styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide, epsilon-caprolactone, glycolide (including glycolic acid), hydroxybutyrate, hydroxyvalerate, para-dioxanone, trimethylene carbonate (and its alkyl derivatives); polyether polymers and copolymers including polyarylethers such as polyphenylene ethers, polyether ketones, polyether ether ketones; polyphenylene sulfides; polyisocyanates; polyolefin polymers and copolymers; polyolefin elastomers (e.g., santoprene), ethylene propylene diene monomer (EPDM) rubbers, fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-poly lactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and further copolymers of the above.

In other embodiments, the nanoparticles can be formed from one or more metals, for example, selected from the following: substantially pure metals, such as silver, gold, platinum, palladium, iridium, osmium, rhodium, titanium, tungsten, and ruthenium, as well as metal alloys such as cobalt-chromium alloys, nickel-titanium alloys, iron-chromium alloys, cobalt-chromium-iron alloys, and nickel-chromium alloys, among others. In some other aspects, the nanoparticles can be formed from a trace element as disclosed herein, and may be used to deliver the same or a different trace element directly to the site of injury.

In some embodiments, the nanoparticles can be formed from one or more suitable non-metallic inorganic materials, for example, selected from the following: calcium phosphate ceramics (e.g., hydroxyapatite); calcium-phosphate glasses, sometimes referred to as glass ceramics (e.g., bioglass); metal oxides, including non-transition metal oxides (e.g., oxides of metals from groups 13, 14 and 15 of the periodic table, including, for example, aluminum oxide) and transition metal oxides (e.g., oxides of metals from groups 3, 4, 5, 6, 7, 8, 9, 10, 11 and 12 of the periodic table, including, for example, oxides of titanium, zirconium, hafnium, tantalum, molybdenum, tungsten, rhenium, iridium, and so forth); carbon based materials such as pure and doped carbon (e.g., fullerenes, carbon nanofibers, single-wall, so-called "few-wall" and multi-wall carbon nanotubes), silicon carbides and carbon nitrides; silica; synthetic or natural silicates including aluminum silicate, monomeric silicates such as polyhedral oligomeric silsequioxanes (POSS), including various functionalized POSS and polymerized POSS, and phyllosilicates including clays and micas (which may optionally be intercalated and/or exfoliated) such as montmorillonite, hectorite, hydrotalcite, vermiculite and laponite.

In some embodiments, a nanoparticle material disclosed herein comprises one or more polymers, one or more metals or alloys, and/or one or more suitable non-metallic inorganic materials.

In particular embodiments, a range of types of copper-containing compound can be used for localized delivery directly to an injury site. Examples of suitable copper ion-containing solutions are copper (I) chloride, copper (II) chloride, copper acetate, and copper sulphate solutions. In other embodiments, suitable zinc-containing solutions are used, such as solutions of zinc chloride, zinc acetate, and zinc sulphate. In other embodiments, copper or zinc forms a compound or complex with a protein, peptide, amino acid, mono-, di-, or polysaccharide, one or more polymers, or a small molecule, and the compound or complex is used for direct localized delivery at the injury site. In some embodiments, an organometallic compound containing a trace element is used for direct localized delivery at the injury site.

In some embodiments, the concentration of copper ions in the copper composition used for localized delivery directly to an injury site is from about 5 µM to about 10 µM, about 10 µM to about 20 µM, about 20 µM to about 40 µM, about 40 µM to about 60 µM, about 60 µM to about 80 µM, about 80 µM to about 100 µM, about 100 µM to about 200 µM, about 200 µM to about 400 µM, about 400 µM to about 600 µM, about 600 µM to about 800 µM, about 800 µM to about 1 mM, about 1 mM to about 5 mM, about 5 mM to about 10 mM, about 10 mM to about 20 mM, about 20 mM to about 40 mM, or about 40 mM to about 60 mM. Suitable concentrations of zinc ions will be of the same order as the concentrations of the copper compositions described above. The concentration of a trace element may be determined during pre-clinical trials and clinical trials by methods familiar to physicians and clinicians.

In another embodiment, the trace element is injected to the injury site, for example, by direct percutaneous puncture, by an interventional catheter, or by intravertebral injection. In some embodiments, the trace element is delivered directly to an injury site by using a coated implant, stent, or plate, or an implant impregnated with the trace element. In one embodiment, the trace element is delivered directly to an injury site by slowly releasing the trace element from an intravascular stent attached with the trace element. In one aspect, disclosed herein is an applicator for delivering a trace element composition and/or cells disclosed herein directly to an injury site.

Tissue Injury and Associated Diseases

"Tissue injury" described herein refers to an injury of a tissue, including for example cardiovascular, liver, brain, skeletal muscle, and the like. In some embodiments, the tissue injury is cardiovascular ischemia. In some embodiments, the tissue injury is liver fibrosis. In some embodiments, the tissue injury is brain stroke. In some embodiments, the tissue injury is low limb ischemia. In some embodiments, the tissue injury is associated with diabetes, diabetic foot ulcers, necrotizing enterocolitis, ulcerative colitis, Crohn's disease, inflammatory bowel disease, restenosis (post-angioplasty or stent implantation), incisional wounding, excisional wounding, surgery, accidental trauma, pressure ulcer, stasis ulcer, tendon rupture, vocal fold phonotrauma, otitis media, or pancreatitis.

In some embodiments, the tissue injury is associated with diabetes. In some aspects, the tissue injury is associated with diabetic foot. Diabetic foot typically is caused by both vascular and neurologic complications of diabetes, in combination with persistent opportunistic infections and deficient wound healing. In one aspect, the tissue injury is a diabetic foot ulcer. In other aspects, the tissue injury is a diabetic skin ulcer.

The methods described herein are therefore generally applicable to many diseases that involve tissue injury. These include, but are not limited to: myocardial infarction, cardiomyopathy, aneurysm, angina, aortic stenosis, aortitis, arrhythmias, arteriosclerosis, arteritis, asymmetric septal hypertrophy (ASH), atherosclerosis, atrial fibrillation and flutter, bacterial endocarditis, Barlow's Syndrome (mitral valve prolapse), bradycardia, Buerger's Disease (thromboangiitis obliterans), cardiomegaly, carditis, carotid artery disease, coarctation of the aorta, congenital heart defects, congestive heart failure, coronary artery disease, Eisenmenger's Syndrome, embolism, endocarditis, erythromelalgia, fibrillation, fibromuscular dysplasia, heart block, heart murmur, hypertension, hypotension, idiopathic infantile arterial calcification, Kawasaki Disease (mucocutaneous lymph node syndrome, mucocutaneous lymph node disease, infantile polyarteritis), metabolic syndrome, microvascular angina, myocarditis, paroxysmal atrial tachycardia (PAT), periarteritis nodosa (polyarteritis, polyarteritis nodosa), pericarditis, peripheral vascular disease, critical limb ischemia, phlebitis, pulmonary valve stenosis (pulmonic stenosis), Raynaud's Disease, renal artery stenosis, renovascular hypertension, rheumatic heart disease, diabetic vasculopathy, septal defects, silent ischemia, syndrome X, tachycardia, Takayasu's Arteritis, Tetralogy of Fallot, transposition of the great vessels, tricuspid atresia, truncus arteriosus, valvular heart disease, varicose ulcers, varicose veins, vasculitis, ventricular septal defect, Wolff-Parkinson-White Syndrome, endocardial cushion defect, acute rheumatic fever, acute rheumatic pericarditis, acute rheumatic endocarditis, acute rheumatic myocarditis, chronic rheumatic heart diseases, diseases of the mitral valve, mitral stenosis, rheumatic mitral insufficiency, diseases of aortic valve, diseases of other endocardial structures, ischemic heart disease (acute and subacute), angina pectoris, acute pulmonary heart disease, pulmonary embolism, chronic pulmonary heart disease, kyphoscoliotic heart disease, myocarditis, endocarditis, endomyocardial fibrosis, endocardial fibroelastosis, atrioventricular block, cardiac dysrhythmias, myocardial degeneration, cerebrovascular disease, a disease of arteries, arterioles and capillaries, or a disease of veins and lymphatic vessels; an acquired brain injury, traumatic brain injury, stroke (including ischemic, intracerebral hemorrhagic, subarchnoidal hemorrhagic), anoxic injuries, metabolic disorders, encephalitis, and brain injuries due to infection. In certain embodiments, diseases that involve tissue injury include systemic sarcoidosis, a cutaneous disease or condition, Lofgren's syndrome, a pulmonary disease or condition, a cardiac disease or condition, an ocular disease or condition, a hepatic disease or condition, a musculoskeletal disease or condition, and a renal disease or condition. The present application thus also comprises treatment of any of the diseases using methods described herein.

Kits, Compositions, and Articles of Manufacture

In another embodiment, provided herein are kits comprising at least one stem cell and/or a trace element disclosed herein, and a therapeutic cell composition thereof, which can be prepared in a pharmaceutically acceptable form, for example by mixing with a pharmaceutically acceptable carrier, and an applicator, along with instructions for use. The kits can comprise a container separate from remaining kit contents. In certain embodiments, the compositions and kits can comprise one or more of a BMSC, a trace element, an inducer of stem cells, and an additional therapeutic agent as disclosed herein.

In certain embodiments, the kits comprise one or more components that facilitate delivery of the BMSC, the trace element, the inducer of stem cells, and/or the additional therapeutic agent to the individual. For example, in certain embodiments, the kit comprises components that facilitate intralesional delivery of BMSC and/or trace element and/or inducer of stem cells to the individual. In such embodiments, the kit can comprise, e.g., syringes and needles suitable for delivery of cells to the individual, and the like. In such embodiments, the stem cell or trace element or inducer of stem cells may be contained in the kit in a bag, or in one or more vials. In certain other embodiments, the kit comprises components that facilitate intravenous or intra-arterial delivery of the stem cell or trace element or inducer of stem cells to the individual. In such embodiments, the stem cell or trace element or inducer of stem cells may be contained, e.g., within a bottle or bag (for example, a blood bag or similar bag able to contain up to about 1.5 L solution comprising the cells), and the kit additionally comprises tubing and needles suitable for the delivery of the stem cell or trace element or inducer of stem cells to the individual.

Additionally, the kit may comprise one or more compounds that reduce pain or inflammation in the individual (e.g., an analgesic, steroidal or non-steroidal anti-inflammatory compound, or the like. The kit may also comprise an antibacterial or antiviral compound (e.g., one or more antibiotics), a compound to reduce anxiety in the individual, a compound that reduces an immune response in the individual (e.g., cyclosporine A), and/or an antihistamine (diphenhydramine, loratadine, desloratadine, quetiapine, fexofenadine, cetirizine, promethazine, chlorepheniramine, levocetirizine, cimetidine, famotidine, ranitidine, nizatidine, roxatidine, lafutidine, or the like).

Additionally, the kit can comprise disposables, e.g., sterile wipes, disposable paper goods, gloves, or the like, which facilitate preparation of the individual for delivery, or which reduce the likelihood of infection in the individual as a result of the administration of the stem cell and/or trace element and/or inducer of stem cells.

The following non-limiting examples further illustrate the compositions and methods of the present invention. Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

Example 1

Use of Ultrasound Mediated Cu-Albumin Microbubble to Improve BMSCs Homing in Chronic Ischemic Heart To orient the copper supplement, this experiment used Cu-albumin-microbubble. Located and irradiated with ultrasound, copper was released from the bubble to the target area of heart, increasing copper concentration in the ischemic region. Pilot experiments showed that the oriented supplement of copper to the heart relieved the symptoms of chronic cardiac ischemia. Besides, vitro BMSCs culture methods have been well established, and BMSCs are suitable tracking cells for they are typical homing stem cells. New Zealand white rabbits are one of the favorable model animals in the area of cardiac research. As well, they are ideal for the tracking of homing autologous BMSCs. BMSCs were cultured and labeled, then injected into the myocardial infarcted rabbits. With treatment of Cu-albumin-microbubble, the re-homing of BMSCs to the chronic ischemic heart was observed through the labeled fluorescence. In addition, the specific blocker of SDF-1/CXCR4 axis, AMD3100, was used in this experiment to search the mechanisms of BMSCs homing during cardiac ischemia and microbubble treatment, expounding the pathogenesis of cardiac infarction and providing theoretical foundations for new therapies of cardiac infarction.

Methods:

1. Experimental MI (Myocardial Infarction) and Treatment of Cu-Albumin Microbubble (1) Adult male New Zealand white rabbits were preoperative fasted for 12 hours, and the operation room was sterilized by overnight ultraviolet radiation before the surgery. (2) Rabbits were anesthetized with 3 ml/kg chloral hydrate by intraperitoneal administration, and then placed on the operation table in the supine position. Hairs covering chest and limbs at electrode attachment site were shaved. The surgical area was scrubbed with povidone-iodine for 3 consecutive times. Lidocaine was injected into the subcutaneous area around the incision site. (3) Electrodes were attached to the limbs and ECG (electrocardiogram) was recorded 30 minutes before and after the surgery. (4) The rabbits were subjected to a median sternotomy. The skin was cut and the s.c. tissue and the muscular was dissected. Afterwards, the sternum was retracted and the pleuron was dissected, the pleural space was opened and so the pericardium was exposed. (5) After gently incision of the pericardium, the heart was exposed and the left circumflex branch (LC) was ligated. The ligation site was at the level 75 of the LC (the epicardial end of the LC was defined as level zero; the origin of the LC was defined as level 100). Monitoring the heart condition and respiration until the ligation was done. (6) Color changes of the anterior ventricular wall, the difference of left ventricular wall motion, and alterations including ST segment recorded by electrodes II, III, and aVF in ECG was monitored for 2 minutes to ensure that the ligation was successful. (7) Monitoring the heart condition intensively for 10 minutes, so that when dysrhythmias or abnormal respiration was identified the ligation could be released and cardiopulmonary resuscitation could be administrated if necessary. The chest was closed when cardiac hemodynamic and vital signs become stable. If the pleura were damaged during the surgery, the chest would be closed immediately and aerothorax was prevented by air extracting. (8) The incision site was cleaned in a sterile manner and the rabbits were then allowed to recover. The rabbits were given 400000 units of penicillin for 3 days to avoid infection. (9) Survived rabbits were divided into 3 groups: Acute (≤1 month after the surgery); Chronic (6 months after the surgery); Chronic & Microbubble (6 months after the surgery and treated with Cu-albumin microbubble). Cu-albumin-microbubble was administrated i.v. through ear vein 6 months after the experimental MI surgery. Microbubbles (5 ml/rabbit/treatment) were ultrasound radiated at the left ventricle of the heart by Color Doppler Diagnostic Ultrasound System (frequency: 1.3 MHz, energy: 90~100%, mechanical index: 1.1~1.2, radiation time: 20 minutes/treatment (5 seconds radiation-5 seconds interval)). Every rabbit was treated 3 times; the treatment was administrated 2-3 days a time, and all the 3 times of treating for one rabbit were conducted within one week.

2. Isolation and Culture of Rabbit BMSCs (1) Adult male New Zealand white rabbits were preoperative fasted for 12 hours, and the operation room was sterilized by overnight ultraviolet radiation before the surgery. (2) Rabbits were anesthetized with 3 ml/kg chloral hydrate by intraperitoneal administration, and then placed on the operation table in the supine position. Hairs covering limbs at aspiration site were shaved. The surgical area was scrubbed with povidone-iodine for 3 consecutive times, followed by 75% alcohol scrubbing for deiodination. The aspiration site was exposed while the area around was covered by operation towels. (3) Bone biopsy needle(s) and syringe(s) were heparinized in sterile manner. (4) One or both femurs of the donor rabbits were aspirated using the heparinized needle(s) and the fringe(s), 1-2 ml bone marrow aspirates were taken per aspiration. (5) The aspirates were immediately transported into a 15-ml tube containing 4-5 ml of Dulbecco's modified Eagle's medium (L-DMEM). The sample was blended with the DMEM by gently swinging of the tube for prevention of coagulation. (6) The blending was layered over an equal volume of 1.077 g/ml Percoll solution in another 15-ml conical tube. The solution should be kept at room temperature before the isolation and the blending should be layered gently on the solution. (7) The blending-solution was then centrifuged at 400×g for 15 min at room temperature. (8) The buffy layer (mono nuclear cells) at gradient interface was collected, rinsed twice by DMEM with centrifugation at 300×g. Cells were seeded in L-DMEM supplemented with 12% FBS at 37° C. in a humidified atmosphere of 5% $CO_2$. (9) The first media change was conducted 3 days after the seeding. Afterwards the culture media were changed every 2 or 3 days. Media change could be conducted in half or whole medium change manner. And the concentration of FBS in medium was modulated according to the condition of the cells. Non-adherent cells were discarded with the media change. At 80-90% confluence, the MSCs were digested with 0.25% trypsin-EDTA and passaged. Cells were cultured to the number of $8\text{-}10 \times 10^6$.

3. Labelling of Rabbit BMSCs (1) When proliferated into approximately $8\text{-}10 \times 10^6$, BMSCs were harvested and washed using L-DMEM (with no serum) for 2 times, the latter of which requires centrifugation at 400×g to pack the cells. (2) Collected BMSCs were firstly labeled by pkH26, following the manufacturers' instructions. In brief, the DMEM was removed to the greatest extent from packed cells. The cells were then suspended in one part of the Dilute-C (equally divided into 2 parts) at the concentration of $1 \times 10^7$ cells/2 ml. The dye was blended in another part of the Dilute-C and added into the cell suspension (concentration of the dye: 5 μl/1× $10^7$ cells). After that, sufficient blending was done and the incubation was conducted in room temperature for 5 minutes, with gently swinging for 1 or 2 times in the process. Equal volume of serum was then added into the blending, incubation for 1 minute to stop the labeling. Cells were then washed by 5 ml DMEM (with serum) with centrifugation at 400×g for 10 minutes at room temperature. Afterwards, cells were washed for 2 or 3 times with DMEM, and seeded in L-DMEM supplemented with 10% FBS at 37° C. in a humidified atmosphere of 5% $CO_2$ overnight. Successfully labeled cells were pink to red if observed by naked eyes. (3) The pKH26 labeled BMSCs were then tested through confocal laser scanning microscopy, before which the medium was changed and dead cells were discarded. The label ratio of the cells was considered to be qualified only when it was higher than 90%, or the step (2) should be repeated. (4) Before the labeling process, working solutions of Dio(3) and Hoechst were prepared: Dio(3) was diluted in distilled water to the concentration of 1 μg/μl, filtered to sterilize and stored at −20° C.; Hoechst was diluted in dimethylsulfoxide to the concentration of 1 μg/μl and stored at −20° C. (5) After the red fluorescence (pKH26) test, Dio(3) (10 ug/10 ml) and Hoechst (10 ug/10 ml) was added into the medium of the qualified pKH26 labeled BMSCs, and the cells were incubated overnight. (6) The final successful labeling was considered as strong red & green and weak blue fluorescent signals. (7) Labeled cells were then imaged and analysis of the labeling ratio of red, green fluorescence was done. Blue fluorescent signals were observed as the nucleus and the labeling ratio was calculated as: No. of red or green fluorescent cells/No. of blue fluorescent cells in a random 200× field. (8) For the AMD3100 treated group, sterile AMD3100 (final concentration: $1 \times 10^7$ ng/ml) was added into the labeled cells and incubated overnight. When the incubation was done, the cells were digested, washed, suspended in 1 to 2 ml L-DMEM (with no serum) before use. As for other groups, successfully labeled cells were digested, washed, suspended in 1 to 2 ml L-DMEM (with no serum) before use. The prepared BMSCs were injected into the same donor rabbit through the ear vein.

4. Tracking of Homing Rabbit BMSCs During Cardiac Infarction and After Treatment of Cu-Albumin-Microbubble 4.1 Tracking of homing rabbit BMSCs during acute cardiac infarction, chronic cardiac ischemia and chronic cardiac ischemia with treatment of Cu-albumin-microbubble (1) Acute (≤1 month after the MI surgery, n=3); Chronic (6 months after the MI surgery, n=3); Chronic & Microbubble (6 months after the MI surgery and treated with Cu-albumin microbubble, n=5). (2) BMSCs were isolated and cultured 1 month before (for group Acute) or 4-5 months after (other groups Chronic and Chronic & Microbubble) the MI surgery, and labeled with pKH26, Dio(3), and Hoechst before use. (3) Prepared BMSCs ($1\text{-}9 \times 10^6$ cells/rabbit) were injected through the ear vein at 2 weeks (Acute) or 6 months (Chronic) after the MI surgery into the donor rabbits. Hearts were harvested 24 hours after the cell injection. For group Chronic & Microbubble, the microbubble treatments were conducted 6 months after the MI surgery. Prepared BMSCs were injected into the donor rabbits after 3 treatments. Hearts were harvested 24 hours after the cell injection. Each harvested heart was divided into 4 parts with similar thickness from apex to base along the long axis. Every part was then frozen sliced (5 slices/part), also from apex to base along the long axis, and observed using confocal laser scanning microscopy. Images of homing were captured using Nikon DXM1200/NIS-Elements. Slices were afterwards fixed and prepared for pathology analysis. (4) Images were analyzed by Image-Pro Plus 6.0. IOD values and fluorescent areas (by pixel) of red fluorescence of each image were calculated. Then the sums of IOD values and fluorescent areas for each heart were calculated. The statics were processed as: Sum of IOD (or fluorescent areas)/Number of fluorescent slices.

4.2 Mechanisms of BMSCs Homing Induced by Cu-Albumin-Microbubble (1) Rabbits were divided into 3 groups: Chronic (6 months after the MI surgery, n=3), Chronic & Microbubble (6 months after the MI surgery and treated with Cu-albumin microbubble, n=5), Chronic & Microbubble+AMD3100 (6 months after the MI surgery, treated with copper-Microbubble and BMSCs treated with AMD3100, n=3). (2) BMSCs were isolated and cultured 4-5 months after the MI surgery, and labeled with pKH26, Dio(3), and Hoechst before use. (3) Prepared BMSCs were injected through the ear vein into the donor rabbits at 6 months after the MI surgery with (Chronic & Microbubble) or without microbubble treated (Chronic). Hearts were harvested 24 hours after the cell injection. For group Chronic & Microbubble+AMD3100, the microbubble treatments were conducted 6 months after the MI surgery. Fluorescent labeled and AMD3100 treated BMSCs were injected into the donor rabbits after 3 treatments. Hearts were harvested 24 hours after the cell injection. Harvested hearts were frozen sliced. Slices were observed and recorded using confocal laser scanning microscopy, imaging system: Nikon DXM1200/NIS-Elements. Slices were afterwards fixed and prepared for pathology analysis. (4) Images were analyzed by Image-Pro Plus 6.0. IOD values and fluorescent areas (by pixel) of red fluorescence of each image were calculated. Then the sums of IOD values and fluorescent areas for each heart were calculated. The statics were processed as: Sum of IOD (or fluorescent areas)/Number of fluorescent slices.

5. Pathology Analysis

Overdose of chloral hydrate was injected i.v. to sacrifice the rabbit. Hearts were then harvested and washed using NS (normal saline). Afterwards, the saline was removed thoroughly and the heart was frozen sliced. Confocal observed slices were dried, fixed in 4% formaldehyde solution. The slices were then dehydrated and stained with HE: (1) Dewax the slices with Xylene, wash the slices with Alcohol of decreased gradient concentrations and finally water: Xylene (I) 5 minutes→Xylene (II) 5 minutes→100% Alcohol 2 minutes→95% Alcohol 1 minutes→80% Alcohol 1 minutes→75% Alcohol 1 minutes→distilled Water 2 minutes; (2) Stain the slices in Hematoxylin for 5 minutes, followed by distilled water washing; (3) distilled Water washing, 1% Acidic Alcohol for 30 seconds; (4) Soak in running water for 15 minutes or warm water (about 50° C.) for 5 minutes; (5) Stain the slices in alcohol-soluble-eosin for 2 minutes; (6) Dehydration, transparency, and enveloping of the slices: 95% Alcohol (I) 1 minutes→95% Alcohol (II) 1 minutes→100% Alcohol (I) 1 minutes→100% Alcohol (II) 1 minutes→Xylene (I) 1 minutes→Xylene (II) 1 minutes→envelop with neutral resin.

6. Statistical Analysis

SPSS14.0 (SPSS, Chicago, Ill.) was used to analyze the data. IOD values and fluorescent area were expressed as medium. Differences between groups were tested by sum of ranks, $\alpha=0.05$. The labeling ratios were expressed as mean±SD ($\bar{X}$±SD). Differences between groups were tested by Independent-Samples t-tests. Statistical significance was assumed when P values were <0.05.

Results:

During the MI surgery, color changes of the anterior ventricular wall, slowdown of myocardial motion (involving left ventricular wall, lateral wall and apex), and lifted or lowered ST segment recorded by electrodes II, III, and aVF was observed.

Bone marrow aspirates were taken and isolated through density gradient centrifugation. The buffy layer (mono nuclear cells) was collected, cultured and passaged. Nonadherent cells were discarded with the media change and adherent cells proliferated, in which way BMSCs were enriched. The adherent cells developed clonal growth 3-5 days after the seeding. Both polyhedral and spindle cells were observed in the colonies. Polyhedral cells were dominant within the first week after the seeding, however gradually substituted by spindle cells. When the colonies were big and dense (normally happened in 1-2 weeks after the seeding), the cells could be passaged. After passage, spindle cells became dominant cells.

Fluorescent labeling was conducted when cells proliferated to approximately $8-10\times10^6$. For that digestion and centrifugation was required in the process of pKH26 labeling, pKH26 labeling usually caused cell death to a part of cells. Thus Dio(3) and Hoechst labeling was processed after pKH26, letting the successfully pKH26 labeled and living cells adherent and survive. Dio(3) and Hoechst was added into the medium of the qualified pKH26 labeled BMSCs, and the cells were incubated overnight. Only when labeling ratio is would the cells considered successfully labeled and suitable for the tracking experiments.

Both pKH26 and Dio(3) are liposoluble dyes, the labeling mechanisms of which are insertion of fluorophores into the membrane. The labeling signals of these two dyes were similar. Labeled cells were seen as uniformly red or green doted in the membrane. Observation has shown that, for one cell, some may labeled with stronger pKH26 signals, but some with stronger Dio(3) signals. A very few cells could not be labeled by either Dio(3) or pKH26.

From the results that observed from the homing of BMSCs during myocardial infarction and Cu-albumin-microbubble treatment, infarct area was unusually within the $1^{st}$, $2^{nd}$ and $3^{rd}$ part of the heart. The infarct area involves apex and most of the left ventricle wall for that experimental MI was achieved through ligation of LC. Harvested hearts were divided into 4 parts from apex to base along the long axis. The $1^{st}$ and $2^{nd}$ parts of all hearts contained infarct area (18/18); the $3^{rd}$ parts of most hearts contained infarct area (12/18); the $4^{th}$ parts of a few hearts contained small part of infarct area (3/18).

Figure 2:
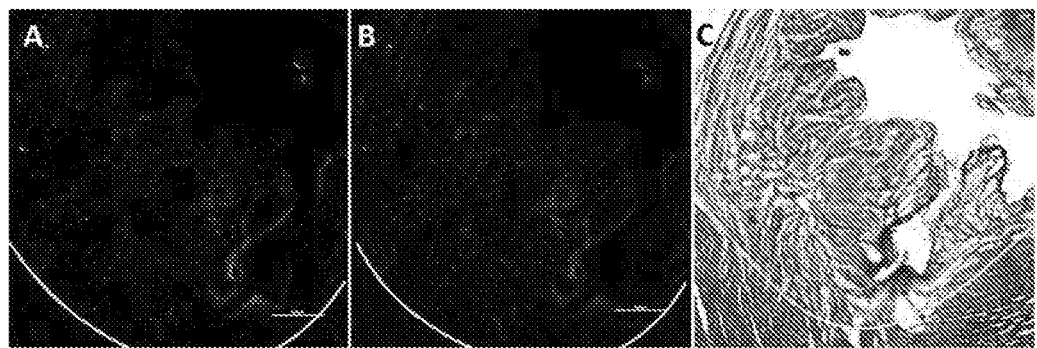
FIG. 2 shows that BMSCs homing in most of the infarction area under the acute myocardial infarction condition.
Figure 3:
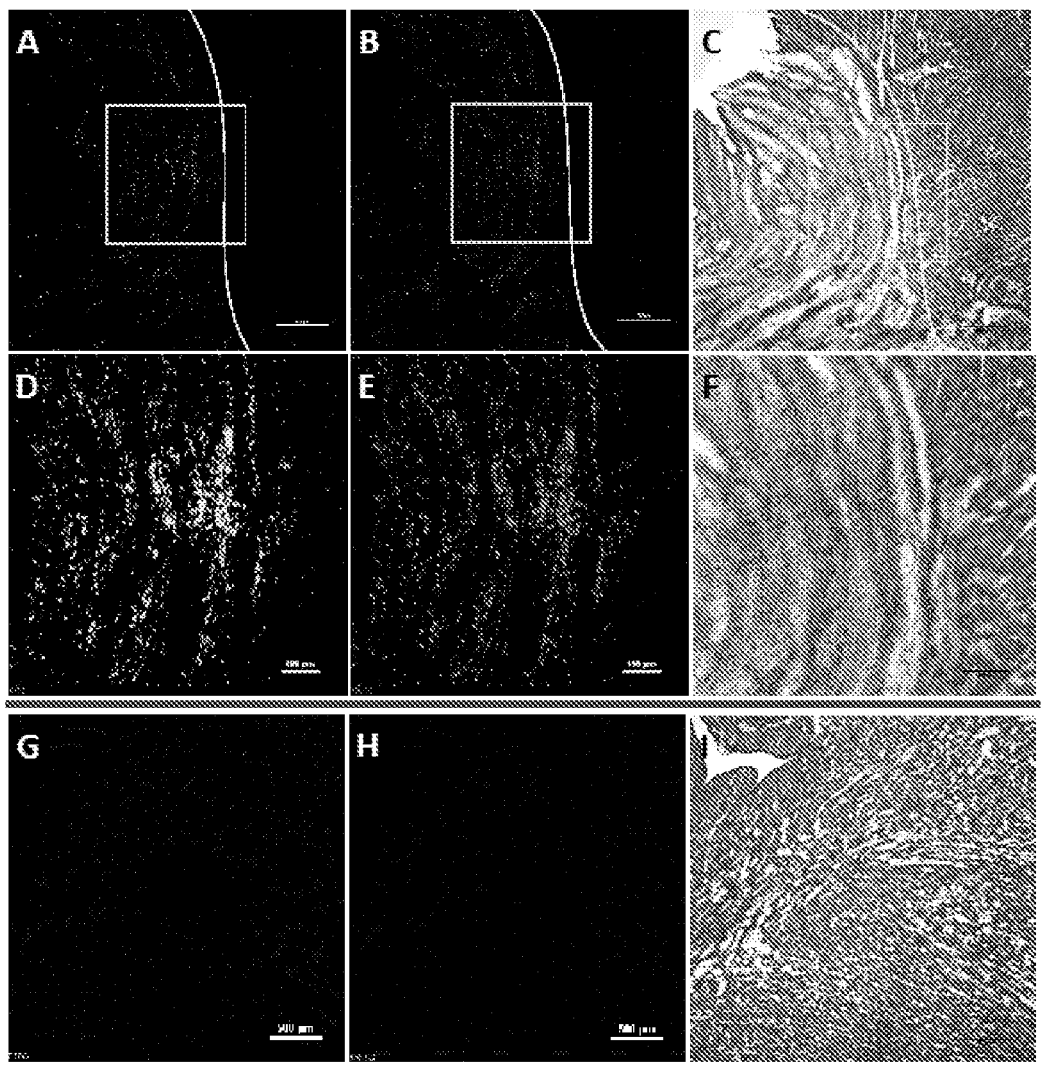
FIG. 3 shows BMSCs homing in the infarction area, but not in the noninfarcted area.
Figure 4:
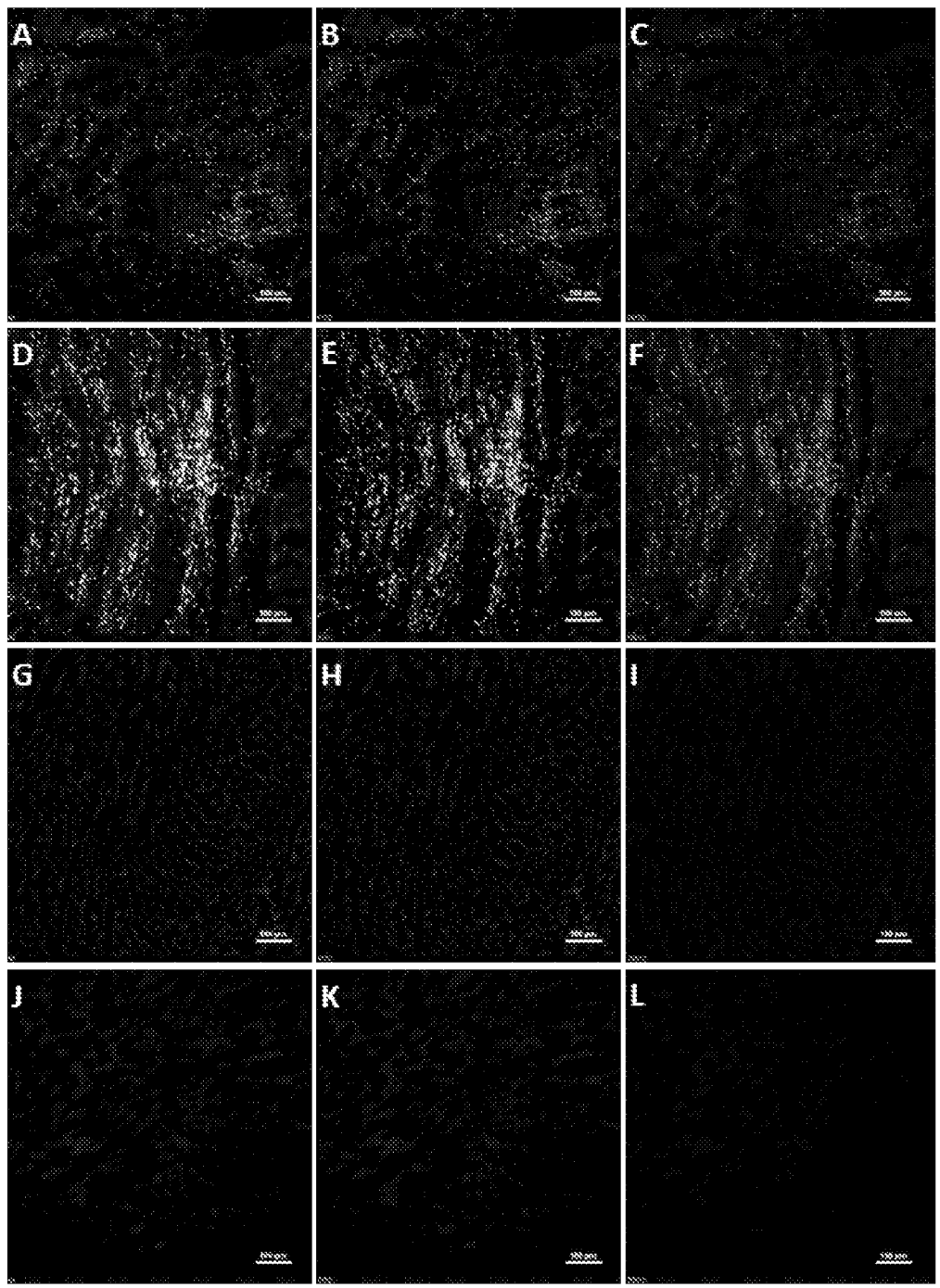
FIG. 4 shows strong BMSCs homing signals in the acute myocardial infarction area.

For acute cardiac infarction, homing signals were abundant and intense in and around the infarct area. Within 1 month of MI surgery, successfully established experimental MI rabbits were considered acute cardiac infarcted models (Acute, n=3). During acute infarction, animals initiate spontaneous self-repair, strong signals of homing BMSCs scattering the infarct area could be observed (FIG. 2-4). In this experiment, overlapped green and red fluorescent signals were observed as homing signals, which were seen in and around the infarct area, rather than non-infarct area (FIG. 2-4). FIG. 2 shows that, during acute infarction homing signals of BMSCs were observed in a large part of infarct area. A-C were captured at the same field within the transaction of left ventricle. From left to right, green and red signals, HE results are shown. Yellow dotted lines divide the area into infarct area (up) and non-infarct area (down). Images were captured in 40× field, ruler=500 μm. FIG. 3 shows that homing signals were only seen in infarct area. A-C, D-F, G-I are from the same heart, A-C and D-F are images of the same field within infarct area ($2^{nd}$ part), G-I are images within non-infarct area. D-F are blue lined regions in A-C. Yellow dotted lines divide the area into infarct area (left) and non-infarct area (right). G-I are images of non-infarct area. Overlapped red and green signals are seen in the infarct area, whereas few could be found in margins of infarct area or area far from infarct. From left to right, green and red signals, HE results are shown. A-C, G-I were captured in 40× field, ruler=500 μm; D-F were captured in 100× field, ruler=100 μm (D-E) or 200 μm (F). FIG. 4 shows that, during acute infarction strong homing signals of BMSCs were observed. Within 1 month after the MI surgery, intense homing signals were observed in the infarct area. From top to bottom are images from the $1^{st}$ (A-C), $2^{nd}$ (D-F), $3^{rd}$ (G-I), and $4^{th}$ (J-L) part. Fluorescent signals were seen in infarct area (the $1^{st}$ and $2^{nd}$ part, A-F); no signal was seen in non-infarct area (the $3^{rd}$ and $4^{th}$ part, G-L). Images were captured in 100× field, ruler=100 μm.

Figure 5:
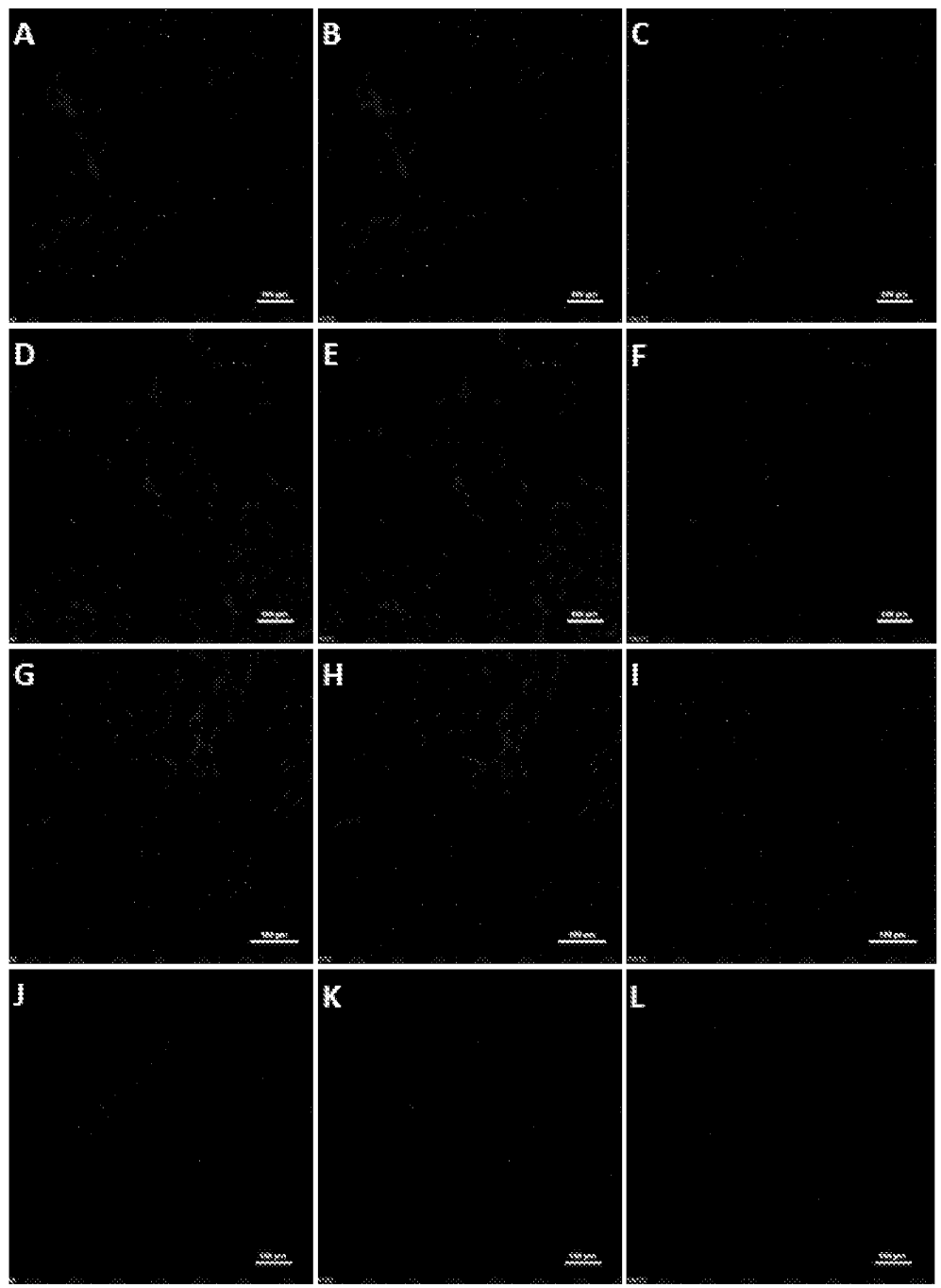
FIG. 5 shows no BMSCs homing signal detected under the chronic myocardial infarction condition.

Results from this experiment have demonstrated that homing of BMSCs disappeared when the heart was under chronic ischemia, but Cu-albumin-microbubble treatment initiated re-homing of BMSCs. 6 months after the MI surgery, successfully established experimental animals were considered chronic cardiac ischemia (Chronic, n=3). The spontaneous self-repair, as well as homing of BMSCs of these animals heavily decreased or even disappeared. Overlapped green and red signals (homing signals of BMSCs) could not been found in both infarct and non-infarct areas (FIG. 5). FIG. 5 shows that homing signals of BMSCs disappeared during chronic cardiac ischemia. After 6 month of the MI surgery, hearts were sliced and imaged. Signals could not be observed in the $1^{st}$ (A-C), $2^{nd}$ (D-F), $3^{rd}$ (G-I), and $4^{th}$ (J-L) part. From left to right, green and red signals, HE results are shown. Images were captured in 100× field, ruler=100 μm.

Figure 6:
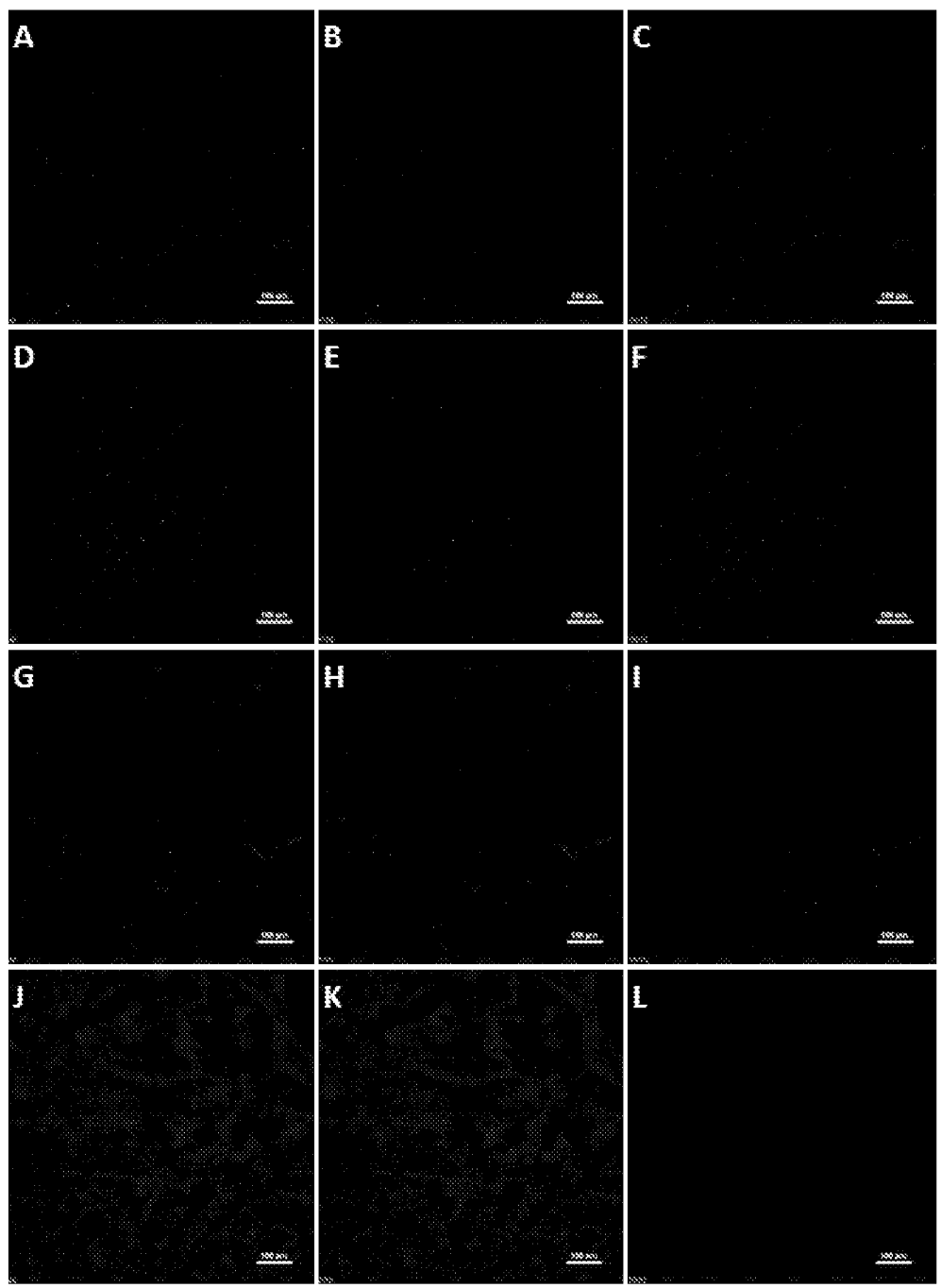
FIG. 6 shows without myocardial infarction, Cu-MB treatment alone cannot mobilize BMSCs homing.
Figure 7:
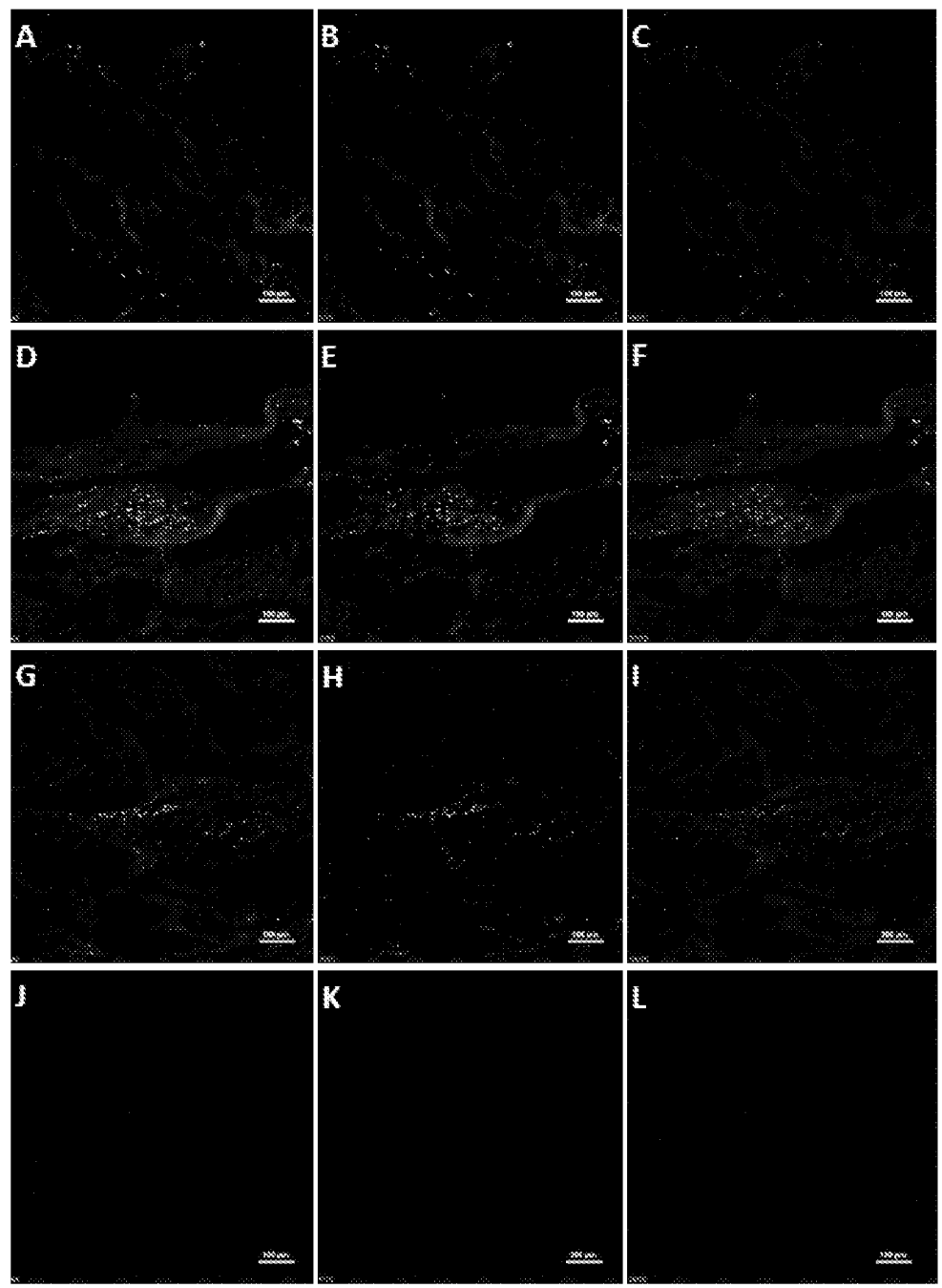
FIG. 7 shows reoccurrence of BMSCs homing signals after Cu-MB treatment of chronic myocardial infarction.
Figure 8:
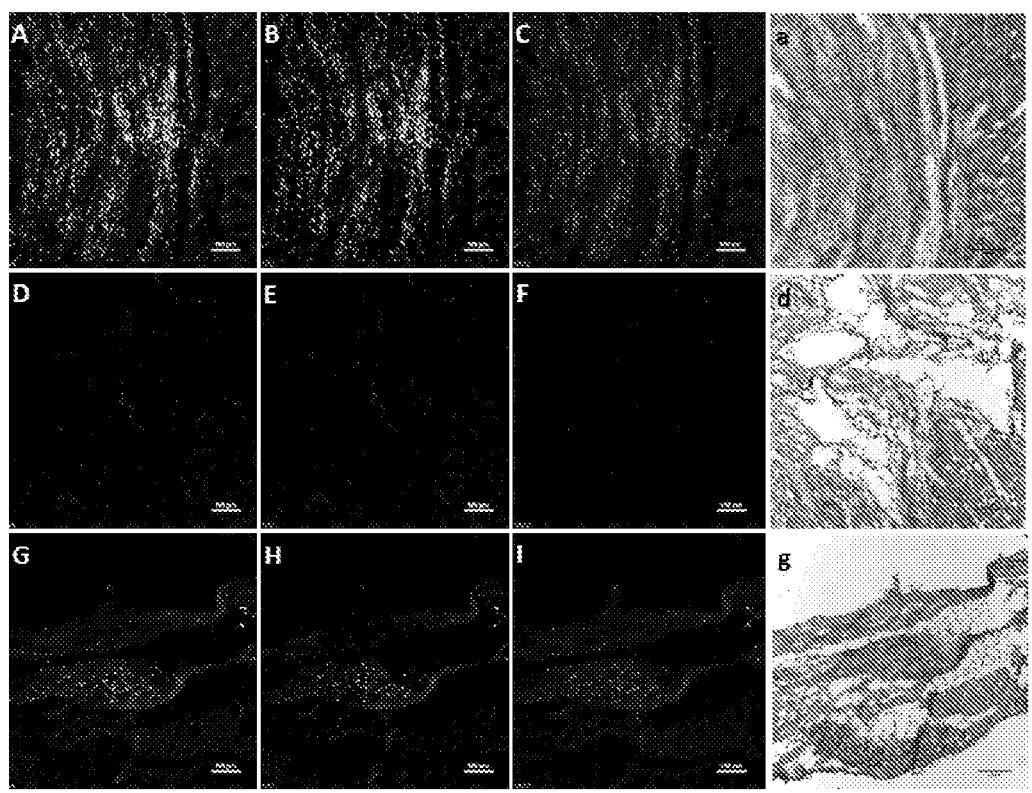
FIG. 8 shows reoccurrence of BMSCs homing after Cu-MB treatment of chronic myocardial infarction.
Figure 9:
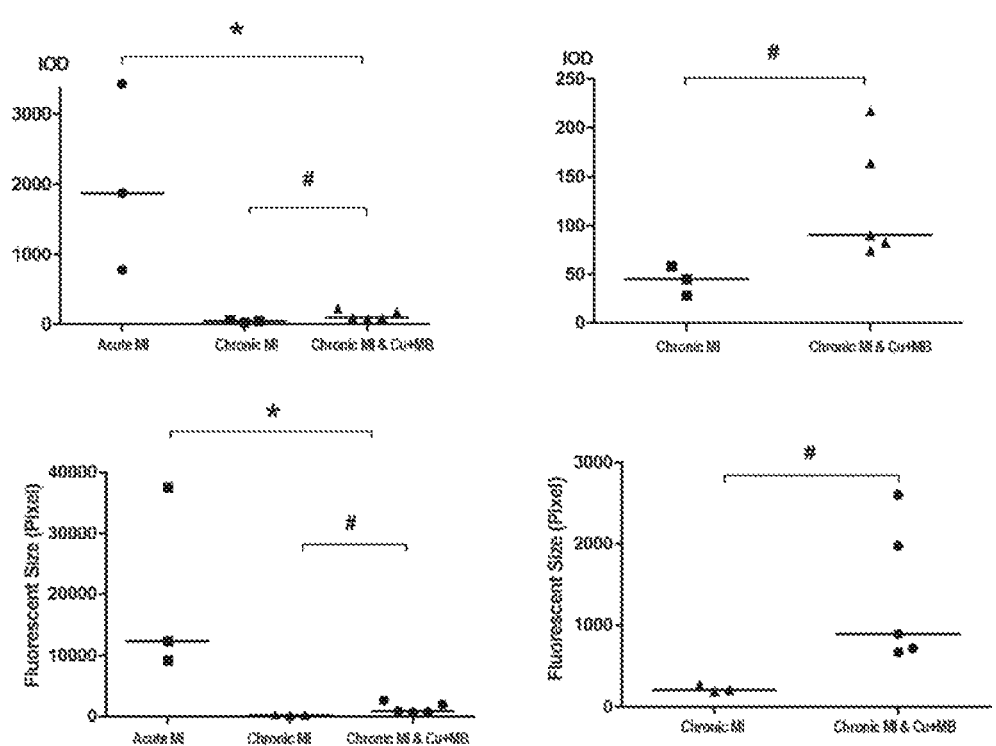
FIG. 9 shows quantification of homing signals of the acute myocardial infarction, chronic myocardial infarction, and Cu-MB treated chronic myocardial infarction groups.

Oriented copper supplement to cardiac infarct area was achieved by ultrasound location and irradiation of Cu-albumin-microbubble. Cu-albumin-microbubble treatment does not initiate BMSCs homing non-infarcted hearts (FIG. 6). FIG. 6 shows that, with no infarction, Cu-albumin-microbubble treatment did not initiate BMSCs homing. From top to bottom are images from the $1^{st}$ (A-C), $2^{nd}$ (D-F), $3^{rd}$ (G-I) and $4^{th}$ (J-L) part. Fluorescent signals could not be found in any area (the $1^{st}$ and $2^{nd}$ part, A-F). From left to right, green and red signals, HE results are shown. Images were captured in 100× field, ruler=100 μm. Treating rabbits suffered from 6-month-cardiac-ishemia with Cu-albumin-microbubble resulted in re-homing of BMSCs (FIG. 7). Six months after the MI surgery, Cu-albumin-microbubble treatment initiated re-homing of BMSCs to infarct area. From top to bottom are images from the $1^{st}$ (A-C), $2^{nd}$ (D-F), $3^{rd}$ (G-I), and $4^{th}$ (J-L) part. Fluorescent signals were seen in infarct area (the $1^{st}$, $2^{nd}$ and $3^{rd}$ part, A-I); no signal was seen in non-infarct area (the $4^{th}$ part, J-L). From left to right, green and red signals, HE results are shown. Images were captured in 100× field, ruler=100 μm. Though the abundancy, intensity and seen region are much smaller compared with homing signals during acute infarction, homing signals initiated by microbubble treatment are obviously lifted compared with chronic infarcted animals receiving no treatment (FIG. 8-9). FIG. 8 shows that Cu-albumin-microbubble treatment initiated re-homing of BMSCs to infarct area. During acute infarction, abundant homing signals of BMSCs were observed in infarct area (A-C, a). Homing signals disappeared in chronic cardiac ischemic hearts (D-F, d). After Cu-albumin-microbubble treatment, disappeared homing signals re-appeared in infarct cardiac area (G-I, g). Images are all from slices of the $2^{nd}$ part. From left to right, green and red signals, HE results are shown. Images were captured in 100× field, ruler=100 μm (A-C, D-F, G-I) or 200 μm (a, d, g). FIG. 9 shows the statistics analysis of fluorescent signals of group Acute, Chronic, and Chronic & Microbubble. Up is analysis of IOD values, down is of fluorescent areas. Differences between groups were tested by sum of ranks. The short lines represent medium, * and # means p≤0.05.

Results from this experiment have demonstrated that re-homing of BMSCs stimulated by Cu-albumin-microbubble is SDF-1/CXCR4 axis dependent. SDF-1/CXCR4 axis is one of the important mechanisms for stem cells homing. SDF-1 is expressed by injured tissues, attracting various stem cells including BMSCs homing. The specific receptor CXCR4 expressed at the surface of stem cells respond to SDF-1 and initiates homing of the cell. To specifically blocking SDF-1/CXCR4, AMD3100 the blocker of CXCR4 was chosen to treat the cells.

Figure 10:
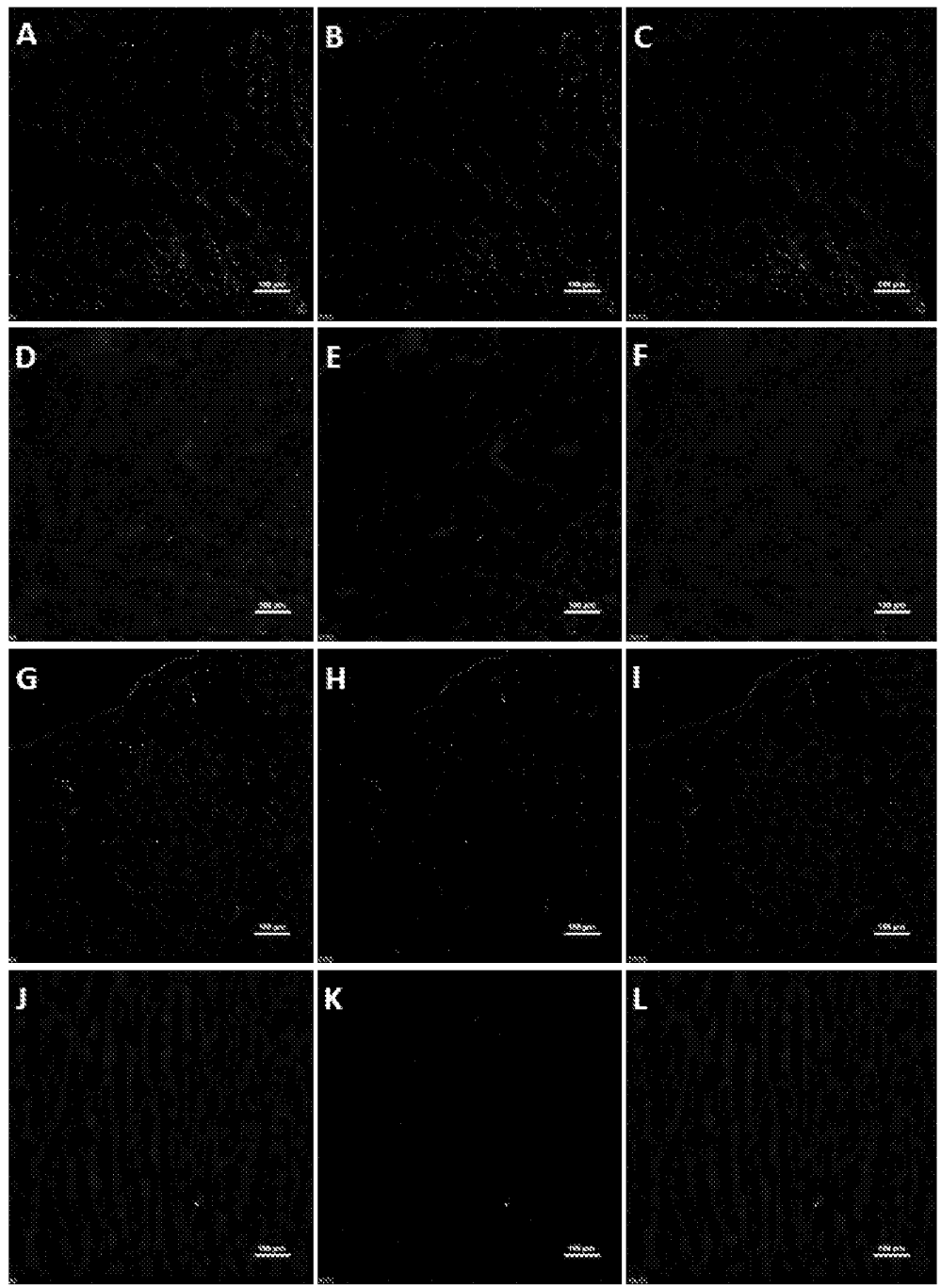
FIG. 10 shows a significant decrease of BMSCs homing signals after treatment with AMD3100 within a month after acute myocardial infarction.
Figure 11:
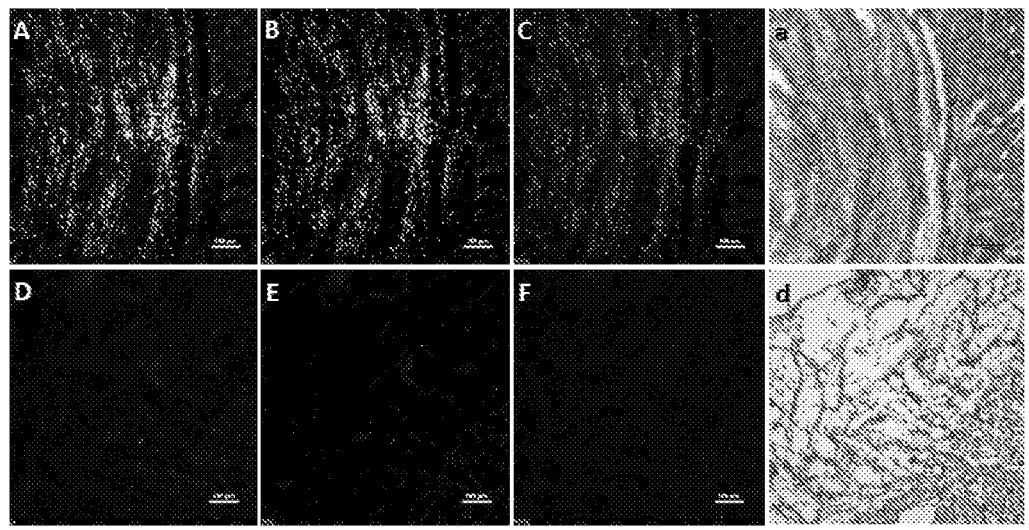
FIG. 11 shows no BMSCs homing signal of AMD3100 treated BMSCs in acute myocardial infarction.
Figure 12:
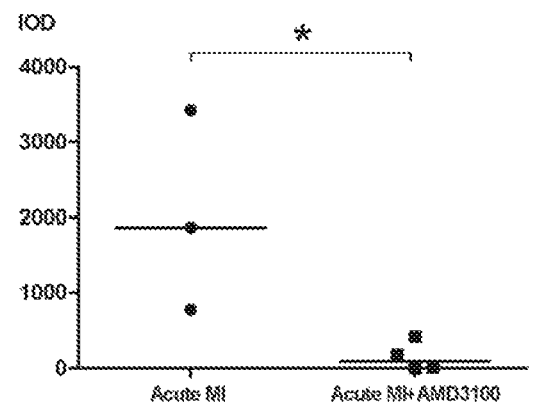
FIG. 12 shows quantification of homing signals of acute myocardial infarction, and homing signals of BMSCs treated AMD3100 in acute myocardial infarction.
Figure 12:
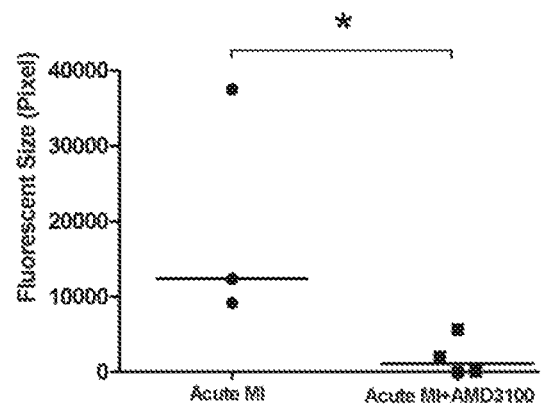
Figure 13:
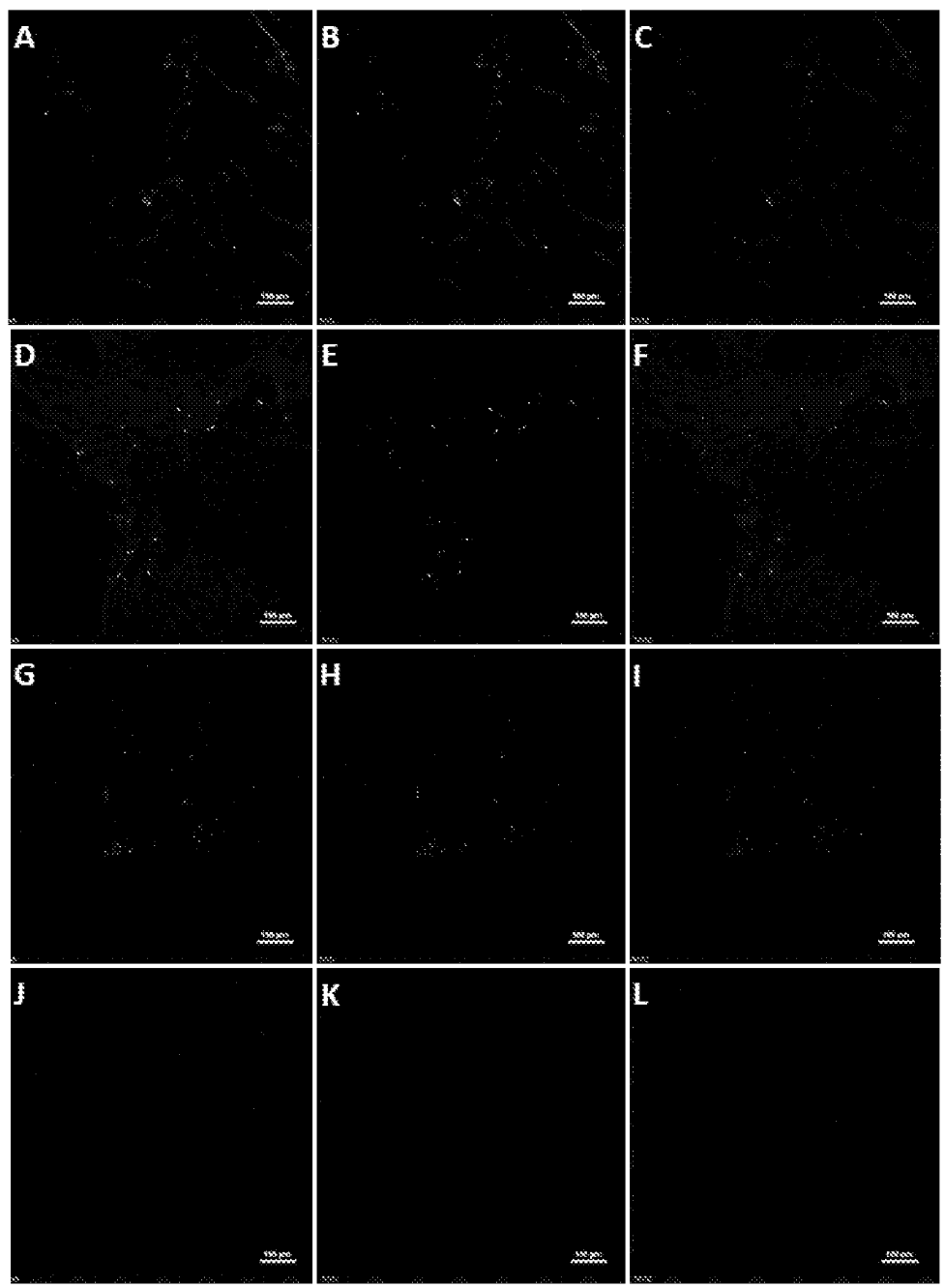
FIG. 13 shows no BMSCs homing signal after treating BMSCs with AMD3100 in the Cu-MB treated chronic myocardial infarction group.

Results from this experiment have demonstrated that AMD3100 treated BMSCs could not home cardiac infarct area. Cells were labeled with pKH26, Dio(3) and Hoechst, incubated with AMD3100 overnight, and then harvested and injected into the rabbit. Abundant and intense homing signal were NOT observed when AMD3100 treated BMSCs were injected into acute infarcted rabbits. Both the abundance and seen region of the homing signals shrunk markedly compared with that of acute infarcted rabbits that received non-AMD3100-treated BMSCs (FIG. 10-12), demonstrating that AMD3100 inhibited the SDF-1/CXCR4 dependent homing. FIG. 10 shows that AMD3100 treated BMSCs could not home acute cardiac infarct area. Within 1 month after the MI surgery, the homing ability of AMD3100 treated BMSCs to infarct area obviously decreased (the $1^{st}$, $2^{nd}$ and $3^{rd}$ part, A-I). From top to bottom are images from the $1^{st}$ (A-C), $2^{nd}$ (D-F), $3^{rd}$ (G-I), and $4^{th}$ (J-L) part. Fluorescent signals were few in either part. From left to right, green and red signals, HE results are shown. Images were captured in 100× field, ruler=100 μm. FIG. 11 shows that AMD3100 treated BMSCs could not home acute cardiac infarct area. From top to bottom are images from group Acute (A-C, a) and Acute+AMD3100 (D-F, d) (all from the $2^{nd}$ part). From left to right, green and red signals, HE results are shown. Images were captured in 100× field, ruler=100 μm (A-C, D-F) or 200 μm (a, d). FIG. 12 shows the statistics analysis of fluorescent signals of group Acute and Acute+AMD3100. Up is analysis of IOD values, down is of fluorescent areas. Differences between groups were tested by sum of ranks. The short lines represent medium, * and # means p≤0.05.

Figure 14:
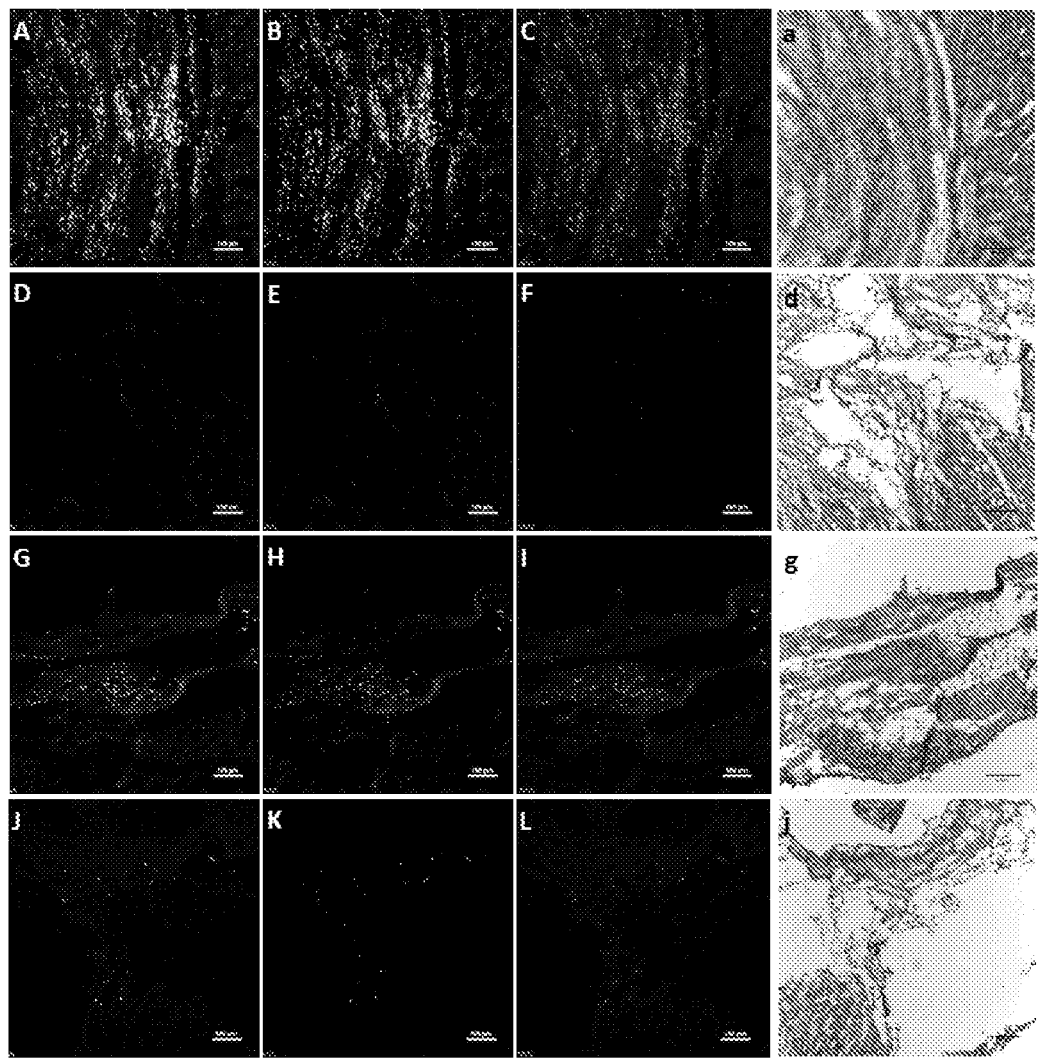
FIG. 14 shows no BMSCs homing signal after treating BMSCs with AMD3100 in acute myocardial infarction, and no BMSCs homing signal after treating BMSCs with AMD3100 in the Cu-MB treated chronic myocardial infarction group.
Figure 15:
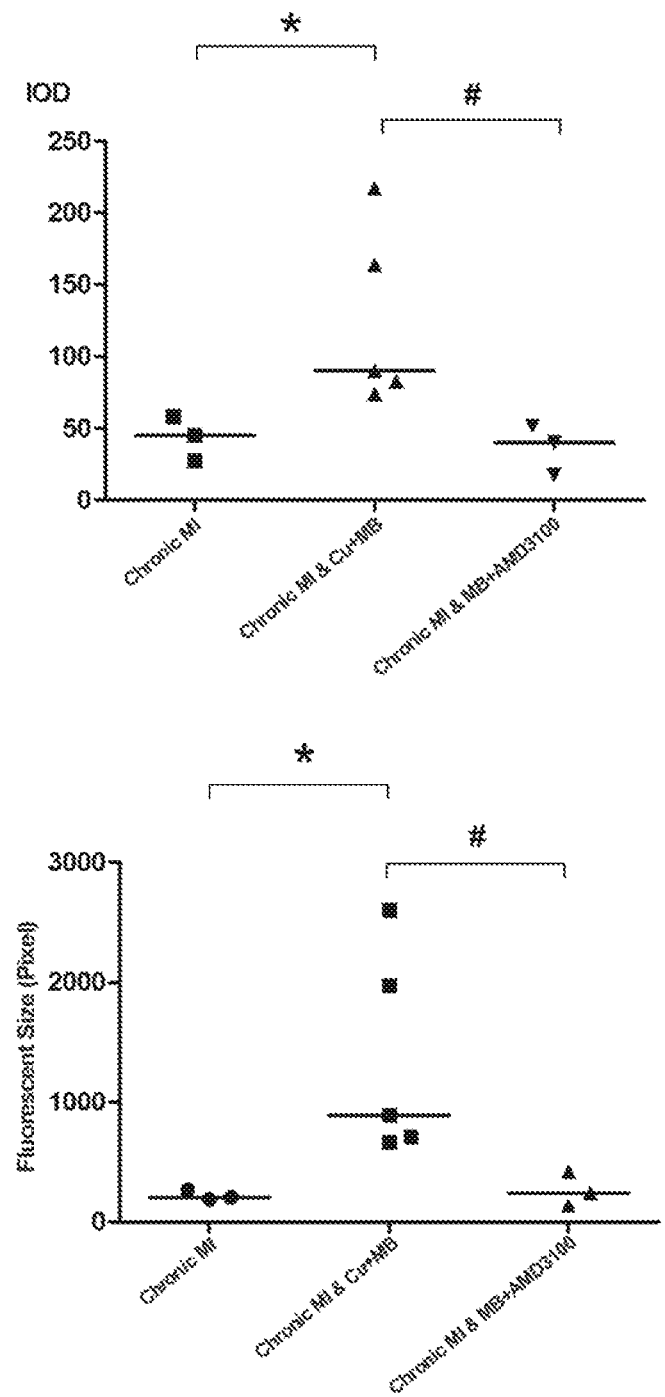
FIG. 15 shows quantification of BMSCs homing signals of chronic myocardial infarction, Cu-MB treated chronic myocardial infarction, and AMD3100 treated Cu-MB treatment chronic myocardial infarction group.

Results from this experiment have shown that AMD3100 treated BMSCs could not home chronic cardiac ischemic area. Six months after the MI surgery, Cu-albumin-microbubble treatment initiated re-homing of BMSCs to infarct area. However, when tracking cells were AMD3100 treated BMSCs, homing signals could not be observed in Cu-albumin-microbubble treated chronic ischemic area. If cells were treated with AMD3100, homing signals stimulated by Cu-albumin-microbubble could not be found in infarcted rabbits that underwent cardiac ischemia for 6 months and received Cu-albumin-microbubble treatments. From top to bottom are images from the $1^{st}$ (A-C), $2^{nd}$ (D-F), $3^{rd}$ (G-I), and $4^{th}$ (J-L) part. The $1^{st}$ to $3^{rd}$ (A-I) part contain infarct area, but few homing signal was seen in either part. From left to right, green and red signals, HE results are shown. Images were captured in 100× field, ruler=100 μm. FIG. 14 shows that AMD3100 treated BMSCs could not home acute cardiac infarct or chronic cardiac ischemic area. From top to bottom are images from group Acute (A-C, a), Chronic (D-F, d), Chronic & Microbubble (G-I, g) and Chronic & Microbubble+AMD3100 (J-L, j) (all from the $2^{nd}$ part). From left to right, green and red signals, HE results are shown. Images were captured in 100× field, ruler=100 μm (A-C, D-F, G-I, J-L) or 200 μm (a, d, g, j). FIG. 15 shows the statistics analysis of fluorescent signals of group Chronic, Chronic & Microbubble and Chronic & Microbubble+AMD3100. Up is analysis of IOD values, down is of fluorescent areas. Differences between groups were tested by sum of ranks. The short lines represent medium, * and # means p≤0.05.

As a myocardial infarction model, New Zealand white rabbits are lower in cost, convenient in feeding and transportation, not imperative of mechanical respiration during MI surgery, and easy in ligation of coronal arteries. Ligation of coronal arteries was mostly achieved by ligation of LAD (left anterior descending) or LC in previous literatures. In this experiment, results had shown that ligation of LAD could not establish stable myocardial infarction model. Through ink perfusion, it was observed that the LAD of rabbits is distinctively shorter than that of rats and pigs. It reaches at most ⅓ of the anterior wall of left ventricle, supplying blood for quite a limited area—10%~15% of the left ventricle. However, LC is relatively longer and bigger, reaching the apex (in some cases, rounding the apex and reach the right coronary arteries), supplying blood for most area of left ventricle.

Ligation of LC provided more successful and stable models than ligation of LAD. Results from echocardiography and hemodynamic measures have shown that, the cardiac function of rabbits with LAD ligation did not change evidently, whereas that of LC ligation drastically changed. Pathology analysis also has proved that, in infarct area of LC ligated rabbits was obviously bigger than that of LAD ligated rabbits. Besides, LC travels at the surface of myocardium, making it easy to recognize and operate on.

Ultrasound microbubbles are a kind of favorable ultrasound contrast agents and target drug carriers. Microbubbles stay stable in transportation before irradiated by ultrasound irradiation, which is manly controlled. So drugs on microbubbles could be oriented destructed at the target tissues. Besides, the destruction of microbubbles and ultrasound irradiation helps the drugs entering the cells. Ultrasound-microbubble is easy in operation, causes little damage to animals, and promises timely and located copper supplement as well. Thus, in this experiment, ultrasound mediated Cu-albumin-microbubble was chosen to replenish copper to myocardium.

Stem cell homing is a systematic reaction involving the whole body. Systematic observation is more persuasive than simple protein tests. So this experiment researched the mechanisms of Cu-albumin-microbubble stimulated BMSCs homing through AMD3100 treating, illustrating the stimulated homing was SDF-1/CXCR4 axis dependent, which suggested that the mechanism may be Cu lifts HIF-1 activity—HIF-1 stimulates the expression of SDF-1—SDF-1 attracts stem cells homing.

Cardiac ischemia results in hypoxia, which enables HIF-1α escaping from degradation and accumulating in the cytosol. When transported into the nucleus, HIF-1α dimerizes with HIF-1β to form HIF-1. However, in the nucleus, HIF-1α is hydroxylated by the asparaginyl hydroxylase factor inhibiting HIF-1 (FIH-1) on its N803 asparagine residue within its carboxyl terminal, leading to the inhibition of HIF-1α from interacting with co-activators CBP/p300 and form functional transcription complexes. Copper suppresses the activity of FIH-1, so that promotes the combination of HIF-1 and other factors to form functional transcription complexes. HIF-1 could not form functional complex and initiates the expression of downstream genes when copper is insufficient in the system. Nevertheless, cardiac ischemia that accumulates the HIF-1α causes copper efflux from the heart, leading to suppressing of the HIF-1 transcriptional activity and inhibition of expression of HIF-1 regulated genes including homing chemokines (e.g. SDF-1). Thus, along with the elongation of cardiac ischemic time, homing of BMSCs diminishes to even disappear.

Results from this experiment have shown that, during acute cardiac infarction, BMSCs did home the infarct area. With ischemic time extending to 6 months, homing of BMSCs disappeared. Oriented supplement of copper to the heart by Cu-albumin-microbubble, re-homing of BMSCs was observed. In conclusion, Cu-albumin-microbubble stimulates the homing of BMSCs during chronic cardiac ischemia, and the stimulated homing process is HIF-1-SDF-1 dependent.

Example 2

Copper Ultrasound Contrast Microbubble Targeted Therapy for Ischemia Myocardial Infarction Model in Rhesus Monkey This experiment was conducted in Rhesus monkeys. Ischemia myocardial infarction model was established by coronary artery ligation operation. Four weeks after operation, the ischemic cardiac tissue was fully replaced by collagenous fiber and became infarcted tissue. Then the ultrasound-guided copper microbubble targeted therapy was performed to treat myocardial infarction for therapeutic effective assessment. The Rhesus monkey possess high-order heart resemble that of human with a similar internal structure, electrical activity, distribution of coronary arteries, coronary collateral circulation, placement and attachment in the thoracic cavity. Thus, Rhesus monkey model of myocardial infarction would provide a better surrogate for myocardium infarction condition in humans.

1.1 Establishment of Ischemia Myocardial Infarction Model in Rhesus Monkey

Prior to surgical procedure, all subjects received an intramuscular injection of 5 mg/kg ketamine and 0.2 mg/kg midazolam to induce sedation. Hairs covering chest and limbs at electrode attachment sites were shaved thoroughly for operation and better ECG recording. The standard bipolar and unipolar limb leads were recorded. Animals displaying abnormal ECG, such as tachycardia (more than 200 beat per minute), arrhythmia, and obviously ST segments deviated from the base line were excluded from this study.

Standard noninvasive measurements including electrocardiography, cuff blood pressure, pulse oximetry, and capnography were constantly monitored (Dash3000, GE, USA.), and vein catheters were established. All of the monkeys subjected to surgical procedure were firstly intubated after anesthesia induced by intravenous infusion with fentanyl (10 μg/kg), midazolam (0.2 mg/kg), propofol (1 mg/kg), and vecuronium (0.1 mg/kg). Assisted respiration was conducted with pressure-controlled ventilation to achieve end-tidal $CO_2$ between 35 mmHg to 40 mmHg. Inspiratory pressure was set within a range from 12 to 20 cm $H_2O$, the respiratory rate was 40/min, and the inspiratory/expiratory ratio was 1:2.

In order to maintain the anesthetic condition during the surgical procedure, 2 mL of fentanyl (0.1 mg) and 10 mL of propofol (100 mg) was diluted to 20 mL by saline. The mixture was infused continuously by a syringe pump at the speed of 5-10 mL/h. The pump speed was adjusted according to the anesthetic state and operation time of duration. Arterial cannulation was punctured into the femoral artery with an indwelling needle and connected pressure monitoring tubing for invasive blood pressure monitoring during the operation. Normally, the femoral arterial pulsation can be palpated midway between the anterior superior iliac spine and the pubic symphysis. The operating area was isolated in an aseptic manner. The isolation is done with the help of 4 pieces of the disposable sterile sheet.

Surgical area was cut slightly medial to the line of the left fourth intercostal space, and made a 4-5-cm transverse incision outward from the left side of presternum. The monopolar diathermy is recommended as it can be used both for cutting tissues and coagulation. The s.c. tissue and the muscular planes were dissected down to the pleura, entering the pleural space, and then incision was widened by opening the forceps. A cotton bud was inserted, sweeping the pleural space and pushing the lung away from the hole, and then the intercostal incision was widened to open the chest and expose the pericardium.

The heart was exposed via the left fourth intercostal thoracotomy incision (4-5 cm) and the apex and left auricle were identified. The epicardial end of the LAD was defined as level zero; the origin of the LAD under the left auricle was defined as level 100. The ligation was performed in a certain location. In addition, the major diagonal branch was also ligated parallel to the ligation site on the LAD artery in some monkeys if the branching site of diagonal artery is above the ligation site.

The artery was occluded for 1 min followed by a 5-min reperfusion, and this occlusion-reperfusion was repeated 3 times before the eventual ligation. After final ligation, the difference of left ventricular wall motion, color changes of the anterior ventricular wall, and alterations in electrocardiogram and blood pressure need to be monitored to ensure that the ligation is successful. Inject methylene blue (1 mL) bolusly into left auricle with a 1.0 mL syringe after the permanent ligation. The filling defect of the methylene blue tells the completion of the ligation, as well as the prediction of ischemic area.

Before closing the chest, heart condition was intensively monitored for 45 min. Dobutamine (3-5 $\mu g \cdot kg^{-1} \cdot min^{-1}$) was infused to support the cardiac function and defibrillator (HEARTSTART XL, Philips) was used if necessary. Care needs to be taken to avoid damaging the heart during the pericardium closing. Sodium hyaluronate should be infused into the pericardial chamber for anti-adhesion treatment. The pericardium and pleura were closed with 4-0 polyethylene sutures. The intercostal incision was closed with silk suture. To avoid the pneumothorax, care needs to be taken to avoid damaging the lung during the intercostal closing. Re-inflate the lungs while intercostal incision closing so that the air can be expelled from the pleural cavity. After intercostal incision closed, saline solution is dropped to the subcutaneous space, the lung is inflated again for sure that the chest incision is closed tightly. The muscle and the skin incision were closed in layers with #2-0 silk sutures, and cleaned in a sterile manner. The endotracheal tube was retracted after the spontaneous breathing was restored. The incision was covered with sterile gauze and bandage. Tramadol (2 mg/kg) was injected intramuscularly to smooth the pain out. The bandage change was performed on alternate days and sutures were removed one week after the operation.

1.2 ECG Monitoring

A 12-lead ECG (MAC8000, GE, USA.) was recorded on the supine position of each monkey at the time before, immediately after the operation (about 2 hours for the entire surgical procedure), four and eight weeks after the operation using pediatric electrodes at 25 mm/s paper velocity and 10 mm/mV amplitude. The chest wall of a monkey was not wide enough to allow 6 precordial leads at the same time even with the pediatric electrodes. Therefore, the 6 precordial leads were divided into two groups; V1, V3, and V5 were recorded in one group, and V2, V4, and V6 in another group.

1.3 Echocardiography

Two-dimensional echocardiographic measurements were performed on standard apical 2- and 4-chamber views with three consecutive cardiac cycles. The frame rate was kept between 70 fps and 100 fps. All monkeys were subjected to transthoracic echocardiographic evaluation with the 10.3 MHz transducer (P10-4, Siemens ACUSON Antares System, German) in the left lateral position at the time before, four and eight weeks after the operation.

The ejection fraction (EF) of the left ventricle was evaluated with the Simpson's single-plane method. Left-ventricular end-diastolic volume (LVEDV) and end-systolic volume (LVESV) were directly recorded, and EF=(LVEDV−LVESV)/LVEDV×100%. Stroke volume (SV) of the left ventricle was calculated as SV=LVEDV−LVESV.

1.4 Cardiac Magnetic Resonance Imaging (MRI)

All monkeys were anesthetized with intramuscular injection of 10 mg/kg ketamine and 0.2 mg/kg midazolam, intubated to assist respiration, and studied on a clinical 3.0-T scanner (Siemens) in the supine position before and after treatment, using a cardiac dedicated phased-array coil and ECG-triggering. The ECG for sequence triggering is one of the most important cornerstones of the MR exam. Functional examinations (cine MRI) were performed using a breath-hold, short-axis, steady-state free precession sequence (whole left ventricular coverage; 1 slice per breath-hold; TR/TE, heartbeat interval/minimum; slice thickness, 10 mm; number of views per segment, 8). Gadopentetate dimeglumin-enhanced acquisitions were obtained along the ventricular short-axis using an interleaved notched saturation segmented gradient-echo-echo-planar hybrid pulse sequence for 50 heart beats during the first-pass of the contrast material (perfusion scanning with five images per heartbeat; inversion time, 160 msec; IV bolus of with a left 0.1 mmol/kg delivered at 5 mL/sec), followed by an inversion-recovery prepared gradient-echo sequence (one slice per breath-hold, five slices for each early and delayed phase) along the left ventricular short-axis performed 2 and 10 minutes after administration of a second 0.1 mmol/kg bolus for early and delayed enhancement imaging, respectively (inversion time to null normal myocardium fixed at 200 and 250 ms for early and delayed enhancement imaging, respectively). Additional views (four-chamber or long-axis) were obtained if needed. Total study time was approximately 30 minutes.

MRI images analysis: For analysis, images were displayed on the computer monitor with the generally accepted software, Syngo Argus, which conveniently displayed the images of different phases of cardiac cycle in the same slices in the same row, and aligned the images of the same phase of cardiac cycle of different slices. With the Simpson's rule approach, which is most commonly used in cardiac MRI, a dynamic series of cine MRI images can be analyzed to provide accurate assessment of ventricular volumes. From the contours that were manually traced to define the endocardial and epicardial borders of the myocardium of each slice, in which the papillary muscles were included, ventricular volume and global function parameters, including end-diastolic and end-systolic volumes, ejection fraction, stroke volume, could be determined automatically using Simpson's rule by the software Syngo Argus.

Infarction size: Randomized and anonymized images were analyzed using the cardiac analysis software. To estimate the infarct size, endocardial and epicardial borders were segmented on LGE images automatically with manual adjustments followed by automatic delineation of infarct tissue using a built-in fraction of segment. Manual corrections were performed where necessary. Infarct size, expressed as percentage of left ventricular mass, was calculated as infarct volume/left ventricular volume (from cine data). The chronic infarct size measurements as determined by Contrast-Enhanced Magnetic Resonance Imaging were reproducible.

1.5 Copper Ultrasound Microbubble Treatment

Prior to surgical procedure, all subjects received an intramuscular injection of 5 mg/kg ketamine and 0.2 mg/kg midazolam to induce sedation. Hairs covering chest and limbs at electrode attachment sites were shaved thoroughly for microbubble treatment and better ECG recording. The vein catheter was established. The ultrasound-guided therapy of myocardial infarction was performed. The copper microbubble was infused every three days, through the intravenous access established via the small saphenous vein run along the posterior of the leg. During each copper microbubble treatment, the ultrasound probe (Vivid 7, M3S, GE) was placed on the precordium of the chest so that the ultrasound wave can be directed to the infarction area of heart. The mechanic index was set to 1.2. After each injection, the copper microbubbles which arrived to ventricular through the circulation system were exploded by ultrasound power triggering. At some time, the ultrasound probe was moved slightly back and forth along the short axis between the apex and the mitral valve of the heart. After copper microbubble of each injection was blown up, next infusion was followed until the dose of each treatment (2 mL/kg) was finished. The treatment was conducted in every three days. Before the treatment and two weeks after each monkey received eight times treatment, the cardiac function and structure were evaluated to assess the therapeutic effect.

1.6 Invasive Hemodynamic Measurement

The invasive pressure-volume methodology enables pressure measurement of left ventricular performance offering advantage over other available measurements of cardiac function. Combined with echocardiography detection, the cardiac performance was measured comprehensively. This procedure was only performed before the final harvest of experiment.

The powelab (16 channel, ADinstrument Inc.) recorder was connected with the 3F catheter (Millar Instrument Inc, USA). The pressure was calibrated according to the manufacturer's recommendations.

Anesthesia was induced with intramuscular injection of anesthetic agents. Ketamine (10 mg/kg) in combination with midazolam (0.2 mg/kg) is used for continual and steady sedation. The monkey neck was cleaned and shaved the covering hairs. Then, the animal was placed on the operation table in the supine position. Intravenous access was established with a 25-gauge venous indwelling needle via the small saphenous vein. Anesthesia was maintained with 10 mg/kg of ketamine and 20 mg/kg of propofol, diluted to a final volume of 20 mL with saline. The mixture was infused continuously by a syringe pump at the speed of 1 mL $(kg \cdot h)^{-1}$. In order to achieve reasonable results during the collection of hemodynamics indices, care needs to be taken in the anesthesia maintenance with the proper use and careful optimization of drugs. Even a slightly irregular dose may profoundly affect the heart function.

A 3-4 cm longitude surgical incision was made on the left part of the neck; the s.c. tissue and the muscular plane were dissected between the cutaneous facii and cutaneous colli. The facial plane between the trachea and the sternomastoideus was dissected to palpate the carotid pulse and localize the carotid sheath. Surgical dissection and cannulation of the right carotid artery provides the most direct, timely and reliable access to the left ventricular, which is confirmed by CT scan and 3D reconstruction of carotid artery.

The common carotid artery was isolated using blunt dissection with 2 cm length. Arterial distal was ligated as needed to reduce blood loss. The proximal vessel was controlled with 0 surgical silk sutures, and the proximal was occluded with vascular clamp. The exposed artery was bathed in 2% lidocaine to dilate the vessel and facilitate access.

The carotid vessel was opened with small vessel incision and a 3F Millar catheter was placed in the artery, then the vascular clamp was removed.

The catheter was advanced along the left carotid artery to the left ventricle gradually. Then the proximal vessel control was tightened.

The position of the catheter shaft was set, and rotated to achieve optimal placement of the tip along the axis of the left ventricle for accurate measuring and recording, under the ultrasound-assisted detection. The proximal conductance electrode segments, outside the left ventricular chamber showing a figure eight or irregular loop, indicate aortic measurements, and the detected volume by those proximal segments must be excluded. Alternatively, the catheter must be advanced further into the left ventricle. Ensure that the tip of the catheter is facing the apex and the conductance catheter retains a stable and straight position approximately in the middle of the ventricular chamber, avoiding wall contact. If needed, adjust the position of the catheter to obtain regular pressure-volume loops.

After stabilization for a period of time, dobutamine was infused with an infusion pump at a starting dose of 10 $\mu g \cdot kg^{-1} \cdot min^{-1}$, followed by increasing doses of 30, 50, 70 $\mu g \cdot kg^{-1} \cdot min$ for 3 minutes each stage. Heart performance under the stimulation of dobutamine was recorded continuously and simultaneously by the instrument. +dP/dt max, −dP/dt min, LVDP at the basic heart rate (HR), which is defined as the heart rate before dobutamine infusion, and at 110%, 120%, 130%, 140% of the basic heart rate of all the monkeys were collected and analyzed.

1.7 Histopathological Examination

Monkeys were sacrificed by intravenous injection of potassium chloride (10%, 10 mL) and a complete autopsy was performed. Harvested hearts were washed and inspected grossly for visible lesions and fixed in 10% formaldehyde solution. Then the heart was cut into six blocks from apex to base along the long axis The thickness of each block is fixed in 0.5 cm. Ensure the surface of each section is smooth and uniformly during the incision, and the sections must be marked by the ligature with label. Thin sections were cut and stained with Masson and H/E for microscopic examination.

Antibody: Mouse anti human HIF-1α monoclonal antibody: ab16066, Abcam; mouse anti human VEGFA monoclonal: sc-57496, Santa Cruz; rabbit anti human VEGFR1 monoclonal antibody: 1303-12, Epitomics; mouse anti human CD31 monoclonal antibody: Maixin bio-tech company, Fuzhou. Antigen retrieval of HIF-1α was high pressure heat induced antigen retrieval by EDTA whose pH was 9.0, while VEGF and VEGFR1 was microwave heat induced antigen retrieval by citrate buffer solution whose pH was 6.0, and CD31 was microwave heat induced antigen retrieval by EDTA. The working concentration of HIF-1α was 1:800, VEGF was 1:100, and VEGFR1 was 1:100. In the process of immunohistochemical detection, PBS was taken place of the first antibody as negative control; and slides identified exact protein expression as positive control. Ki-67 label was underwent immunofluorescence examination by confocal.

Capillary density: First a maximum capillary distribution visual field was determined under 100 times light microscope, and then 5 randomized visual fields were collected under 200 times light microscope and capillary density was measured. Capillary was defined as diameter of each lumen less than the sum of 8 red blood cell diameter. Measurement was performed by two independent technicians.

Protein expression semi-quantitative analysis: Image-Pro Plus 6.0 image analysis software (Media Cybemetics) was used to analyze protein semi-quantitative expression. Immunohistochemistry slides was observed and taken pictures under light microscope. Slides of different group were assessed by two independent technicians, and there was no significant difference between the two technicians. 5 randomized visual fields of border area and remote area from infarct of each slide was taken pictures under 400 times light microscope.

1.8 Western Blot

Tissue Preparation: The heart was removed from the chest. The left ventricular wall was carefully examined and the infarct area, the border area, and the remote area were separated. The infarct area can be distinguished from non-infarct area as its pale appearance. The border area is defined as area from 1 mm inside to 3 mm outside the infarct area. Samples were preserved in liquid nitrogen for Western blot analysis.

Western Blot: Protein extracts were obtained after grinding each tissues in liquid nitrogen and lysing in the RIPA lysis buffer (Beyotime, CN) containing 1% complete EDTA-free protease inhibitor cocktail (Roche, DE) for 40 min on ice. Protein concentrations were determined by Pierce BCA Protein Assay Kit (Thermo SCIENTIFIC, 23227, USA). Equal amounts of protein (30 μg) from each were solubilized in 5× SDS sample buffer and separated on 10%-SDS and 8% polyacrylamide gels. Proteins were then electrophoretically transferred to a polyvinylidene fluoride membrane (Bio-Rad, USA). Membranes were blocked for 1 hour in Tris-buffered saline/Tween 20 (TBST) (10 mM Tris-HCl, pH 8.0,150 mM NaCl, and 0.1% Tween 20) containing 5% nonfat dry milk, and incubated overnight at 4° C. with respective primary antibodies, such as anti-HIF-1α (Abcam, ab113642, USA), anti-VEGF (Santa Cruz, sc57496, USA), and anti-VEFGR-1(Abcam, ab32152, USA), in blocking solution according to the vender's recommendations. After washing with TBST, the membranes were incubated for 1 h at 37° C. with appropriate secondary antibody. Target proteins were visualized using a chemiluminescence HRP substrate (Millipore, USA) and analyzed by densitometry using a Quantity One Software.

1.9 mRNA Levels of HIF-1 Target Genes

In order to define HIF-1 transcription activity in ischemic myocardium, mRNA level of HIF-1 target genes VEGF and VEGFR-1 (Flt-1) were tested by RT-PCR.

Total RNA was isolated using Trizol (Invitrogen, 15596-026, USA) as manufacturer's instructions. Total RNA 1 μg was reverse transcribed as per protocol using Prime-Script™ RTreagent Kit (TaKaRa, RR037A, Japan) at 37° C. for 15 min followed by 85° C. for 5 s and 4° C. for 5 min. Real-time RT-PCR reactions were performed using SYBR Premix Ex Taq™ II (TaKaRa, RR820A, Japan). To amplify the VEGF and VEGFR1 cDNA fragments, the samples were processed using a BIO-RAD CFX96 Real-Time System: denatured at 95° C. for 30 s, followed by 35 cycles, each with temperature variations as follows: 95° C. for 5 s, 60° C. for 30 s. Results of the log-linear phase of the growth curve were analyzed and relative quantification was performed using the 2-ΔCT method. Gene expression level of VEGF and VEGFR1 is expressed relative to Actin in each sample. At least 3 replicates were run for each sample. Primer sequences are shown in Table 1.

TABLE 1

Primer Sequences

| Target Gene | | Primer Sequence |
|---|---|---|
| Rhesus monkey HIF-1α | forward primer reverse primer | GTCTGCAACATGGAAGGTATTG (SEQ ID NO: 1) GCAGGTCATAGGTGGTTTCT (SEQ ID NO: 2) |
| Rhesus monkey VEGF | forward primer reverse primer | GAGCTTCCTACAGCACAACA (SEQ ID NO: 3) CCAGGACTTATACCGGGATTTC (SEQ ID NO: 4) |
| Rhesus monkey VEGFR1 | forward primer reverse primer | GGGTCACATCACCTAACATCAC (SEQ ID NO: 5) CCTTTCTGCTGTCCCAGATTAC (SEQ ID NO: 6) |
| Rhesus monkey Actin | forward primer reverse primer | CCACGAAACTACCTTCAACTCC (SEQ ID NO: 7) GTGATCTCCTTCTGCATCCTGT (SEQ ID NO: 8) |

1.10 Cu Concentration in the Heart

Tissue samples were freshly frozen and stored at −80° C. before lyophilization. After lyophilization and digestion of the tissues with nitric acid, digests were colorless or light yellow and clear with no visible precipitate or residue. Ultrapure water was added to each vessel to dilute $HNO_3$ to 2% for subsequent analyses of copper. Copper concentrations were determined by graphite furnace atomic absorption spectrophotometry (ICE3500, Thermo) using the program shown in Table 2.

TABLE 2

Graphite furnace atomic absorption spectrophotometry program

| Time (s) | | Argon Gas Flow (L/min) |
|---|---|---|
| 90 | 20 | 0.2 |
| 120 | 20 | 0.2 |
| 850 | 20 | 0.2 |
| 2100 | 3 | 0 |
| 2500 | 3 | 0.2 |

1.11 Statistical Analysis

All data were expressed as means±SD. The variation of each parameter was compared between the four groups using the homogeneity of Levene's test and coefficient of variance (CV). A SPSS 14.0 statistical package (SPSS, Chicago, Ill.) was used, and significant difference was assumed when P values were <0.05.

2. Results 2.1 Cardiac Function and Cardiac Reserve

Figure 16A:
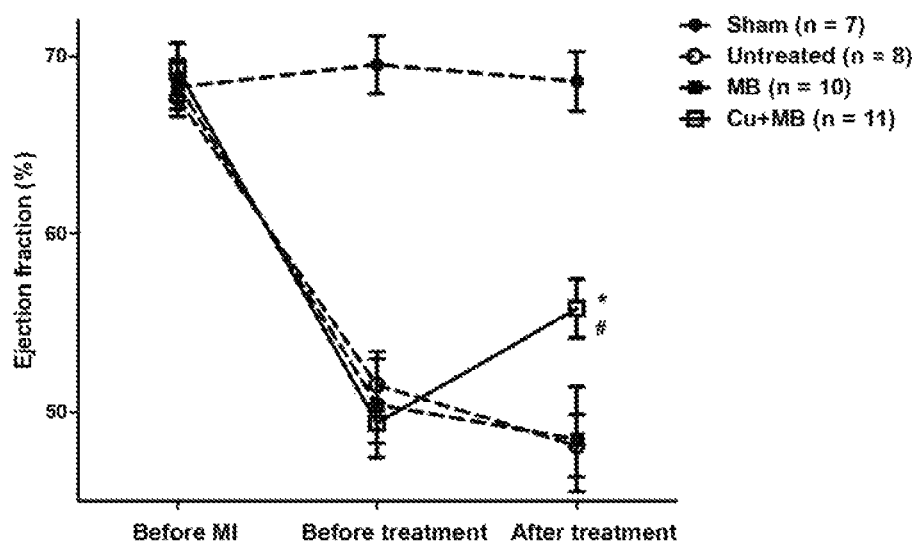
FIG. 16A shows echocardiography detected changes in left ventricular ejection fraction of Rhesus monkeys after treatment with Cu-MB.
Figure 16B:
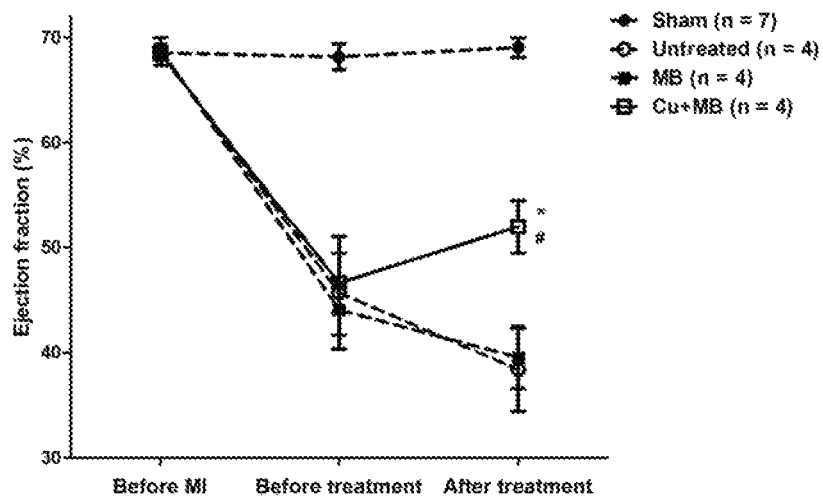
FIG. 16B shows MRI detected changes in left ventricular ejection fraction of Rhesus monkeys after treatment with Cu-MB.
Figure 17:
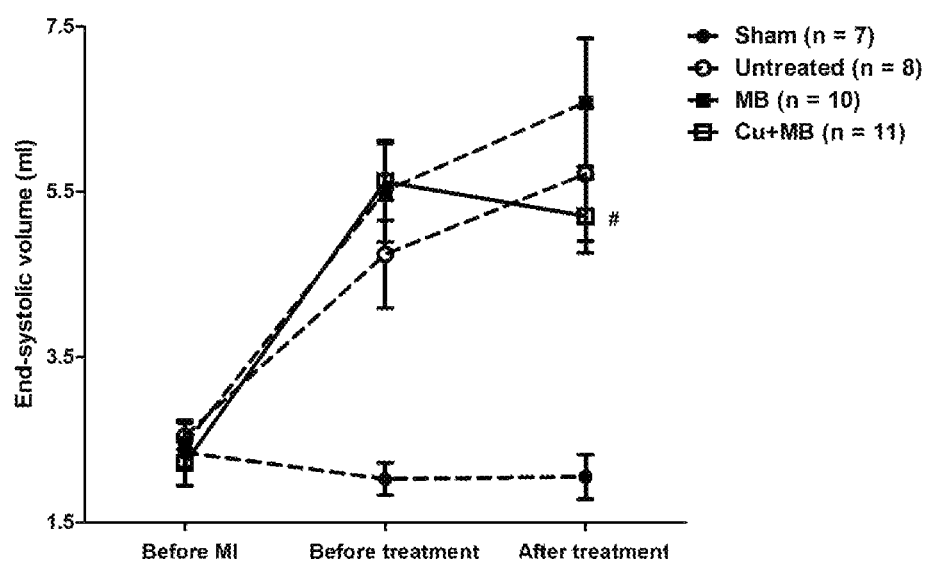
FIG. 17 shows echocardiography detected changes in left ventricular end systolic volume of Rhesus monkeys after treatment with Cu-MB.

Echocardiography examination showed that, after copper microbubble treatment, the left ventricular ejection fraction was increased significantly. However, in the untreated group and microbubble group, the left ventricular ejection fraction was decreased with time (FIG. 16A). And this recovery of cardiac performance was confirmed by MRI examination (FIG. 16B). Further investigation found that the improvement of the left ventricular ejection fraction was the result of the significantly decrease in end systolic volume of left ventricular (p<0.05). After each contraction of the left ventricular, the residual blood was conspicuously reduced in copper microbubble treatment group which means the systolic function of the left ventricular was improved significantly (p<0.05) (FIG. 17).

Figure 18A:
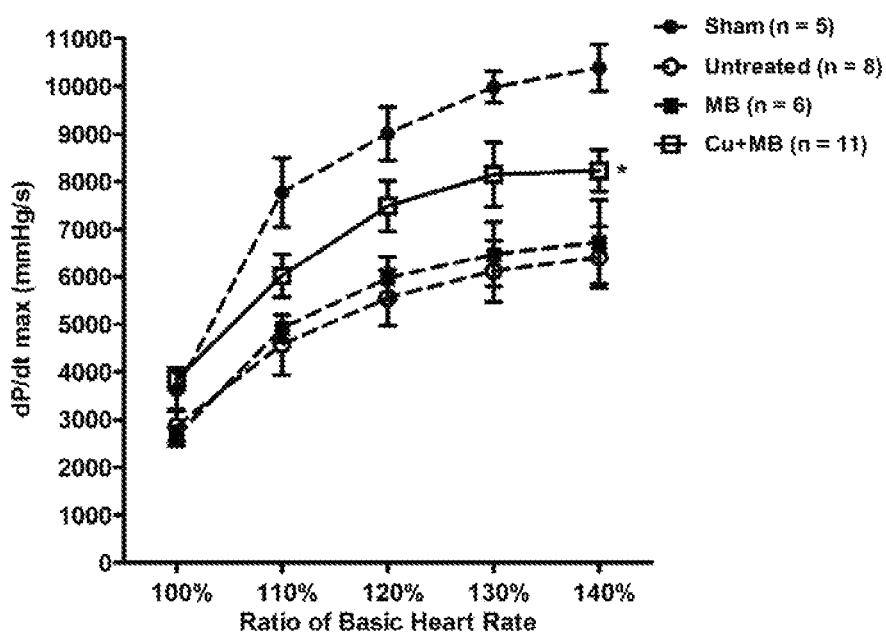
FIG. 18A shows max dP/dt detected by invasive cardiac hemodynamic measurement of Rhesus monkeys after Cu-MB treatment. Max dP/dt increase reflects the enhancement of cardiac systolic function.
Figure 18B:
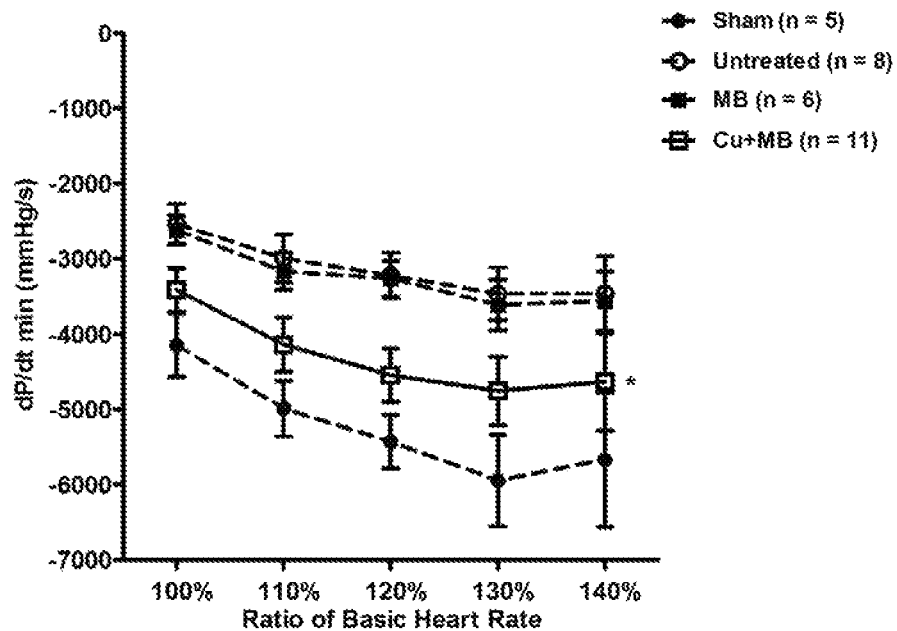
FIG. 18B shows min dP/dt detected by invasive cardiac hemodynamic measurement of Rhesus monkeys after Cu-MB treatment. Absolute value of min dP/dt increase reflects the enhancement of cardiac diastolic function.
Figure 19:
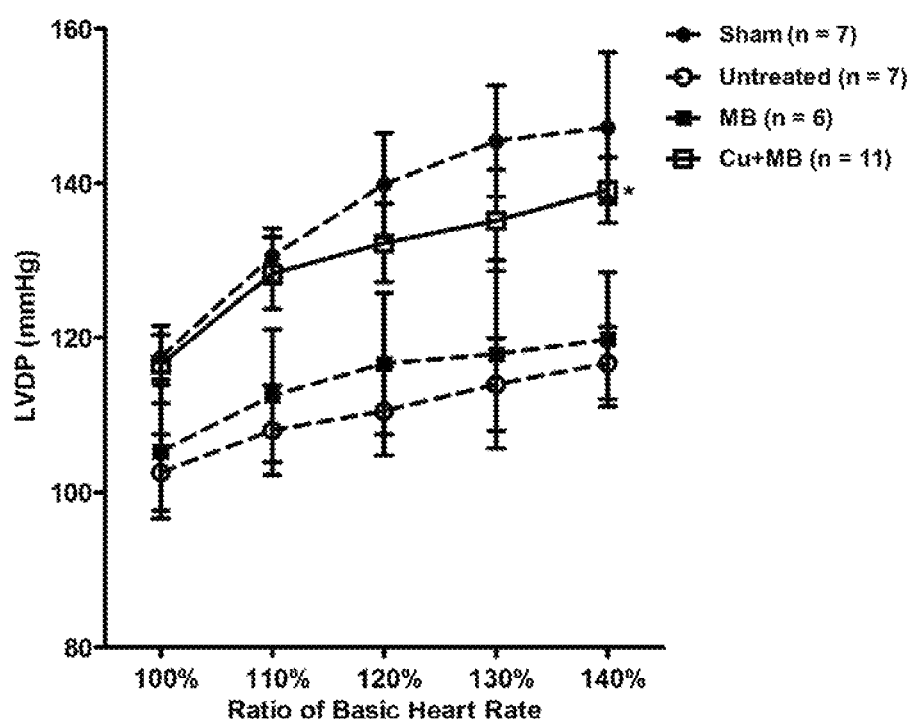
FIG. 19 shows left ventricular development pressure (LVDP) detected by invasive cardiac hemodynamic measurement of Rhesus monkeys after Cu-MB treatment. LVDP increase reflects the enhancement of cardiac systolic function.

Invasive hemodynamic measurement was performed under the drug stress condition. With the escalation of heart rate in response to the increase of dobutamine dose, the cardiac reserve parameters were evaluated at the heart rate elevation from 100% to 140% of the basal rate. As the absolute value of the dP/dt max, dP/dt min and the left ventricular development pressure (LVPD) increased, the cardiac reserve performance were improved. The invasive hemodynamic measurement showed that compared with untreated and microbubble treated group, the max dP/dt (FIG. 18A), min dP/dt (FIG. 18B) and the LVPD (FIG. 19) were improved significantly in the copper microbubble treatment group (p<0.05).

2.2 Infarction Size

Figure 20:
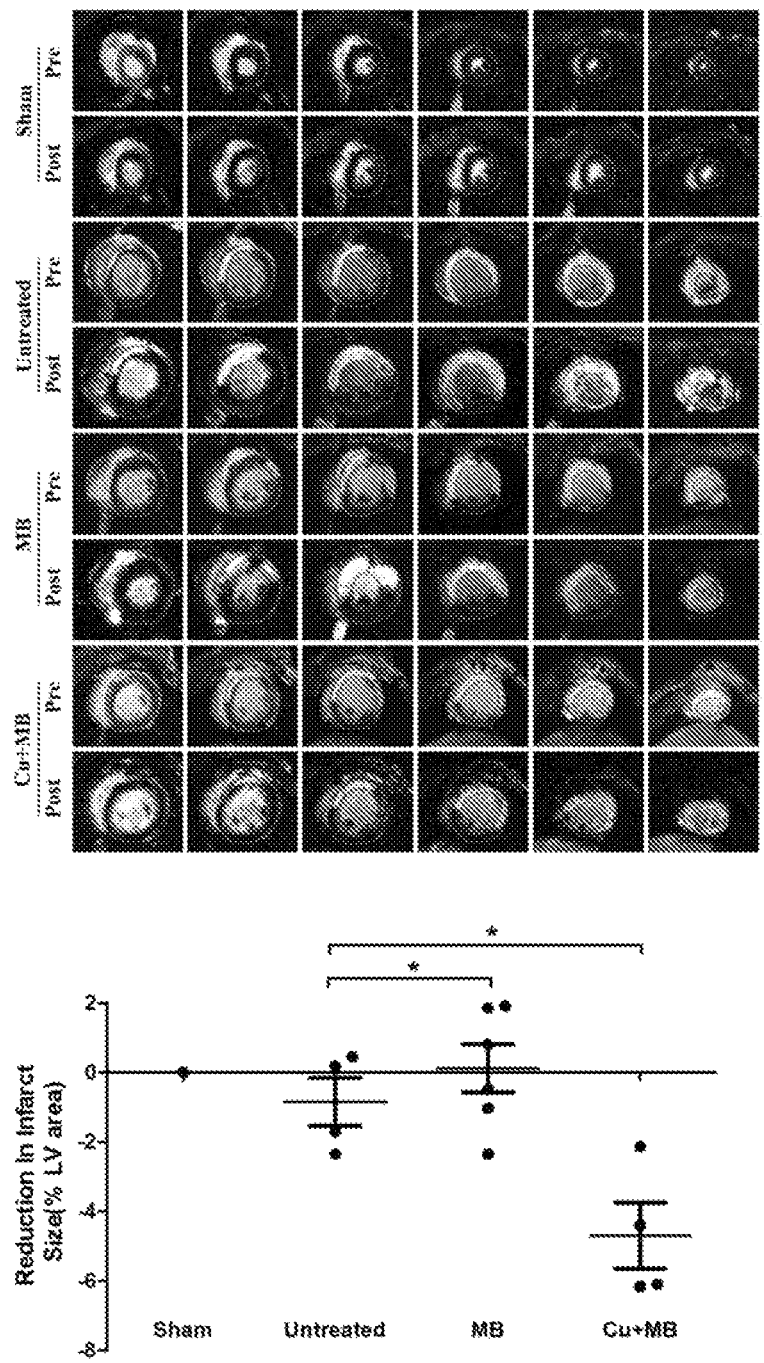
FIG. 20 shows MRI detected changes in infarction size of Rhesus monkeys after treatment with Cu-MB.

We estimated the effect of the treatment on infarct volume of myocardium gauged by magnetic resonance imaging (MRI) before treatment onset, and after two weeks of observation following the treatment. Comparison analysis showed that the infarct size in Copper-albumin ultrasound contrast microbubble (Cu+MB) treated group was obviously reduced compared with that of pre-treatment (FIG. 20). However, in the untreated and microbubble alone (MB) treatment groups, the infarction size exhibited no significant change. The results confirmed the therapeutic effect of the copper-albumin ultrasound contrast microbubble (CAUCM) treatment on reducing the infarct size in recovering ischemic hearts.

2.3 Immunohistochemistry

Figure 21:
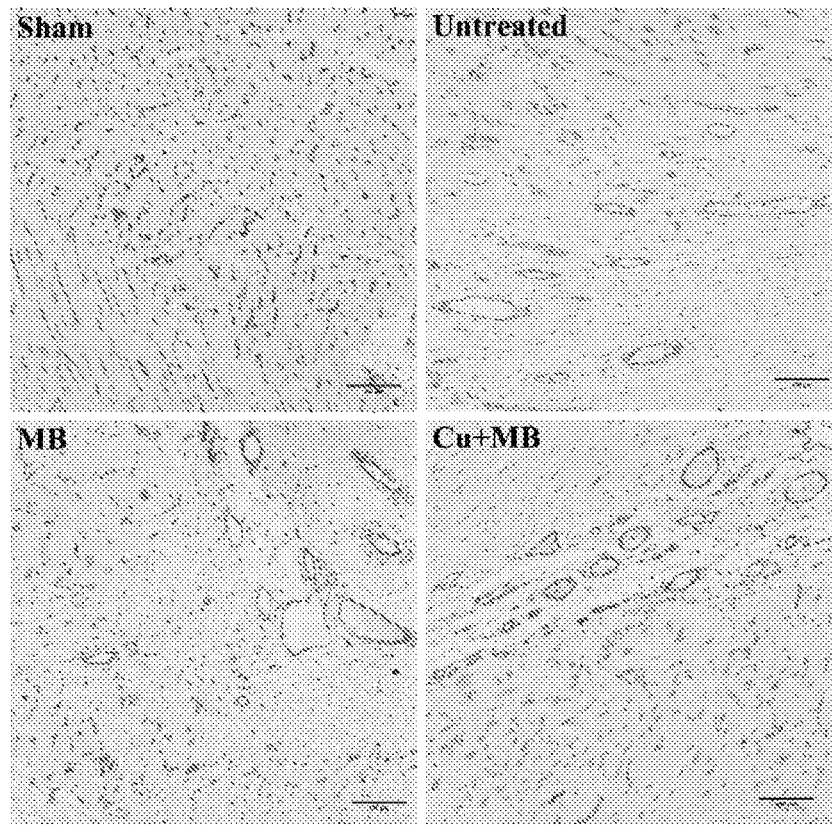
FIG. 21 shows CD31 labeled capillary density in the border of infarction area.
Figure 21:
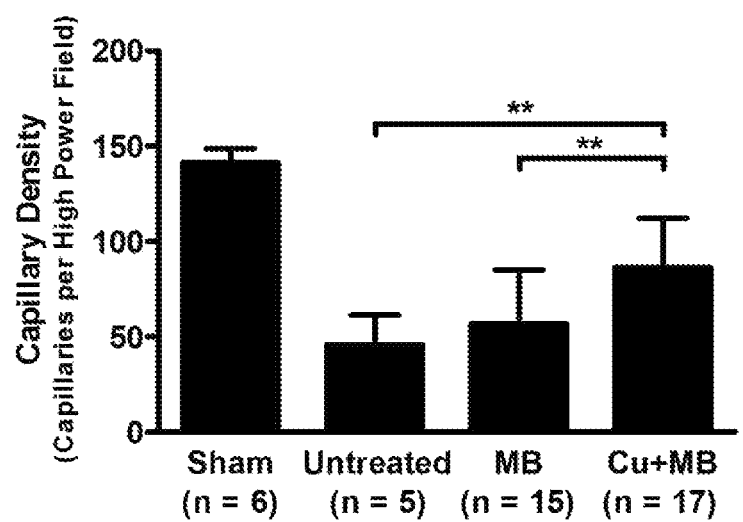
Figure 22:
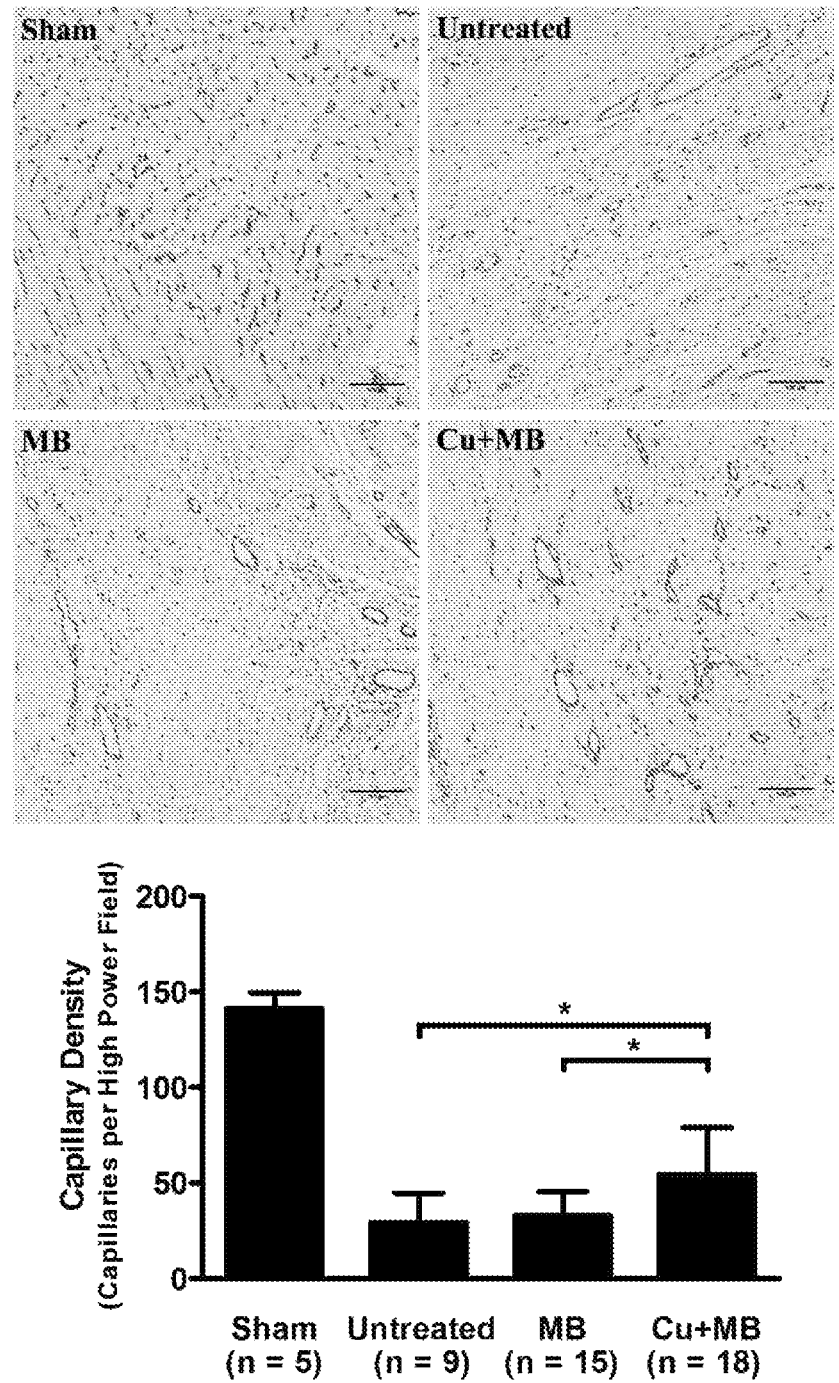
FIG. 22 shows CD31 labeled capillary density in infarction area of Rhesus monkeys.
Figure 23:
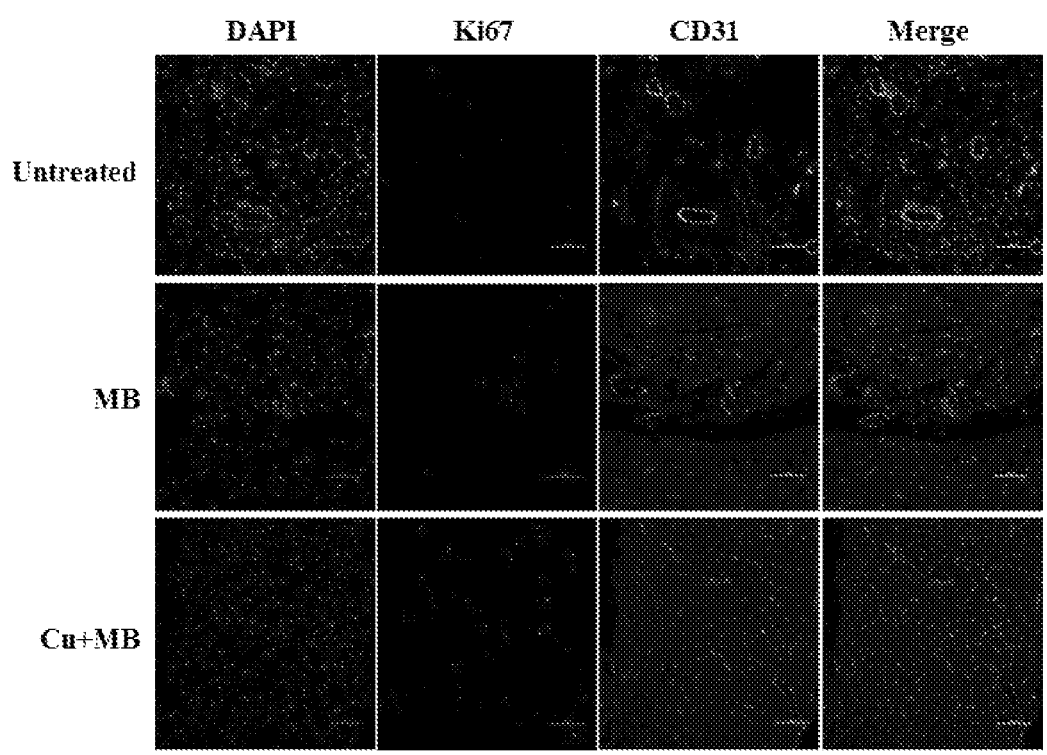
FIG. 23 shows Ki67 labeling of proliferative cells in infarction area after Rhesus monkeys treatment with Copper-albumin ultrasound contrast microbubble targeted therapy.

Capillary density: CD31 was a marker of endothelial cells. In the border area and infarct area immunohistochemistry examination showed that there were plenty of CD31 labeled capillaries in copper microbubble group (FIG. 21 and FIG. 22), and much more than untreated and microbubble group (p<0.05). Statistical graph of capillary density showed that CD31 labeled capillary density was significantly increased in the border area and infarct area after copper loaded microbubble treatment. ** means p<0.01. The local blood flow was improved significantly.

Figure 24:
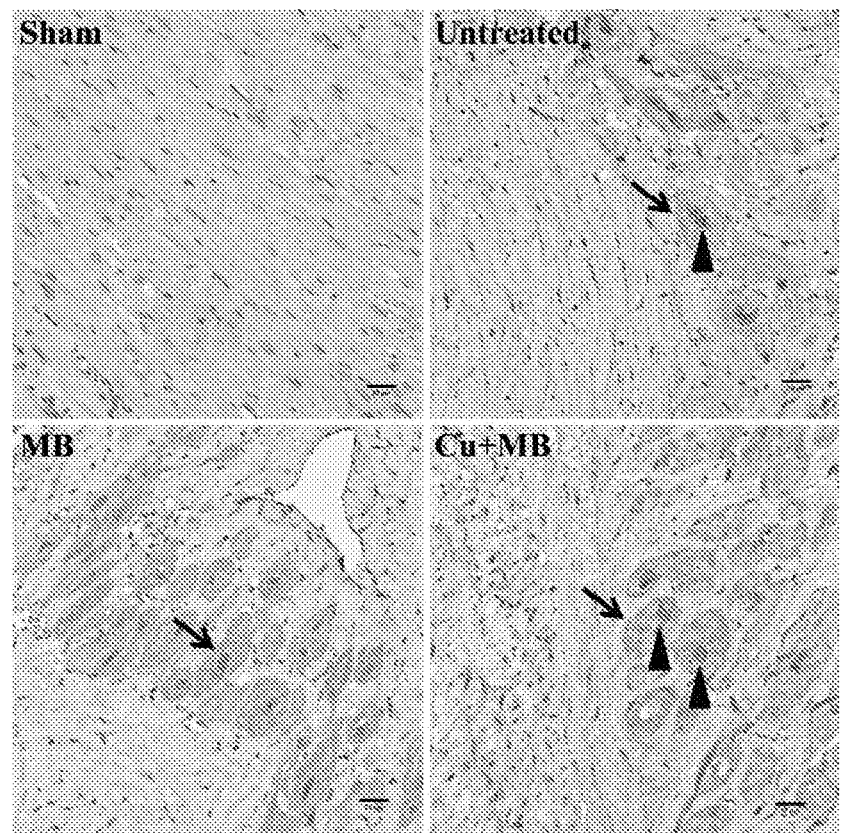
FIG. 24 shows the increase of HIF-1α protein levels in infarction area, with immunohistochemical staining showing HIF-1α expression in the cytoplasm and nucleus of myocardial cells and cytoplasm of endothelial cells.

Ki-67 positive cells were on behalf of cell proliferation activity by confocal. Data showed after copper loaded microbubble treatment, a lot of proliferation cells appeared in the infarct area. HIF-1α in the infarction area was detected by immunohistochemistry. Data showed HIF-1α was mainly located in the cytosol and nuclei of resident cardiomyocytes and endothelial cells. The level of HIF-1α was obviously up-regulated in the infarct area (FIG. 24). FIG. 24 showed HIF-1α was existed in the cytosol (arrow) and nuclei (arrow head) of cardiomyocytes, and endothelial cells. Expression of HIF-1α was up-regulated in infarct area.

Figure 25:
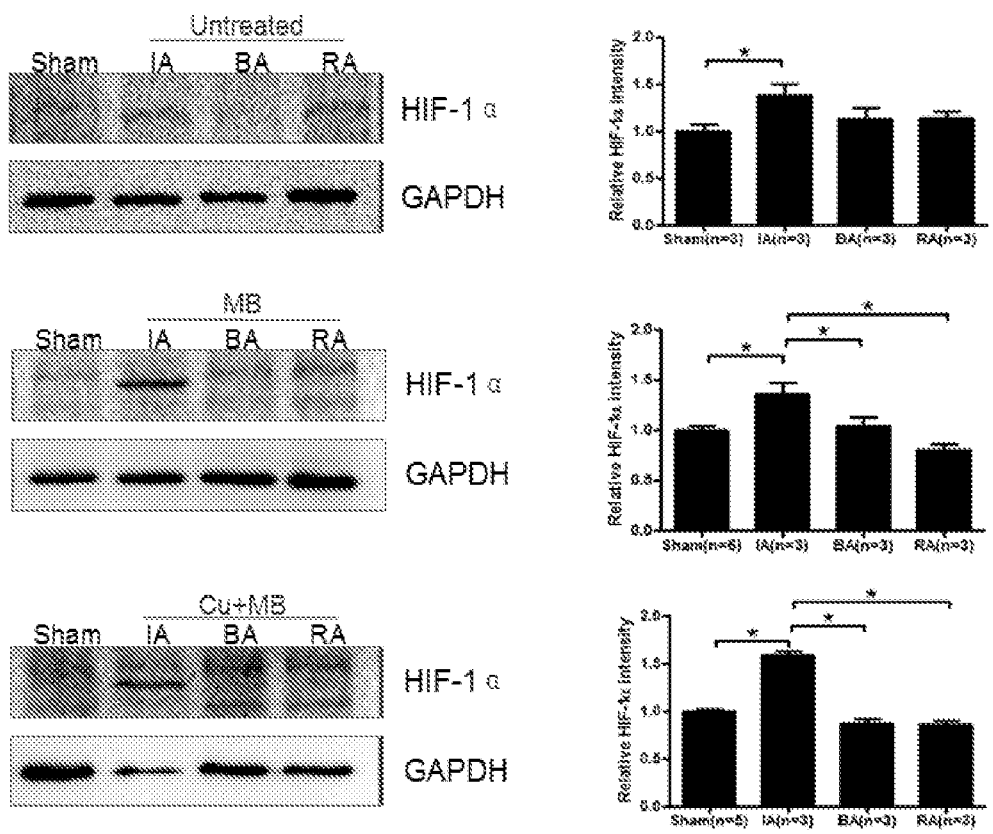
FIG. 25 shows Western-Blot showing the expression of HIF-1α protein in different cardiac area of different groups.
Figure 26:
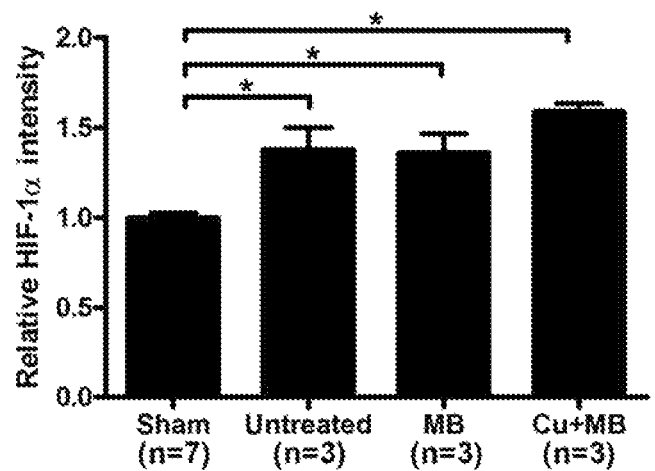
FIG. 26 shows Western-Blot showing the expression of HIF-1α protein in infarction area in different groups.

Protein level of HIF-1α increased significantly in the infarct area compared with other area as shown by Western blot method. FIG. 25 shows protein level of HIF-1α in different parts of each group, and FIG. 26 shows expression of HIF-1α in infarcted myocardium of each group.

Figure 27:
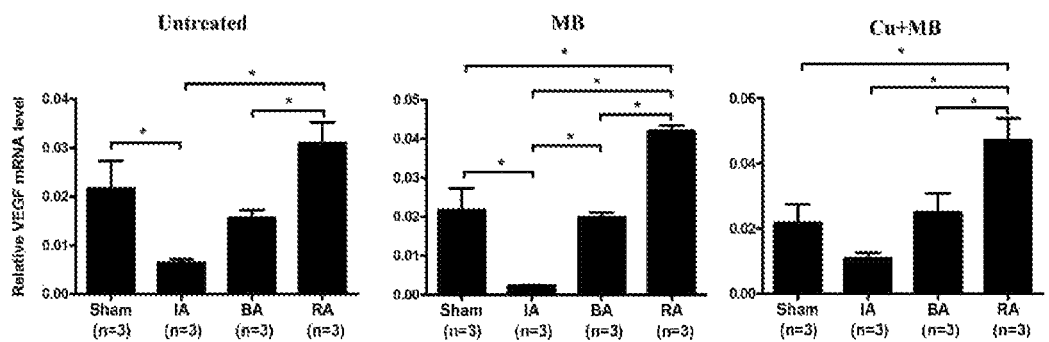
FIG. 27 shows RT-PCR results showing changes in the mRNA levels of cardiac VEGF in different cardiac area of different groups.
Figure 28:
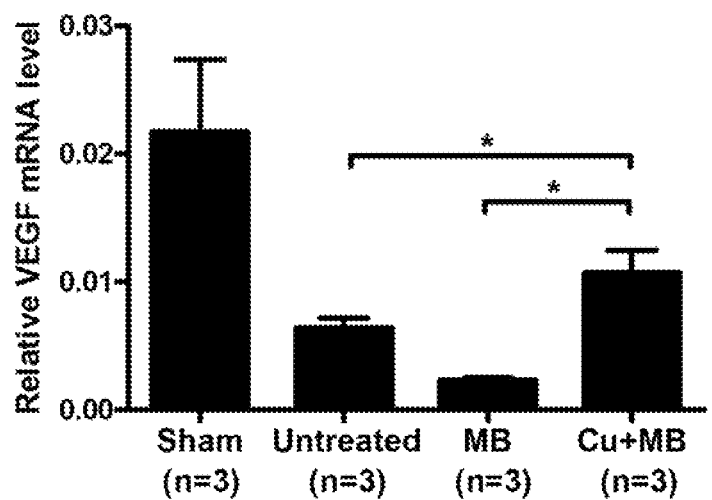
FIG. 28 shows RT-PCR results showing changes in the mRNA levels of cardiac VEGF in infarction area of different groups.
Figure 29:
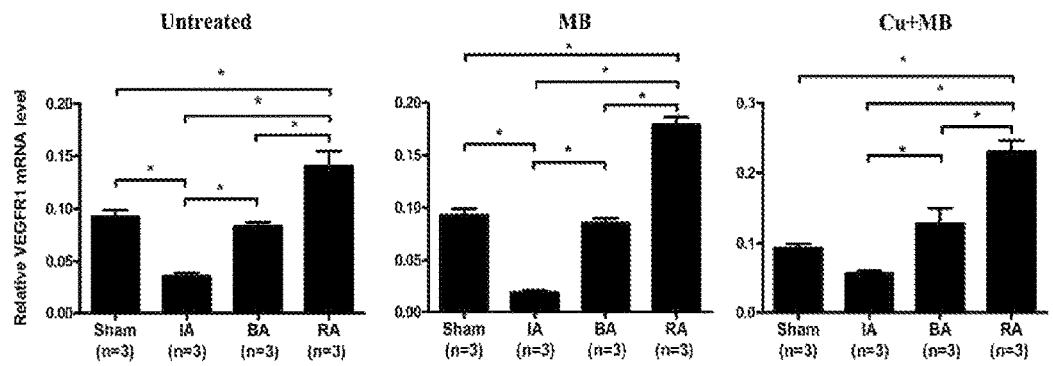
FIG. 29 shows RT-PCR results showing changes in the mRNA levels of cardiac VEGFR1 in different cardiac area of different groups.
Figure 30:
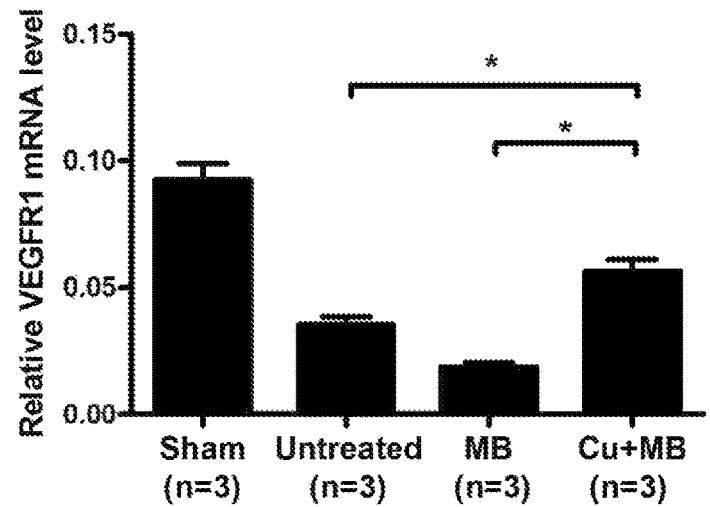
FIG. 30 shows RT-PCR results showing changes in the mRNA levels of cardiac VEGFR1 in infarction area of different groups.
Figure 31:
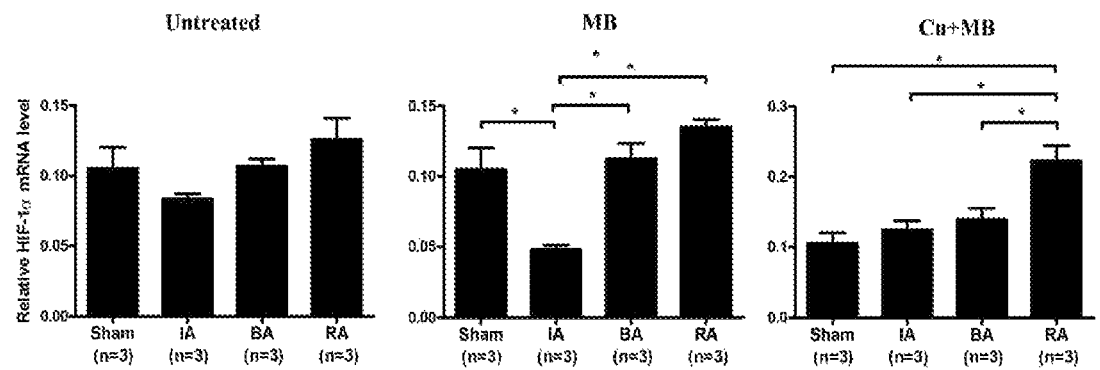
FIG. 31 shows RT-PCR results showing changes in the mRNA levels of cardiac HIF-1α in different cardiac area of different groups.
Figure 32:
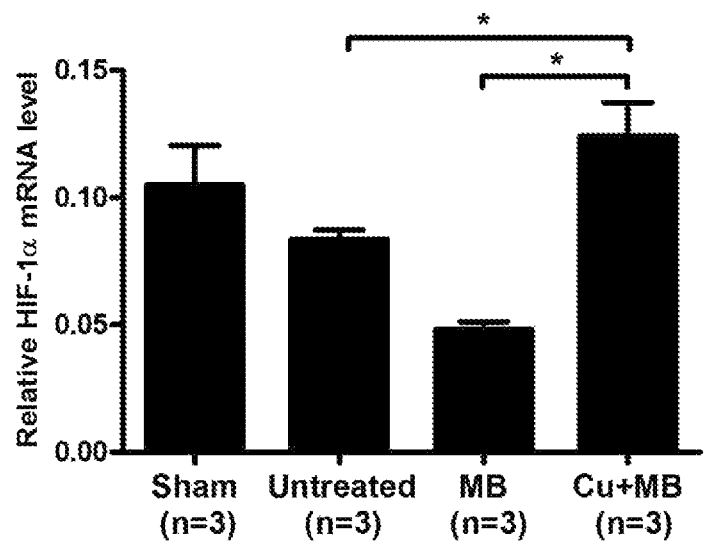
FIG. 32 shows RT-PCR results showing changes in the mRNA levels of cardiac HIF-1α in infarction area of different groups.

VEGF and VEGFR1 are HIF-1 controlled genes. mRNA level of VEGF and VEGFR1 were tested by RT-PCR to reveal transcription activity of HIF-1. As shown in FIG. 27 and FIG. 29, mRNA level of these two genes reduced markedly in untreated and MB groups, but increased significantly in Cu-treated group (FIG. 28, FIG. 30). This indicates that chronic hypoxia leads to depressed HIF-1 transcription activity which can be recovered by Cu treatment.

Figure 33:
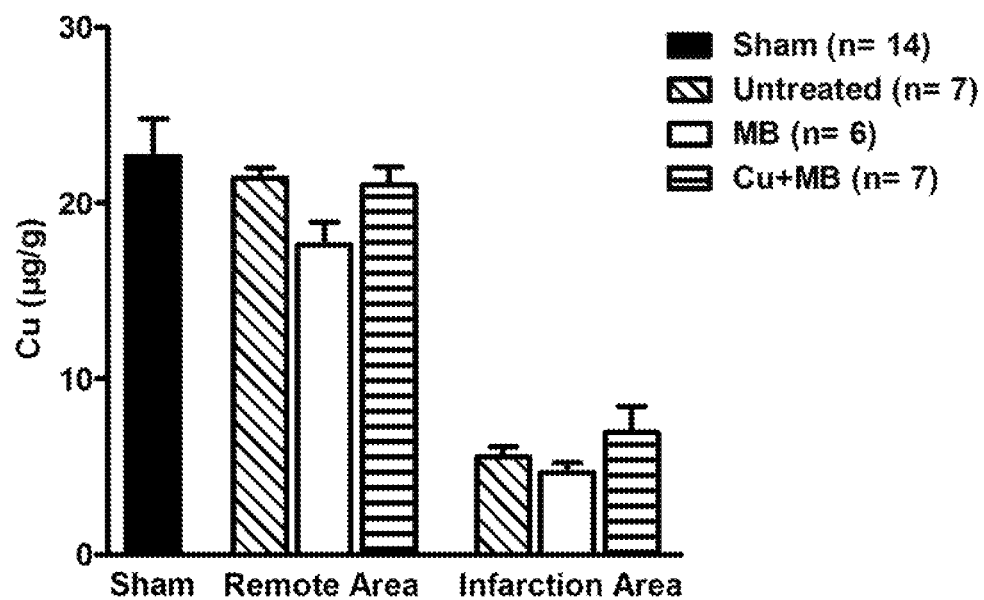
FIG. 33 shows copper content in the remote noninfarction area and infarction area in different treated groups.

Cu concentration in myocardium was determined by AAS. As shown in FIG. 33, Cu concentration increases after Cu treatment in ischemic myocardium.

The mechanism of HIF-1α accumulation in myocardial response to ischemic insult involves PHD modulations. PHD enzymatic activity requires oxygen, reduced iron, and 2-oxoglutarate. In addition, these enzymes are sensitive to oxygen availability affected by many metabolic changes, including reactive oxygen species generated by the electron transport chain and disturbance in mitochondrial metabolism and function. Therefore, the PHD proteins act as oxygen sensors, coupling changes in the HIF-1 transcriptional activity. The lack of oxygen in ischemic myocardium thus compromises the PHD function, which is accompanied with increased accumulation of HIF-1α- and HIF-1-responsive gene products. Acute myocardial ischemia leads to increased accumulation of HIF-1α and the expression of HIF-1-regulated genes, among which are those involved in angiogenesis. An early study has found increased HIF-1α and VEGF mRNA and protein in ventricular biopsy specimens from patients undergoing coronary bypass surgery who had pathological evidence of acute ischemia. In animal model studies, it was also found that a systemic ischemia led to widespread elevation of HIF-1α and coronary An early study using isolated rat hearts orthogradely perfused in the Langendorff configuration has produced direct evidence for substantial mobilization of copper in the coronary flow immediately following prolonged, but not short, cardiac ischemia. In the Langendorff perfusion of isolated rat hearts, the level of copper was 8- to nine fold higher than the preischemic value in the first coronary flow fraction (CFF) of reperfusion (0.15 mL) after 35 min of ischemia. The levels in subsequent CFFs decreased and reached the preischemic value, indicating that copper appears in a burst at the resumption of coronary flow. Following 18 min of ischemia, the copper level in the first CFF of reperfusion was only 15% over the preischemic value. The loss of copper in the first CFF correlated well with the degree of the loss of cardiac function. After 18 min of ischemia, cardiac function was about 50% and the damage was considered reversible, whereas after 35 min, the functional loss exceeded 80% and was considered irreversible. Therefore, the loss of copper after a prolonged ischemia in the heart would directly result from ischemic toxicity.

The increase in homocysteine levels in myocardial ischemia has been known for a long time and considered to be a risk factor for myocardial pathogenesis. It has been observed that the blood copper and homocysteine were simultaneously elevated in patients with cardiovascular disease. It is reasonable to speculate that copper efflux from the heart is related to homocysteine. There are several lines of evidence that indicate the interaction between copper and homocysteine. First, it has been invariably observed that hyperhomocysteinemia is associated with high concentrations of blood copper as well as ceruloplasmin. Second, copper and homocysteine complexes have been identified in vitro. Third, copper supplementation restores copper-dependent enzyme activity under the condition of homocysteine exposure. These observations collectively suggest that the interaction between copper and homocysteine may be responsible for cardiac copper efflux.

Copper is capable of stabilizing HIF-1α by a mechanism involving the inhibition of prolyl hydroxylases. However, this action of copper would be as the same as other transition metals such as cobalt and nickel, which are not essential for HIF-1 activation, but enhance HIF-1 activity when the cells are exposed to excess amount of these transition metals. Our studies have shown that copper is required for HIF-1 transcriptional activity. Copper chelation in cultured cells blocks IGF-1-induced HIF-1 binding to hypoxia-responsive element (HRE) and VEGF expression. This inhibitory effect can be relieved by addition of excess copper in cultures. In addition, we have found that this copper action depends on a copper chaperone for Cu, Zn-superoxide dismutase (CCS) and CCS gene silencing blocks IGF-1-induced HIF-1 HRE binding and VEGF expression, mimicking the effect of copper chelation. Furthermore, CCS directly interacts with HIF-1α, as revealed by an immunoprecipitation assay.

There are multiple sites that potentially require copper for activation of HIF-1, including HIF-1α synthesis, stabilization, translocation from cytosol to nucleus, binding to the HRE sequence of target genes, and HIF-1 transcriptional complex formation. We have specifically determined the mechanism of action of copper in regulation of HIF-1 transcriptional activity in human hepatoma HepG2 cells. Treatment of HepG2 cells with a copper chelator tetraethylenepentamine (TEPA) or siRNA targeting CCS suppressed hypoxia-induced activation of HIF-1. Addition of excess copper relieved the suppression by TEPA, but not that by CCS gene silencing. This CCS gene silencing result excludes possible confounding effect on nonspecific chelation by TEPA. Therefore, the data indicated that copper is required for the activation of HIF-1, but the action is CCS-dependent. Copper deprivation did not affect production or stability of HIF-1α, but reduced HIF-1α binding to the HRE sequence of target genes and to p300, a component of HIF-1 transcriptional complex. Copper likely inhibits FIH-1 to ensure the formation of HIF-1 transcriptional complex. Therefore, it was concluded that copper is required for HIF-1 activation through regulation of HIF-1α binding to the HRE and the formation of HIF-1 transcriptional complex. Copper deficiency thus suppresses HIF-1 transcriptional activity by FIH-1 depression.

As a proof of concept, we have done a study using dietary supplementation with copper for mice of hypertrophic cardiomyopathy. The mice were subjected to pressure overload by ascending aortic constriction, and cardiac hypertrophy was developed 4 weeks after the procedure. Dietary supplementation with physiologically relevant levels of copper started after the cardiac hypertrophy had developed. At 4 weeks after copper supplementation, it was found that the pre-established hypertrophic cardiomyopathy was reversed and this reversal occurred in the continued presence of pressure overload. Sustained pressure overload led to decreases in cardiac copper and VEGF levels along with suppression of myocardial angiogenesis. Copper supplementation replenished cardiac copper, increased VEGF, and promoted angiogenesis.

Figure 34:
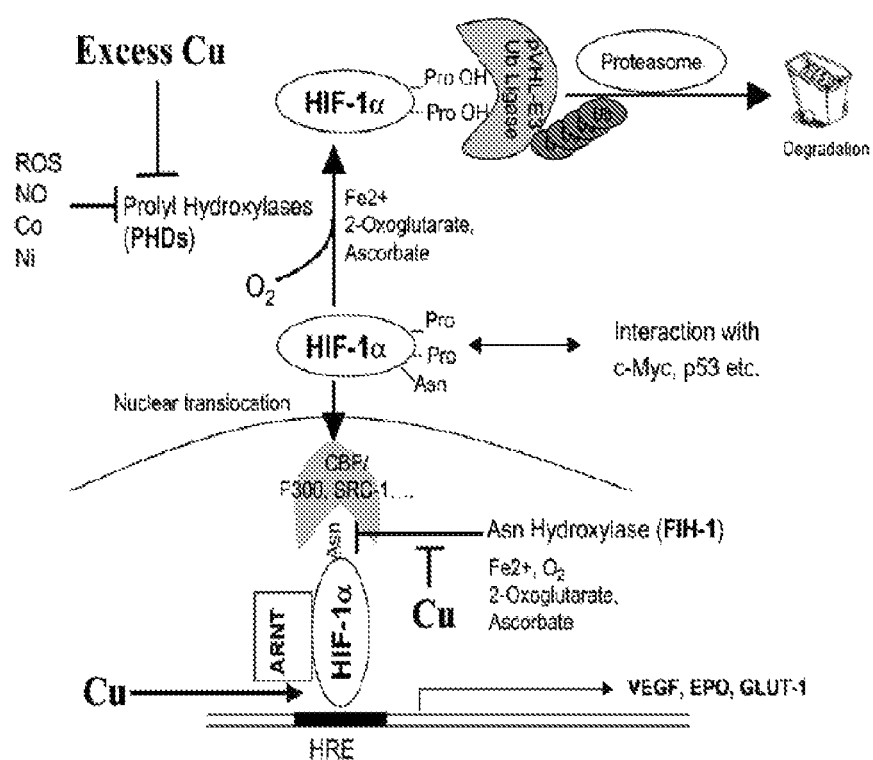
FIG. 34 shows a mechanism of the copper loss inducing the depression of HIF-1 activity.

HIF-1 is composed of a constitutively expressed HIF-1β (ARNT) and HIF-1β (or HIF-2β), which is subjected to two-step (cytosolic and nuclear) hydroxylation regulation under aerobic conditions. In the cytosol, HIF-1β is subjected to prolyl hydroxylation by three major prolyl hydroxylases (PHDs), which use O2 as a substrate. The hydroxylized HIF-1β binds to the von Hipple-Lindau protein (pVHL), which targets HIF-1β for ubiquitination and proteasomal degradation. In the nucleus, RIF-1β interacts with the co-factors SRC-1, CBP and p300, which is inhibited by an asparagine hydroxylase or factor inhibiting HIF-1 (FIH-1). FIH-1 also is an O2-dependent enzyme. Under hypoxia conditions, the PHDs and FIH-1 are inhibited, leading to the escape of proteasomal degradation of RIF-1β and the facilitation of RIF-1 transcriptional complex formation, and thus activation of the transcription factor. Co and Ni have been shown to inhibit PHDs, thus mimicking the conditions of hypoxia, leading to RIF-1β activation. Excess Cu also inhibits PHDs causes the same effect on RIF-1β as do Co and Ni. However, Cu is required for the interaction between RIF-1 and HRE, and acts as a physiological inhibitor for FIH-1 to ensure the HIF-1 complex transcriptional complex formation. Therefore, Cu deprivation inhibits HIF-1 activity (FIG. 34).

Myocardial ischemia leads to HIF-1α accumulation and copper depletion. Under this condition, the accumulation of HIFα cannot be converted to HIF transcriptional activation because copper is required for HIF transcriptional complex formation and for HIF interaction with HRE sequence in target genes. Therefore, although HIF accumulation takes place in ischemic myocardium, copper deficiency blocks HIF-regulated expression of genes involved in angiogenesis, leading to suppression of myocardial angiogenesis. This results in myocardial infarction and further progresses to heart failure.

Thus, the present study was conducted by targeted delivery of copper through ultrasound triggering copper microbubble exploded to increase the copper content of local ischemia area for myocardial infarction treatment. The results showed that, the transcription activity of HIF was increased in the infarction area; the capillary density was also increased significantly. Furthermore, echocardiography examination showed that the cardiac function was improved after copper microbubble treatment. In addition, the cardiac reserve was enhanced correspondingly in the copper treatment group. The results of this experiment provided strong evidence that this ultrasound induced copper microbubble explosion will be novel strategy to deliver copper for treatment of myocardial infarction.

Example 3

Treatment of Ischemic Brain Injury in Rats by Copper-Containing Biological Materials In order to explore a new method for the treatment of cerebral ischemia, this example utilizes copper nanomaterials to treat ischemia rat model to test the therapeutic effect on angiogenesis.

1. Experimental Methods 1.1 Establishment of Rats Ischemia Model

Healthy male Sprague-Dawley (SD) rats body weight 270±15 g) were raised in the room with constant temperature and humidity and 12 hours alternation of light-dark cycle. The rats were treated with preoperative fasting for 12 hours and free supply of drinking water.

1.2 Technical Routes

Rats were divided into 5 groups randomly: Sham group, IR group, IR+Cu group, IR+NM group, IR+Cu–NM group. Brain ischemia rats were respectively injected with the same volume of Cu, NM, Cu–NM material 10 mu (L) into the stereotaxic ventricle on 7 days after surgical operation, and nerve function score and TTC staining was performed in 14 days. Then brain tissue was fixed by 4% paraformaldehyde for immunohistochemical detection.

1.3 The Preparation Steps of the Middle Cerebral Artery Occlusion and Reperfusion Model (MCAO)

Anesthesia was induced by 10% chloral hydrate (0.35 ml/100 g) intraperitoneally injection, without the trachea cannula and breathing machine. When rats without limbs movements, respiratory rate around 30-60 times, eyes kept closely, rats were thought to be anaesthetize successfully. The following procedures were conducted as Koizumi and Longa method (Koizumi et al, 1986, Longa E Z, 1989), suture-occluded method, to make the middle cerebral artery occlusion model with an improved suture. Traditional method was conducted with a 4-0 nylon monofilament suture, the tip of which was rounded by a flame heating, with the diameter 0.20-0.25 mm. Because the tip was not big enough, the blood vessel can't be blocked completely, resulting in the backflow. The modified suture, with the diameter of 0.32 mm and a 5 mm tip covered by silica gel, was marked at 18 mm. The outside of the suture covered with the silicone in the tip could rub against the inter wall of the vessel compatibly without leaking. Therefore, the rate of the backflow reduces so as to elevate the success rate of the model.

Rats were placed on the operating table after anesthesia. Rectal temperature was maintained at 37.0° C. with a heating pad during the surgical procedure. The neck hair was shaved, surgical area was disinfected with povidone-iodine, and deiodinated with 75% ethyl alcohol, and sterile surgical drapes was prepared. After slicing off the neck skin along the median anterior line by tissue scissors, 3 cm length, the neck muscle and thyroid gland were separated bluntly by vessel clamp, until exposing the common carotid artery (CCA), and then separating the total artery upward along the carotid artery to reveal the external carotid artery (ECA), internal carotid artery (ICA). Ligaturing the far-end of the ECA, the carotid artery blood flow was blocked with temporary folder, and a small incision was made in the CCA. The suture was inserted into the CCA through the small incision, and then gently advanced slowly along the CCA, and blocked until reached obstruction induced by the temporary folder. Then the temporary folder was opened, the suture was pushed immediately into the internal carotid artery. If the resistance was felt during the suture advanced, the suture tip was entered in the anterior cerebral artery, and the side wall of the suture has occluded the middle cerebral artery, and the suture should be stopped to avoid the suture entering into the pterygopalatine artery. The pterygopalatine artery is the external cranium branch of the ICA. The suture should not be advanced at a deepness of 10 mm if it has been inserted in the pterygopalatine artery. Withdrawing the suture and regulate the direction properly, it could be inserted into the ICA again. Next procedure was followed as suturing muscle and skin incision iodine disinfection, sterile dressing covered the rats in 33° C. humidity chamber to promote anesthesia recovery. 90 min after MCAO, anesthesia was carried out again, and the suture was extracted for blood reperfusion. Stopping pulling out the suture when the resistance was felt. The resistance demonstrates the tip of the suture have arrived to the crotch of the common carotid artery, then cutting off the suture outside the skin. Maintaining the body temperature and normal saline supplement is necessary. 400000 units of penicillin were intramuscular injected to prevent the infection.

1.4 Post-Operation Cerebral Injury Evaluation

Neurological severity scores: Ideal MCAO rat showed different degree neurological dysfunction after the consciousness recovers. Fore limb hemiplegia was the main symptom, transferring the head to the contralateral body, circling or dumping when they climbs, the body bend to one side and posterior limbs bended when the model left up also happened. The survival rate was counted during the observation.

Neurological dysfunction score are performed after the rats wake back. 18 points scoring criteria was used in this experiment, Table 3. MNSS scoring system (a total of 18 points) was divided into: 1.Sports (6 scores): observing the flexion degree of the contralateral fore limb when the tail is lift up. 2. Feeling (2 scores): deep and shallow sensation. 3. Balance beam test (6 scores): observing the balance status after the ischemia to adjust the degree of the neurological defect. 4. Reflection (4 scores): including the reflection of pinna, cornea, scare, and convulsion and so on. '0' indicates normal, '18'meas most serious. Mild injury: 1-6; moderate injury: 7-12; severe injury: 13-18. After ischemia and reperfusion without apparent neurological dysfunction, the rats were excluded from the study after 24 hours of reperfusion.

TABLE 3

Modified Neurological Severity Score points

| Classification | Score |
|---|---|
| Motor tests | |
| Raising rat by tail (3) | |
| Flexion of forelimb | 1 |
| Flexion of hindlimb | 1 |
| Head moved >10° to vertical axis within 30 s | 1 |
| Placing rat on floor (normal = 0; maximum = 3) (3) | |
| Normal walk | 0 |
| Inability to walk straight | 1 |
| Circling toward paretic side | 2 |
| Falls down to paretic side | 3 |
| Sensory tests (2) | |
| Placing test (visual and tactile test) | 1 |
| Proprioceptive test (deep sensation, pushing paw against table edge to stimulate limb muscles) | 1 |
| Beam balance tests (normal = 0; maximum = 6) (6) | |
| Balances with steady posture | 0 |
| Grasps side of beam | 1 |
| Hugs beam and 1 limb falls down from beam | 2 |
| Hugs beam and 2 limbs fall down from beam, or spins on beam (>60 s) | 3 |

TABLE 3-continued

Modified Neurological Severity Score points

| Classification | Score |
| --- | --- |
| Attempts to balance on beam but falls off (>40 s) ) | 4 |
| Attempts to balance on beam but falls off (>20 s) | 5 |
| Falls off; no attempt to balance or hang on to beam (<20 s) | 6 |
| Reflex absence and abnormal movements (4) | |
| Pinna reflex (head shake when auditory meatus is touched) | 1 |
| Corneal reflex (eye blink when cornea is lightly touched with cotton) | 1 |
| Startle reflex (motor response to a brief noise from snapping a clipboard paper) | 1 |
| Seizures, myoclonus, myodystony | 1 |

Measurement of the infarction area: TTC (2, 3, 5-chlorination triphenyl tetrazolium) reaction with the succinodehydrogenaseos of the mitochondria was used to detect the activity of the cell. TTC stain marked the ischemic injured brain slices as white. TTC stain (2%) was performed without light, under conditions of 37° C. The brain samples were harvested at different time (18 per group) and put on the tissue slice mould, which was stored in the −20° C. before. The brain was cut into 6 slices from the olfactory bulb to the occipital lobe in the slice mould after 10 min freeze, with a thickness of 2 mm per slice. Then the slices was immersed into the 2% TTC and put into the 37° C. incubator for 30 min, and then fixed overnight in the 10% paraformaldehyde.

TTC staining showed which part of the brain tissue slices experienced hypoxia. Because of this, the TTC labeled scope of brain injury was widely used in detection of brain ischemic size. Each slice image was collected through a digital camera (Powershot 400 digital camera, Canon Corp) and processed using Image J software to calculate the area of brain injury. At the same time, we used the modified formula to exclude the deviation resulted from the effects of brain edema on the actual volume of brain injury: the corrected (%)={[contralateral hemisphere area−(injured hemisphere area−brain damage area)]/contralateral hemisphere area}×100%.

Determination of index of brain atrophy: this experiment was conducted to research the change of cerebral infarction in chronic phase, the brain infarction area displayed different degree of atrophy in 10 days, and it was most obvious in 14 days. The calculation of the brain atrophy degree was similar to the calculation of cerebral infarction area. Cerebral infarction hemisphere brain shrinkage index (%)={(hemisphere volume−the contralateral hemisphere infarction volume)/the contralateral hemisphere volume}×100%.

1.5 Preparation of Copper Biological Materials

This example designed short peptide materials with $Cu^{2+}$ binding sites (composed of histidine, arginine and glycine). The short peptide can combine with $Cu^{2+}$ to form stable hydrogel samples composed of nanofibers nano biological materials (Cu-NM, containing 80 μM CuSO4). Cu-NM has a function to release $Cu^{2+}$ slowly in specific location of injury tissues and organs and promote ischemic injured tissue organ regeneration by effectively utilizing the copper biological function, meanwhile, eliminating the side effects of copper ion on normal tissues and organs.

1.6 Intraventricular Injection of Copper-Nanometer Materials by Stereotaxic Technique Rat Lateral ventricles location: Coronal plane anatomy map showed that the lateral ventricles of the rat located 0.8 mm back to bregma, 1.5 mm laterally to the midline, 4-4.5 mm depth. This location is the optimal injection site of the medicine.

7 day after cerebral ischemia/reperfusion, Rats were anesthetized by intraperitoneal injection of 10% chloral hydrate (3.5 ml/kg). Rats were fixed on the stereotaxic apparatus after anesthesia and the parietal region hair was shaved. After common sterilization and paving the aseptic towel, a 1 cm incision was carried out on the skin along the median line to expose the bregma. A tiny hole was drilled 1.5 mm laterally to midline, 0.8 mm back to the bregma on the skull, without injury of the brain tissue. 10 μl Cu-NM material was extracted by syringe, which was fixed and regulated to adjust the position of the needle tip. Then the needle tip of syringe was inserted into the tiny hole and injected into the brain tissue, stopped at the deepness of 4.5 mm. The Cu-NM material was injected, 5 min after the injection is over, the syringe was withdrawn, and the tiny hole was sealed by bone wax. The skin incision was sutured. Meanwhile, 10 μL Cu was injected in the Cu therapy group, and 10 μL nanometer material was injected in the material group, no treatment in the sham group and control group. Neurological function score and TTC staining were performed to measure the infarction volume and atrophic degree of the brain at 14 day after treatment.

1.7 Pathology Detection

Cu, NM, Cu-NM was injected into cerebral ventricle in one week after building cerebral ischemia/reperfusion model. The brain tissue was harvested in one week after treatment (five rats in each group). After anesthesia, we perfused heart with 0.9% saline and 4% paraformaldehyde, then removed the brain tissue quickly, fixed it in 4% paraformaldehyde. The slice of brain was selected at the level of optic chiasma coronal section, then dyed as follows.

HE staining: specimens were fixed with 10% neutral formalin, dehydrated, paraffin, and paraffin embedding. Slides and coverslips were soak with nitric acid overnight, and cleaned by tap water and distilled water, then wiped with anhydrous alcohol and positioned in dust-free place. After dried in 37° C., slides were treated with poly lysine tablets. The embedding routine paraffin was 4 μm in serial section, then dried in 60° C. oven. The brief steps of conventional H&E staining were: (1) taking the tissue slices (4 μm) embedded in paraffin off the paraffin hydration. (2) tissue slices were disseminated in Harris hematoxylin for 5 min, and washed by water for 1 min. (3) tissue slices were differentiated by 75% hydrochloric acid ethanol for 30 s, washed by water for 1 min. (4) tissue slices were treated by ammonia for 30 s, and washed by water for 1 min. (5) tissue slices were dyed in acid eosin ethanol for 12 min. (6) tissue slices were washed by quick water. (7) tissue slices were dehydrated to make slices transparent. (8) fixing slices by neutral gum. Then pathological changes in the cerebral infarction area were observed and compared with the contralateral brain tissue.

Immunohistochemistry: it was conducted to detect angiogenesis. Areas detected included infarction district, surrounding areas of infarction and the contralateral normal brain tissue. After labeled blood vessel with CD31, we inspected angiogenesis in cerebral ischemia after intervention by copper nano materials. The brief steps of immunohistochemistry: (1) The tissue slices (4 μm) were embedded in paraffin off the paraffin wax. (2) Quenched endogenous peroxidase with 3% H2O2 (hydrogen peroxide) (3) Blocked them by 10% rabbit serum for 30 minutes at room temperature. (4) Incubated in goats to rat CD31 first polyclonal antibody (1:2000) under the 4° C. overnight. (5) After washing, the slice was incubated in goats to rat CD31 second polyclonal antibody (1:2000) for 1 hour. (6) Incubated in horseradish peroxidase-avidin in composite enzyme (1:200). (7) Stained in diamino biphenyl ammonia (DAB).

1.8 Statistical Treatment

Data were statistically analyzed by SPSS14.0 (SPSS, Chicago, Ill.) software measuring index in all results is mean±standard deviation (X±SD), two groups are compared by t test. Multiple groups were compared by analysis of variance (ANOVA), LSD test and variance. Equal variance was not assumed, it can be corrected by Games-Howell method. $\alpha=0.05$ for the inspection level, $P<0.05$ for the significant statistical difference.

2. Experimental Results 2.1 Post-Operation Observation, the Success Rate of Modeling and Survival Rate The suture was inserted through the internal carotid artery, and withdrawn after 90 min, to produce the cerebral ischemic/reperfusion model. When the rats recovered from the anesthesia status, they showed the symptom including head turning to the contralateral body, forceless contralateral fore limb, circling to the contralateral direction or dumping, contralateral fore limb drooping when the tail was lift up. Among the 300 MCAO models, 210 models was successful (a success rate of 70%), and 30 models was unsuccessful (10%), and 60 rats died (20%), Table 4.

TABLE 4

Modeling situation of rats

| | Success | Failure | \multicolumn{4}{c}{Death} | Total |
|---|---|---|---|---|---|---|---|
| | | | SAH | encephaledema | operation | others | |
| Rate | 210 | 30 | 18 | 24 | 10 | 8 | 300 |
| | 70% | 10% | 6% | 8% | 3% | 3% | 100% |

Reason analysis: 22 rats didn't appeared limb function defect, and 8 rats showed mild paralysis symptom, recovering after 24-48 hours. The possible reasons were insufficient suture deepness, which caused the appearance of the gap between the lateral wall of the suture and the internal wall of the vessel, and resulted in the blood flowing into the middle cerebral artery. The second reason was that the suture was extracted during the skin incision closing, which leaded to the insufficient occlusion. Thirdly, Mutation of blood vessels contributed to better tolerance for the ischemia injury, with shorter time of neurological function recovering. TTC stain demonstrated only some small infarction appears in the basal ganglia region in this kind of rats after MCAO. Unsuccessful model are excluded during the experiment.

Fourthly, subarachnoid hemorrhage: because of the excess deepness of the suture, oversize power for suture advancing, the vessel was punctured by the suture, which caused the subarachnoid hemorrhage. By autopsy, 18 rats (30% of the total death rats) died from the subarachnoid hemorrhage. Serious cerebral infarction: the excessive deepness of the suture caused the serious cerebral ischemia and infarction. TTC stain showed that 24 rats (40% of the total death rats) died from the serious edema of the brain, with the edema of the whole cerebral hemisphere. Weasand and vagus were damaged during the operation: injury of the vagus caused a mass of secreta in the respiratory tract, which resulted in the respiratory hypoxia. 10 rats (16.7% of the total death rats) died from this reason.

Unexplained death: unexplained death in rats appeared in the process of breeding after surgery. We did not find significant cause of death by anatomy or TTC staining after death. There were 8 rats in this group, accounting for 13.3% of all deaths.

2.2 Neural Deficit Scores

Figure 35:
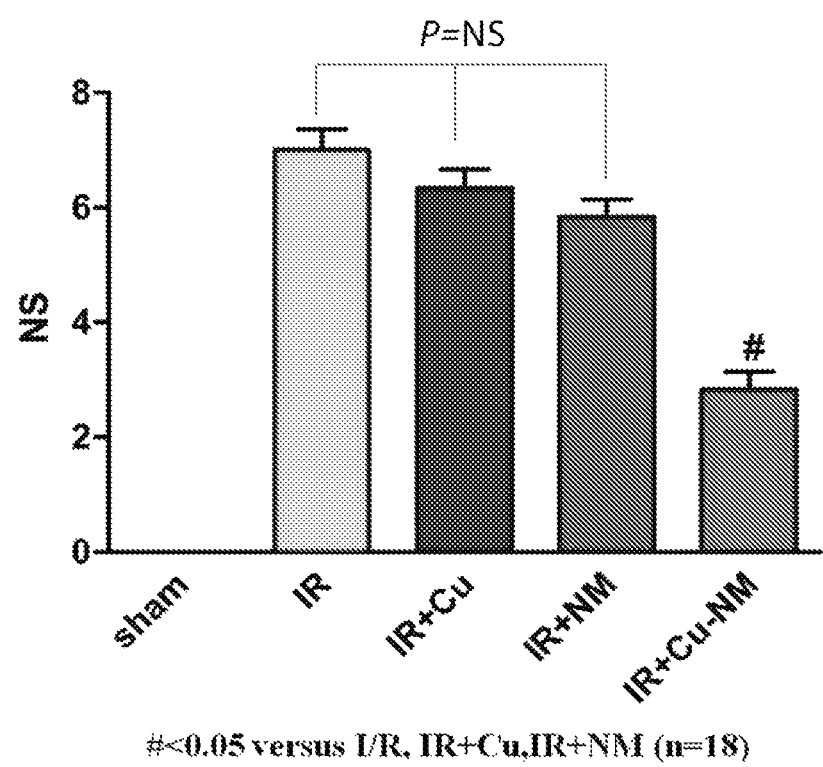
FIG. 35 shows quantitative analysis of nerve function score in brain ischemia rats, 14 days after copper nanomaterials treatment.

In 14 days after cerebral ischemia, nerve function score showed that sham group was normal, control group (IR), IR+Cu, IR+NM, IR+Cu–NM all showed varying degrees of nerve function injury in 14 days (Table 5). But IR+Cu–NM group of nerve function score in 14 days was significantly lower than the IR group, the IR+Cu and IR+NM ($P<0.05$); there was no significant difference among (IR), IR+Cu, IR+NM group (FIG. 35).

TABLE 5

Neurological score of rats post-operation 14 day ($\bar{\chi} \pm s$)

| Groups | Sham | IR | IR + Cu | IR + NM | IR + Cu-NM |
|---|---|---|---|---|---|
| NS | 0 | 6.94 ± 0.73 | 6.56 ± 1.20 | 6.22 ± 1.17 | 2.72 ± 0.89# |

Figure 36:
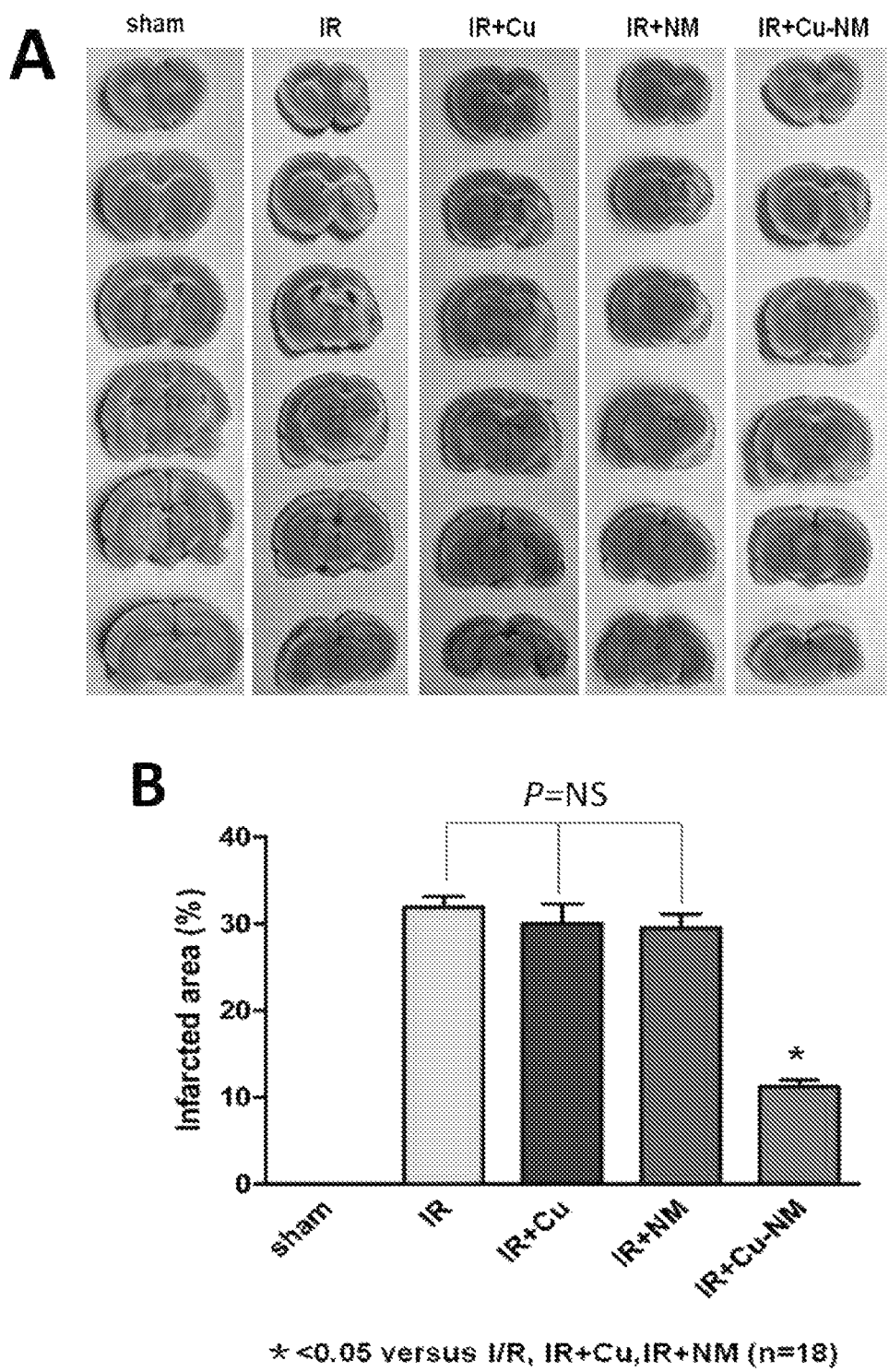
FIG. 36 shows TTC staining indicating changes in the size of cerebral infarction (FIG. 36A) and comparison of cerebral infarction size in different groups (FIG. 36B).

$P < 0.05$ versus IR, IR + Cu, IR + NM 2.3 Analysis of Cerebral Infarction Volume In 14 days after cerebral ischemia, TTC stain was performed to test the volume of cerebral infarction (FIG. 36A). Results showed that there was no infarction in the sham group, but IR+Cu, IR+NM, IR+Cu–NM all exhibited varying degrees of infarction (Table 6). The volume of cerebral infarction in IR+Cu–NM group was significantly lower than the IR group, the IR+Cu and IR+NM group($P<0.05$); There was no significant difference among (IR), IR+Cu, IR+NM group (FIG. 36B).

TABLE 6

Volume comparison of rats cerebral infarction ($\bar{\chi} \pm s$)

| Groups | Sham | IR | IR + Cu | IR + NM | IR + Cu-NM |
|---|---|---|---|---|---|
| Infarction volume(%) | 0 | 34.14 ± 3.99 | 30.16 ± 3.96 | 31.57 ± 3.52 | 10.81 ± 2.98 * |

* $P < 0.05$ versus IR, IR + Cu, IR + NM 2.4 Analysis of Brain Shrinkage Index

Figure 37:
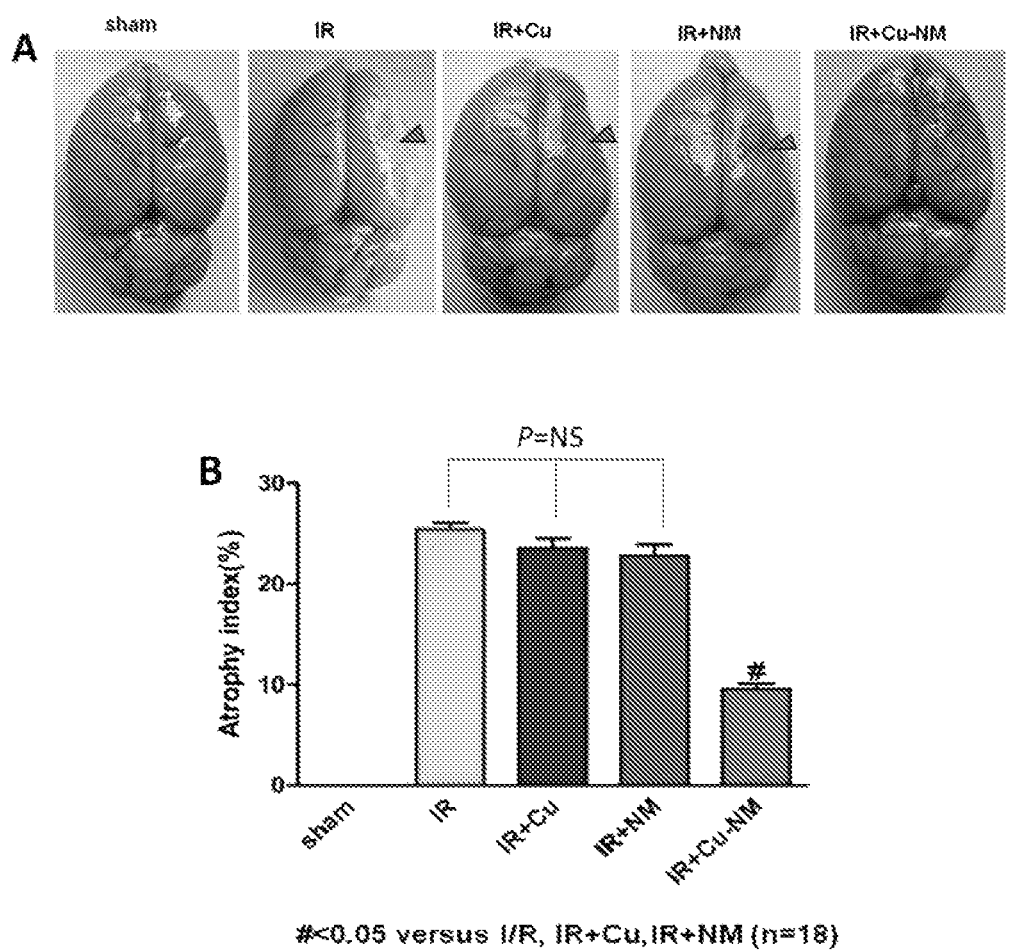
FIG. 37 shows the gross observation of whole brain and brain atrophy (FIG. 37A), and comparison of brain atrophy in brain ischemia rats of different group at 14th day after treatment (FIG. 37B).
Figure 38:
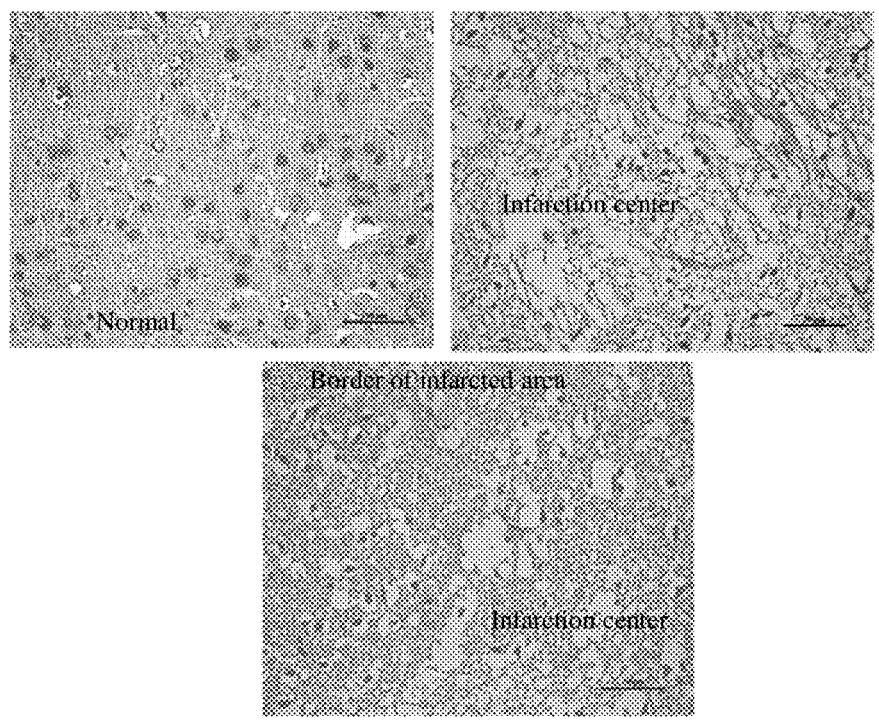
FIG. 38 shows haematoxylin and eosin staining in normal area, infarction center and border of infarcted area in brain.

After cerebral ischemia, local brain tissue underwent liquefactive necrosis and inflammatory cells infiltration, and necrotic tissue was absorbed gradually, finally ischemic brain atrophy occurred. The results showed that brain atrophy obviously in 14 days after cerebral infarction, brain shrinkage index (9.93±1.89%) in rats treated with the Cu–NM was significantly lower than the IR group (24.22±3.39), the IR+Cu+NM (22.18±2.93), IR group (22.11±3.52) (Table 7); And there were more capillaries in the brain tissue (FIG. 37). There is no significant difference among (IR), IR+Cu, IR+NM group. FIG. 37A shows that brain tissue shrinks obviously in 14 days after cerebral infarction. Brain in IR+Cu-NM group shrank slightly and appeared more visible capillaries. In FIG. 37B: quantitative comparison of brain atrophy shows that IR+Cu-NM group was significantly lower than the IR group, the IR+Cu, IR+NM group (P<0.05).

TABLE 7

Atrophy index of rat brain ($\bar{\chi} \pm s$)

| Groups | Sham | IR | IR + Cu | IR + NM | IR + Cu-NM |
|---|---|---|---|---|---|
| Atrophy index (%) | 0 | 24.22 ± 3.39 | 22.18 ± 2.93 | 22.11 + 3.52 | 9.93 + 1.89[#] |

[#]P < 0.05 versus IR, IR + Cu, IR + NM 2.5 The Change of Histopathologic Morphology After the Brain Cerebral Infarction Brain tissue was processed with HE staining and observed under microscopy: neuron number was large, the nucleus was obvious in normal brain tissues; Neurons was reduced significantly in the infarction area, cell arrangement was sparse and disordered, there was a wide range of cell necrosis, partial cell autolysis, fuzzy structure, disappeared nucleolus, more free bubble of nerve fibers around neurons in infarction area.

2.6 Detection of Angiogenesis

Figure 39:
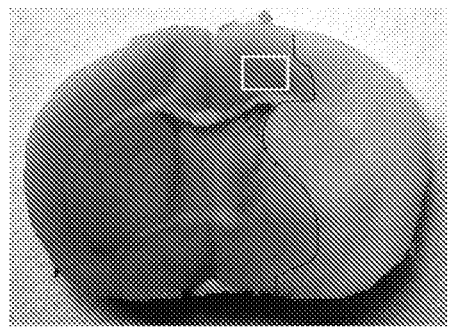
FIG. 39 shows angiogenesis detection area, the box showing border area of ischemia.
Figure 40:
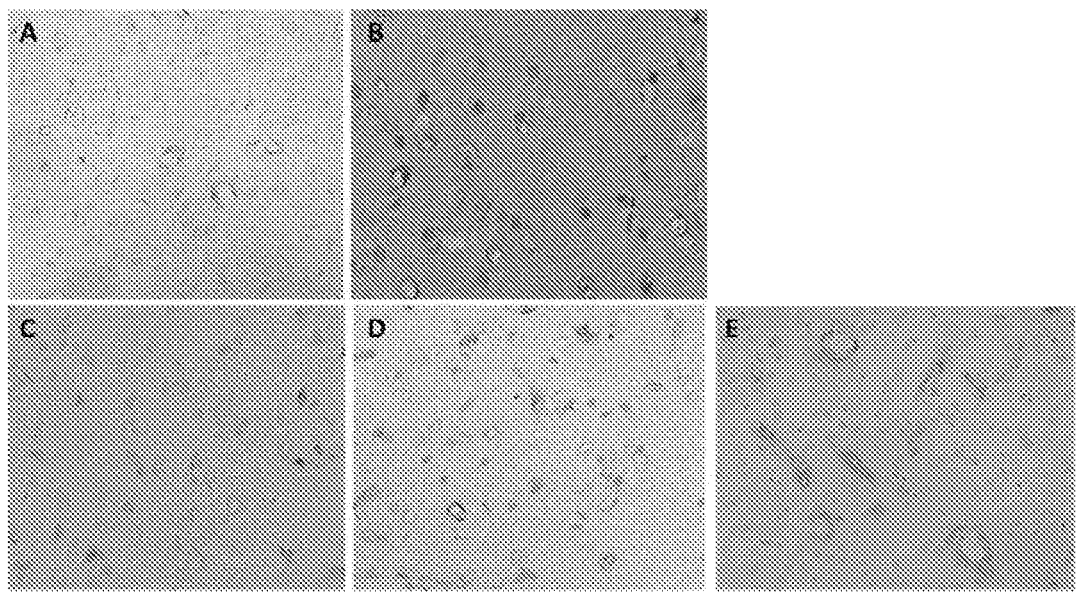
FIG. 40 shows immunohistochemical analysis showing CD31 labelled cells in border area of ischemia.

Angiogenesis was detected by immunohistochemical staining with vascular endothelial cell marker CD31 to observe the number of blood vessels. The surrounding area of cerebral ischemia (ischemic boundary zone, IBZ) was mainly observed. FIG. 39 showed angiogenesis detection area, as small box displayed IBZ. Then the number of vessels per square mm was calculated by vascular count. According to the results; there were a large number of new blood vessels around cerebral infarction in IR+Cu-NM group and blood vessels in this group were obviously more than other groups (FIG. 40).

Cerebral infarction was also called the ischemic cerebral apoplexy (cerebral ischemia, CI), it was result from the disorder blood supply to the brain caused by vascular stenosis or occlusion, leading the corresponding parts of brain tissue to ischemia, anoxia and necrosis, the soften disease, which accounts for about 80% of the total cerebral apoplexy. At present, super early thrombolysis treatment was the only effective treatment for CI, to restore blood flow of the ischemic tissues as soon as possible. However, therapy time window of thrombolysis had strict restrictions (<3 h). Thrombolysis therapy time window for some patients can be extended to 4.5 hours, but less than 5% of the thrombolysis patients can receive a safe and effective treatment. Thrombolysis treatment after the time window will lead to serious ischemia/reperfusion injury of ischemia/reperfusion (IR), increase the risk of hemorrhagic transformation, making the illness even worse. Now, even various kinds of neuroprotective drugs have been proved to be effective in animal models, but little effect on clinical application was confirmed.

Ischemic brain damage, as a tissue damage signal, initiated self tissue regeneration and repair mechanisms. But in the chronic phase of injury, lack of tissue injury signal caused the body's self repair and regeneration ability significantly decreasing or lost, the endogenous regeneration was limited to recover from injured brain function. So we activated the inherent tissue regeneration and repair system by exogenous intervention measures. The exogenous treatment activated inherent tissue regeneration ability and promoted nerve angiogenesis and regeneration. The combination of nerve and vascular regeneration promoted the recovery of neurological function.

Angiogenesis plays an important role in the recovery of neural function after cerebral ischemia. Newborn peripheral was mainly located in the infarction area, the ischemia and half dark band (ischemic penumbra, IP). Influenced by the collateral circulation, ischemia and half dark band isthmus provided certain compensatory blood flow. Ischemia half dark with death will occur within the cells without any treatment. Therefore, the exogenous intervention promoted angiogenesis in ischemic half dark belt, to save the damaged nerve cells by stimulating capillary growing around ischemia area and the formation of collateral circulation. Finally, the angiogenesis of ischemic area occurred, leading to the recovery of neural function.

Copper is an important part of regulating the activity of hypoxia inducing factor 1 (hypoxia-inducible factor 1, HIF-1). Copper can activate HIF-1 through the transcription complex HIF-1 and promote the expression of VEGF, angiopoietin-1 and other factors, so as to promote angiogenesis. Supplement of copper in the ischemic myocardial tissue can effectively restore the blood supply of the microcirculation, finally achieve the regeneration of myocardial tissue and restoration of neuron function.

Because excessive amounts of copper can cause oxidative stress, and produce serious side effects on the body, so copper controllable delivery system is an ideal tool for use of copper clinical. The ideal copper loader should be rich in copper and stay longer in the specific lesion site. Through the slow release of copper system, the inherent tissue regeneration was activated to promote the improvement of nerve function; and cupric should have good biocompatibility and no rejection. This example combined copper ions with nano materials (nanobiomaterial, NM) together. This new kind of copper nanomaterials (Cu-NM) had a very good biological compatibility, it can promote the effective absorption of copper through slow-release copper ions to ischemic areas, so as to promote angiogenesis in ischemia area and increase blood supply by improving the damaged brain tissue microcirculation, to repair the diseased tissue and restore damaged brain function.

This treatment was conducted by injecting copper nanometer materials into the cerebral ventricle rats in the 7th day after ischemia/reperfusion.

Both infarction volume and brain atrophy were decreased significantly in the 14 days. Nerve function was obviously improved. Cu-NM material promoted the cerebral infarction and peripheral vascular regeneration, which would be helpful to the recovery of neural function. On the 1st day after cerebral ischemic injury, cerebral infarction size and the nerve function score were the most serious, and then the infarction size was reduced gradually, rat dysfunction also gradually improved. Infarction size was little changed until to the 14th days. With the ischemic/reperfusion injury persisted, the inherent repair system was suppressed. However, this treatment activated the body's inherent repair mechanism to mobilize the stem cells which were recruited to the infarction area, and finally turned into mature cells and replaced the necrotic cells. This example provided strong evidence of the tissue inherent repair function motivated by copper supplement.

Copper controlled expression of various vascular growth factors such as VEGF by HIF-1 regulation. These factors were responsible for angiogenesis. The results displayed capillary density was increased significantly around the cerebral infarction area. VEGF alone can promote new blood vessel formation, but also require the participation of various factors to make the mature of blood vessels. Copper not only induced new blood vessels formation, but also promoted the mature of new blood vessels. These multiple effects were more effective than simple VEGF. This example showed that copper promoted the regeneration of the infarct peripheral vascular and improved the recovery of neural function.

This example showed that copper treatment obviously reduced brain atrophy. After cerebral infarction, neurons and glial cells necrosis and atrophy happened in infarction areas, but copper treatment could partly reverse brain atrophy. Research showed that the infarcted brain had an ability to regeneration after brain damage. In the central nervous system, the regeneration of nerve cells occurred in two specific areas: subependymal zone (subventricular zone, the SVZ) and hippocampal dentate gyrus of the grain area (subgranular zone, SGZ). Under physiological conditions, the nerve cells originated from the SVZ area and migrated along the rostral migration stream (the rostral migratory stream, RMS) to the olfactory bulb for supplement of the apoptosis of nerve cells. However, under the condition of cerebral ischemia, the nerve regeneration of SVZ area was increased significantly; the new nerve cells changed the traditional RMS migration pathways to the injury area, and enhanced the recovery of surrounding tissue. These studies showed the central nervous system responds to injury by nerve cell proliferation and cell homing to the lesion area. So the copper may be responsible for promoting nerve regeneration. Because the nerve regeneration relied on the base of vascular regeneration, and both effect promoted the recovery of neural function. Copper can promote the expression of various vascular growth factors, and these factors also have important role for nerve regeneration. In vivo and in vitro studies confirmed that VEGF increased the expression of cells proliferation marker BrdU in the mice cerebral ischemia SVZ areas, which indicated that VEGF acted as a role of nerve regeneration through several neurotrophic factors.

Example 4

Treatment of Rhesus Monkey Brain Infarction by Copper Material

This example used 9 Rhesus monkeys: 4 in untreated group and 5 in copper treatment group 1. The Establishment of Rhesus Monkey Brain Infarction Model Abrosia was carried out for 8 hours before surgery, and all subjects received an intramuscular injection of 10 mg/kg ketamine and 0.2 mg/kg midazolam to induce sedation. The animal was put on the surgery table after anesthesia. Hairs covering brain, limbs at electrode attachment sites and negative plate of the endotherm knife sites were shaved thoroughly for better ECG recording and operation. Vein gallery was established, and the monitor was connected after shaving the skin. Standard non-invasive measurement was performed during the surgery, including heart rate, blood pressure, oxygen saturation, partial pressure of carbon dioxide and temperature. Then subjects received an intramuscular injection of vecuronium bromide for the trachea cannula 3.5-4.5 tracheal catheter was inserted into the weasand under the help of laryngoscope. The location of the trachea cannula must be confirmed so that insuring it was in the trachea instead of in the esophagus. The parameter of the breathing machine was adjusted, adopting the pressure control model, P=12-20 mmHg, 40/min of breathing rate, 10-15 ml/kg of tidal volume, 30-40 mmHg of Carbon dioxide pressure. The anesthesia status was maintained by inhalation of the isoflurane (0%-1.5%), vein micro-injection of fentanyl (2 μg/kg), vecuronium bromide (0.05 mg/kg). with the satisfactory, animal was put on the operation table, fixing the head on the fixator with a 15° upward, to expose the right frontotemporal. The operation region was sterilized by the iodophor, laying the aseptic towel. Craniotomy of frontotemporal began with the right zygomatic arch, and ended at the media line.

Operation procedure contains cutting off the skin, subcutaneous tissue and temporalis, exposing the frontotemporal skull. Abrasive drilling drills frontotemporal skull to produce a tiny hole, and a 3×5 cm bone window was formed by rongeur. Cutting open the endocranium, fixed on the temporalis, to expose the temporal lobe. The brain tissue was covered by a cotton fleexe to reduce the injury of it. Bottom of the frontal lobe and the saddle area were exposed prudently by brain spatula. When the optic nerve could be seen, arachnoid should be separated by the detacher, releasing the cerebrospinal fluid, to reduce the pressure of the brain tissue. Once the brain tissue subsided, the frontal temporal lobe should be pushed aside by the self-motion retractor so as to expose the space of the operation. When the internal carotid is exposed from the near-end to the far-end, two branches of artery are seen at the crotch of the ICA, including the middle cerebral artery (MCA) and the anterior cerebral artery (ACA). Separating the MCA from the near-end to the far-end to expose the first section (M1 section) of it. Onset section of the MCA is ligatured by a 6-0 suture, and the M1 section, 5 mm length, was electricity-coagulated by the twin pole. Cutting off the electricity-coagulated section to block the blood circulation of the MCA. The operation region was cleaned by the normal saline, suturing the dura mater, muscle and the skin. Sterilizing the wound, a sterilized dressing was used to cover it.

Postoperative care contained maintaining the body temperature with electric blanket after anesthesia, keeping the respiratory tract unblocked, pulling out the tracheal catheter when the swallowing reflex restored. The animal was put back the breeding room until it could turn over or stand up. 100 mg tramadol was used to alleviate the pain by intramuscular injection, and 2 mg granisetron was used to prevent the nausea and vomiting by the same injection manner. Observing the animal 1-2 times per day post-operation made sure whether the syndrome or other abnormal on the region of the surgery have happened.

2. Nerve Function Score of Rhesus Monkey Brain Infarction Model

Nerve function score mainly adopted nonhuman primates Stroke rating Scale (Non-human Primate Stroke Scale, NHPSS) (Table 8) and the revised monkey brain stroke rating scale (Modified Neurological Scores Scale for Monkey Stroke, mNSS) (Table 9), for comprehensive evaluation of the rhesus monkeys cranial nerve function in many aspects, such as consciousness, muscle and nerve reflex, balance. The higher nerve function score represented the worse nerve function.

TABLE 8

Non-human Primate Stroke Scale, NHPSS

1. State of consciousness (0-2)
   0-normal
   1-drowsy of apathetic
   2-unconscious
2. Defence reaction (0-2)
   0-normal
   1-diminished
   2-none
3. Grasp reflex (right/left) (0-1X2): 0-present; 1-absent
4. Extremity movement (upper/lower, right/left) (0-4x4)
   0-normal
   1-asymmetrical use or strength noted
   2-clear, marked weakness
   3-minimal movement, profound weakness
   4-no voluntary use and no use in response to stimulation
5. Gait (0-3)
   0-normal; 1-limping
   2-severely impaired; 3-does not walk (but may crawl)
6. Circling (0-2)
   0-normal behavior
   1-noticeable preference to turn to one side
   2-constant rotation
7. Bradykinesia (0-2)
   0-none; 1-mild; 2-severe
8. Balance (0-2)
   0-normal
   1-mildly impaired
   2-profoundly impaired, unable to stand on feet
9. Neglect (right/left) (0-2x2)
   0-no neglect
   1-extinction of stimulus to one side when presented with simultaneous stimuli
   2-complete neglect of all stimuli, visual, auditory and tactile
10. Visual field cut/hemianopia (right/left) (0-1x2)
    0- none
    1- no response to visual stimuli in the affected field. Differentiated from neglect by the absence of blinking reflex (does not differentiate cortical lesion, but diagnoses optic or optic radiation injury as opposed to cortical problem.
11. Facial weakness (right/left) (0-2x2)
    0-no weakness
    1-mild
    2 -profound(if central $7^{th}$ -constant drooling, hanging angle of mouth

TABLE 9

Modified Neurological Scores Scale for Monkey Stroke, mNSS

| Category | Score |
|---|---|
| Consiousness (0-8) | |
| Normal, consistently alert and aggressive | 0 |
| Conscious and minimal aggressive | 1 |
| Conscious and evasive | 2 |
| Conscious but tolerant | 3 |
| Drowsiness, aroused with stimulation | 4 |
| Lethargia, eyes opened by intense stimulation | 5 |
| Stuporous , aroused with persistent stimulation | 6 |
| Light coma, reflex movement only | 7 |
| Deep coma, no movement | 8 |
| Motor system (ipsi-/contra-) (0-14x2) | |
| 1. Hand (motor power/movement, ipsi-/contra-) | |
| Normal | 0 |
| Asymmetry use-favors opposite extremity (able to grasp the cage bars with the affected hand) | 1 |
| Mild hemiparesis (able to raise the affected hand ) | 2 |
| Moderate hemiparesis (Clear, marked weakness, only able to support the body) | 3 |
| Severe hemiparesis (Minimal movement, profound weakness) | 4 |
| No voluntary use and no movement in response to stimulation | 5 |
| 2. Leg (motor power/movement, ipsi-/contra-) | |
| Normal | 0 |
| Minimal limping (able to walk and jump with the affected leg) | 1 |
| Mild hemiparesis (able to stand with the affected leg) | 2 |
| Moderate hemiparesis (raised with flexion of knee against gravity) | 3 |
| Severe hemiparesis (movement possible, but not against gravity) | 4 |
| Complete paralyzed and useless | 5 |

TABLE 9-continued

Modified Neurological Scores Scale for Monkey Stroke, mNSS

| Category | Score |
|---|---|
| 3. Facial weakness (motor power/movement, ipsi-/contra-) | |
|     Normal | 0 |
|     Mild weakness | 1 |
|     Profound weakness | 2 |
| 4. Grasp reflex (ipsi-/contra- 0-1 x2) | |
|     Present | 0 |
|     Diminished | 1 |
|     None | 2 |
| Sensory system (ipsi-/contra-) (0-4x2) | |
| 1. Facial sensation | |
|   React consistently to touch in any area of the face | 0 |
|   Absent, does not react to touch in any area of the face | 1 |
| 2. Pinna reflex | |
|     Twitch ear in response to outer/inner hair stimulation | 0 |
|     Absent, does not move ear r in response to touch | 1 |
| 3. Pain reflex | |
|     Strong, quick, complete withdrawal from toe pinch | 0 |
|     Weak, slow, incomplete or inconsistent withdrawal from toe pinch | 1 |
|     Absent, no withdrawal from toe pinch | 2 |
| Skeletamuscle coordination (0-6) | |
|     Normal, walks normally | 0 |
|       Minimal incoordination, walks with some gait impairment | 1 |
|     Uncoordinated, but able to climb a wire net | 2 |
|     Stands independently, falls within a few steps | 3 |
|     Sit only able to circle | 4 |
|       Posed with lateral or dorsal recumbency | 5 |
|       No movement | 6 |
| Visual field cut/hemianopia (ipsi-/contra-) (0-2x2) | |
|     Normal | 0 |
|     Hemianopic (blind in ½ of visual field) | 1 |
|     Complete blindness | 2 |
| Cheek pouch disorder (ipsi-/contra-) (0-3x2) | |
|     Absent | 0 |
|     Present | |
|       Small (5 cm) | 1 |
|       Moderate (5-10 cm) | 2 |
|       Large (>10 cm) | 3 |
| Total 60 scores | |

3. Neurological Score Results

Figure 41:
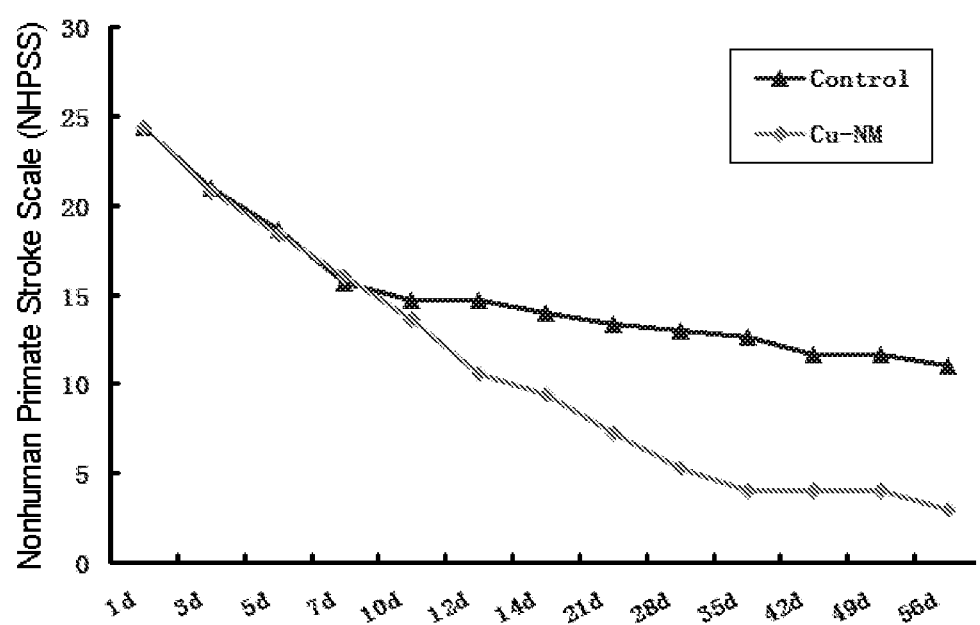
FIG. 41 shows quantitative analysis of nerve function injury score in cerebral infarction of Rhesus monkeys, showing nerve function improvement in 7 days after treatment in the copper compound treated group, compared to the untreated group.

Cerebral infarction has been formed in 7 days after cerebral ischemia, treated by injecting carrying copper nanomaterials, postoperative neurologic evaluation was performed. It was found that neural dysfunction in copper complex group was significantly reduced (P<0.05). Over time, neural functional recovery appeared more significant. The results showed that copper complexes can effectively promote neural functional recovery after the rhesus monkey brain infarction and improve nerve function (FIG. 41, the lower the score represented the lighter damage and the better nerve function). FIG. 41 is the evaluation of nerve dysfunction degree in the rhesus monkey brain infarction model. Compared with untreated group, results showed that treatment of copper complex improved nerve function significantly.

Example 5

Copper Promotion of Angiogenesis in Isolated Rat Aortic Ring

This example demonstrates that VEGF is essential for angiogenesis but the pro-angiogenesis effect of copper does not act through enhanced production of VEGF. Copper stimulation of angiogenesis at the organ system level is VEGF dependent, but copper stimulation of vascular endothelial cell proliferation in cultures is VEGF independent. In this example, isolated rat aortic rings were used. The thoracic aorta was isolated from Sprague Dawley rats (8-10 weeks) and sectioned into 1.0 mm thick vascular rings for culturing. Copper sulfide at a final concentration of 5, 25, 50 or 100 μM was added to the cultures and maintained for 8 days. A copper chelator, tetraethylenepentamine (TEPA) at a final concentration of 25 μM, was added to some cultures to block the effect of copper. An anti-VEGF antibody was used to determine the role of VEGF in copper promotion of angiogenesis. The data obtained showed that copper at 5 μM in cultures stimulated the vascular formation; an effect was blocked by TEPA. Copper at concentrations above 50 μM lost the pro-angiogenesis effect. However, copper at 5 μM did not enhance the production of VEGF, and concentrations above 50 μM significantly increased VEGF production. On the other hand, the treatment with anti-VEGF antibody completely blocked the pro-angiogenesis effect of 5 μM copper.

1. Methods 1.1 Isolated Rat Aortic Ring and Treatment Conditions

Thoracic aortas were removed from 8- to 10-week-old male Sprague Dawley (SD) rats (292-307 g) and immediately transferred to a culture dish containing ice-cold serum-free endothelial basal medium-2 (EBM-2, Lonza Cologne AG). The periaortic fibroadipose tissue was carefully removed with fine microdissecting forceps and iridectomy scissors; paying special attention not to damage the aortic wall. One-millimeter long aortic rings were sectioned and extensively rinsed in five consecutive washes with EBM-2.

1.2 Assay for Angiogenesis

Forty-eight well tissue culture grade plates were covered with 100 µl of matrigel (GFR, BD) and allowed to gel for 45 min at 37° C., 5% $CO_2$. Aortic rings were placed on the matrigel-coated wells, covered with an additional 100 µl matrigel and allowed to gel again for 45 min at 37° C., 5% $CO_2$. The culture was then added 250 µl EBM-2 containing 1% fetal bovine serum (FBS). Copper sulfide solution was added to the culture at a final concentration of 5, 25, 50 or 100 µM copper element. The growth media were removed and replaced every 2 days. Aortic rings were photographed on Day 8.

1.3 Image Analysis

The area of angiogenic sprouting was calculated using the Image J software program (NIH, Bethesda, Md.). Microvessel densities are reported in square pixels.

1.4 Western Blotting Analysis of VEGF

Protein extracts were obtained after lysing rat aortic rings with matrigel in the radio immunoprecipitation assay (RIPA) lysis buffer (Beyotime, Jiangsu, CN) containing 1% complete ethylene diamine tetraacetic acid (EDTA)-free protease inhibitor cocktail (Roche, Mannhein, DE) for 30 min on ice. Equal loading of protein was assured by prior quantitation using a bicinchoninic acid (BCA) protein assay kit (Thermo, Rockford, USA). An appropriate amount of protein in total lysates was resolved in a sodium dodecyl sulfate (SDS)-polyacrylamide electrophoresis gel and transferred onto a polyvinylidene difluoride membrane (Bio-rad, USA). Membranes were blocked for 1 h in Tris-buffered saline/Tween 20 (TBST) (10 mM Tris.HCl, pH 8.0, 150 mM NaCl and 0.1% Tween 20) containing 5% nonfat dry milk and incubated overnight at 4° C. with the primary mouse anti-VEGF antibody (Santa Cruz, Calif., USA) and mouse antibeta actin antibody (ZSGB-BIO, Beijing, CN) diluted in the blocking buffer. After washing with TBST, the membranes were incubated with a horseradish peroxidase (HRP)-linked anti-mouse immunoglobulin G (IgG) antibody (ZSGB-BIO, Beijing, CN) diluted in TBST for 1 h at room temperature. Target proteins were visualized using a chemiluminescence HRP substrate (Millipore, Billerica, USA).

1.5 Neutralization of VEGF

Aortic rings were cultured in 48-well plates in 250 µl EBM-2 (1% FBS) media containing anti-VEGF antibody (Santa Cruz, Calif., USA) at a final concentration of 2 ng/ml. The treatment and angiogenesis assay were the same as above.

1.6 Statistical Analysis

Data were obtained from three independent experiments and expressed as means±S.E.M. The results presented in FIG. 42 and FIG. 44A were initially analyzed by one-way analysis of variance and further analyzed by Dunnett's T3 test for comparison among multiple groups. A 2×2 factorial design was applied to the data presented in FIG. 43 and FIG. 44B and FIG. 45. After a significant interaction was detected, the significance of the main effects was further determined. The level of significance was considered at P<0.05.

2. Results

2.1 The Effect of Copper on Angiogenesis of the Isolated Rat Aortic Ring

Figure 42:
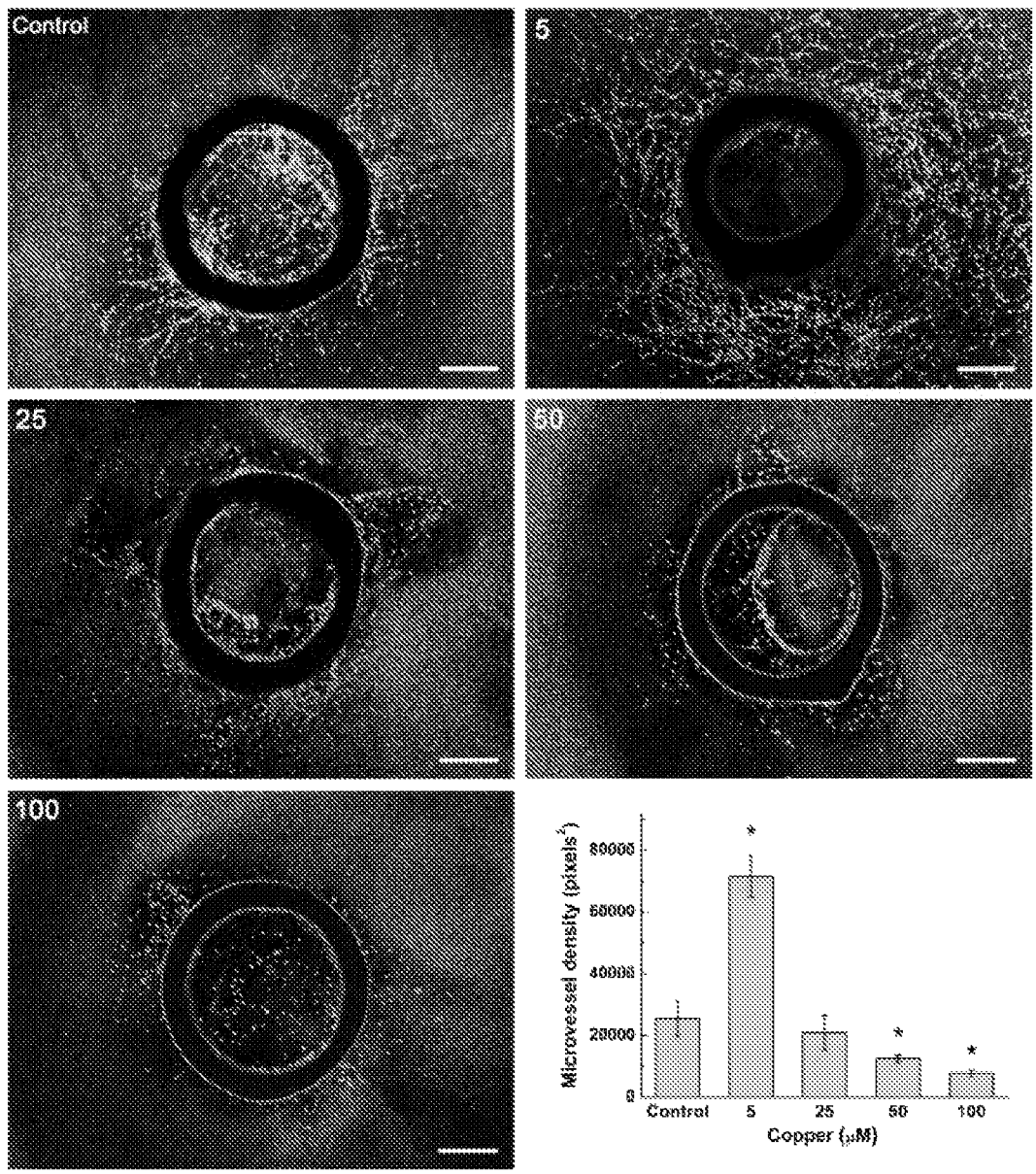
FIG. 42 shows effects of varying concentrations of copper sulfide on angiogenesis of the isolated rat aortic rings cultured in EBM-2 with 1% FBS.

FIG. 42 shows effects of varying concentrations of copper sulfide on angiogenesis of the isolated rat aortic rings cultured in EBM-2 with 1% FBS. Copper sulfide was added directly to the cultures at the final concentration of copper element of 0 (control), 5, 25, 50 or 100 µM and maintained for 8 days. The quantitative data were obtained from three separate experiments; each containing three samples for each treatment, and the data presented as mean±S.E.M.; *significantly different from the control group (P<0.05) (bar=500 µm).

It was observed that copper at 5 µM had the strongest promotion effect on the angiogenesis. Concentrations above this level not only did not show pro-angiogenesis effect but also displayed significantly inhibitory effect at concentrations above 50 µM. The final concentrations of copper, including contributions of media, FBS (1%), and added copper were 26.9, 344.4, 1614.4, 3201.9 or 6416.9 µg/L in cultures added 0, 5, 25, 50, or 100 µM copper, respectively. Consequently, copper concentrations in aortic rings after culturing for 8 days in varying concentrations of added copper were respectively 5.9, 26, 63, 106, or 162 µg/g tissue, which was proportional to copper concentrations in cultures.

Figure 43:
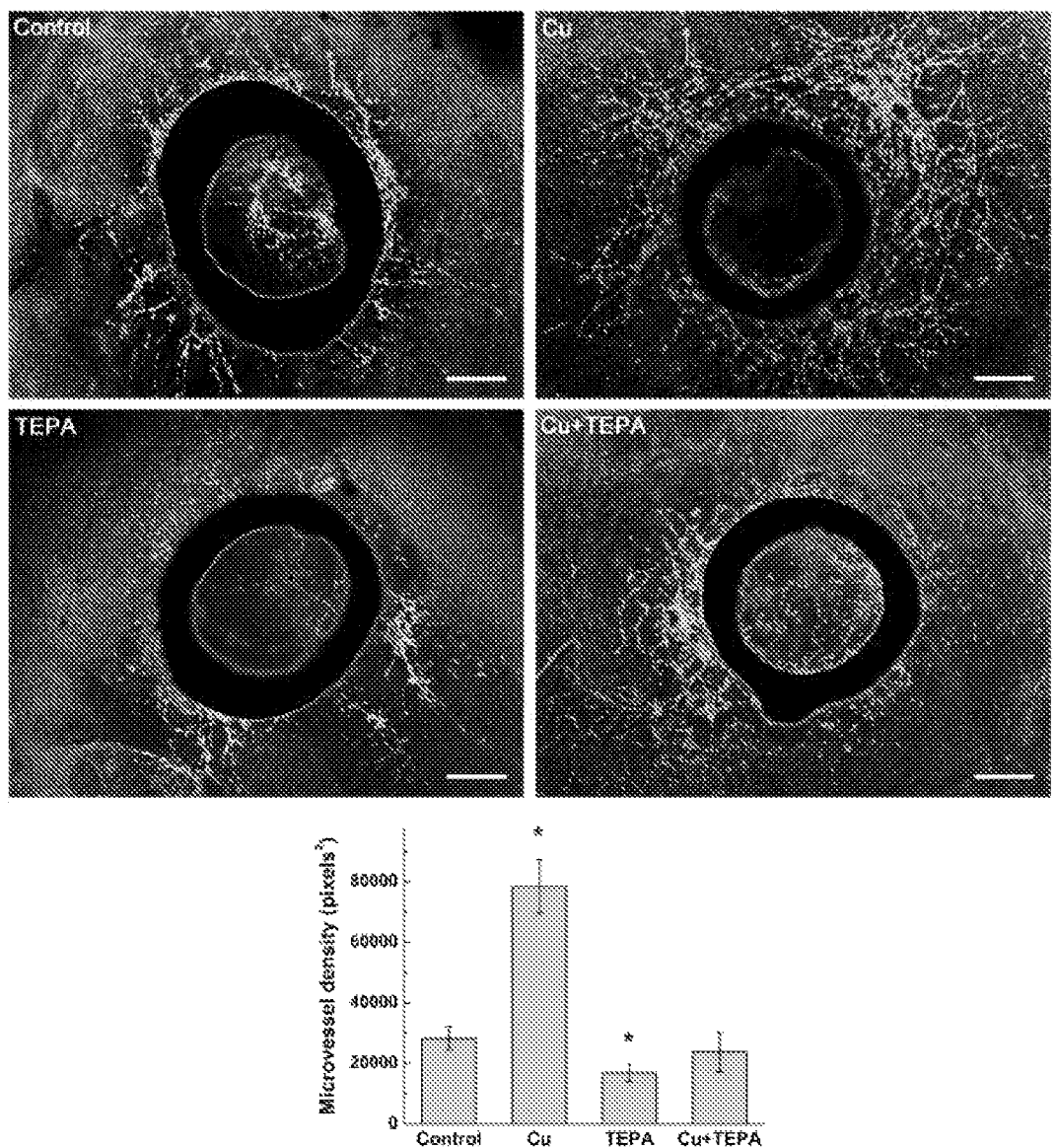
FIG. 43 shows the effect of copper chelator TEPA on copper promotion of angiogenesis.

A copper chelator, tetraethylenepentamine (TEPA), was added alone as control or simultaneously with copper at a final concentration of 25 µM to the culture for 8 days. By this treatment, TEPA itself caused an inhibition of angiogenesis and completely suppressed the angiogenic promotion effect of 5 µM copper, as shown in FIG. 43. The isolated rat aortic rings cultured in EBM-2 with 1% FBS were treated with 5 µM copper sulfide, 25 µM TEPA or both for 8 days. The quantitative data were obtained from three separate experiments; each containing three samples for each treatment, and the data presented as mean±S.E.M.; *significantly different from the control group (P<0.05) (bar=500 µm).

Figure 44:
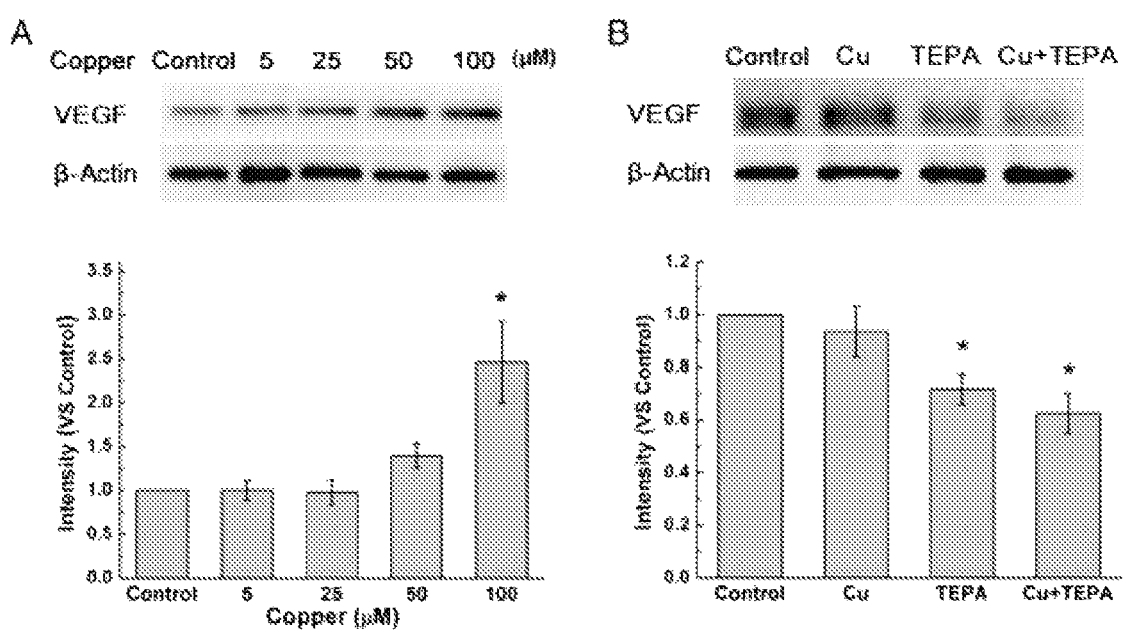
FIG. 44 shows Western blot analysis of VEGF protein levels in the isolated rat aortic rings.

2.2 The Effect of Copper on the Production of VEGF in the Isolated Aortic Ring The results presented in FIG. 44 show that, at 5 µM in the culture, copper did not enhance the production of VEGF in the isolated vascular tissue, but at the concentrations above 50 µM, which caused a suppression of angiogenesis, copper significantly increased the production of VEGF. TEPA at a final concentration of 25 µM significantly decreased VEGF levels in the isolated rat aortic ring tissue treated with or without 5 µM copper in cultures (FIG. 44). FIG. 44 shows Western blot analysis of VEGF protein levels in the isolated rat aortic rings. FIG. 44A shows effects of varying concentrations of copper on VEGF protein levels. The treatment protocol was the same as presented in FIG. 42. FIG. 44B shows effect of TEPA on VEGF protein levels. The treatment protocol was the same as presented in FIG. 43. All of the quantitative data were obtained from three independent experiments and presented as mean±S.E.M.;*significantly different from the control group (P<0.05).

2.3 The Effect of Anti-VEGF Antibody on Copper Promotion of Angiogenesis

Figure 45:
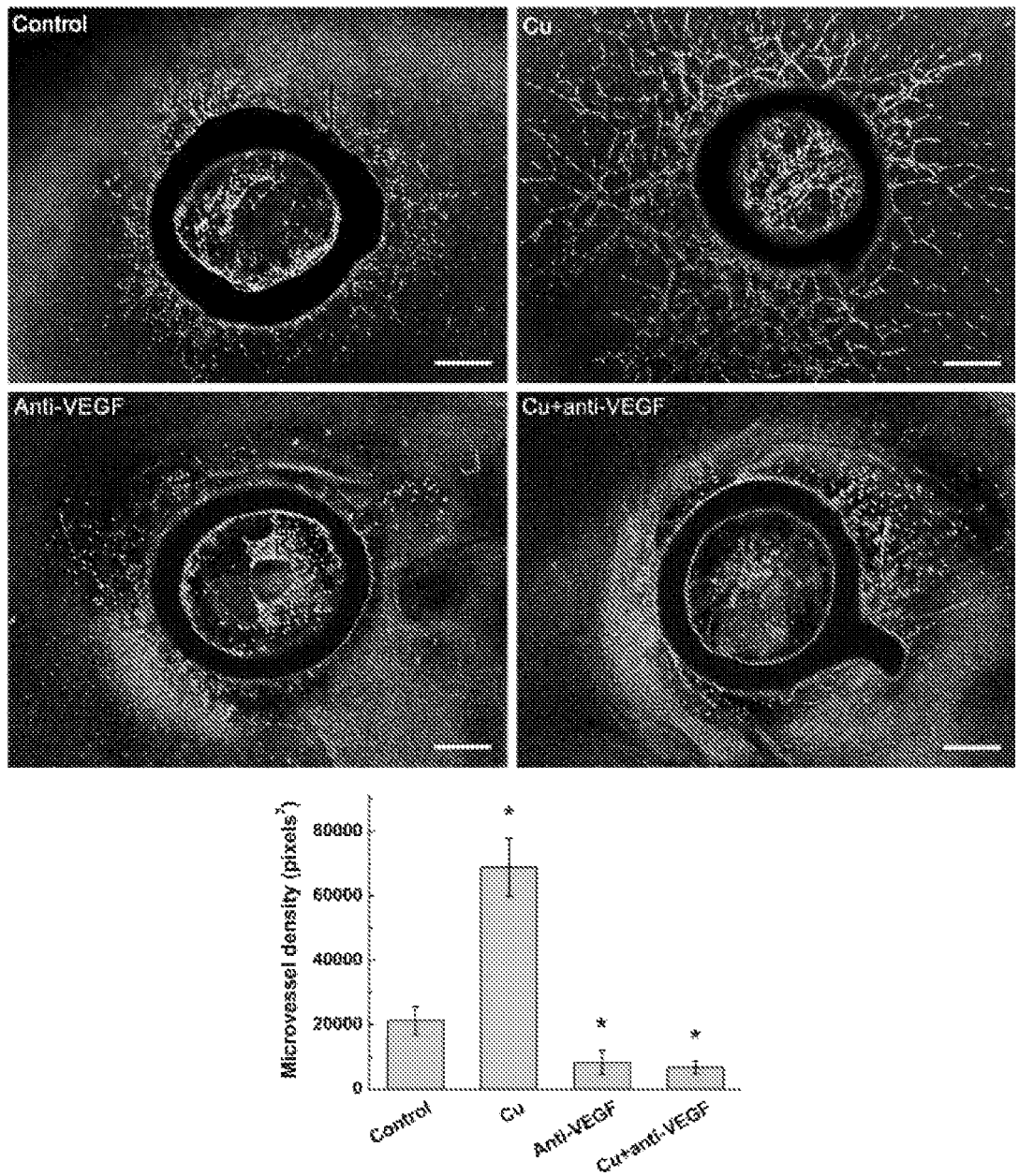
FIG. 45 shows the effect of anti-VEGF antibody on copper promotion of angiogenesis.

The results presented in FIG. 45 show that a final concentration of 2-ng/ml anti-VEGF antibody in the culture alone significantly suppressed angiogenesis and its combination with 5 µM copper completely blocked the angiogenic promotion effect of copper. FIG. 45 shows effect of anti-VEGF antibody on copper promotion of angiogenesis. The isolated rat aortic rings cultured in EBM-2 with 1% FBS were treated with 5 µM copper sulfide, 2 ng/ml anti-VEGF antibody or both for 8 days. The quantitative data were obtained from three independent experiments and presented as mean ±S.E.M.; *significantly different from the control group (P<0.05) (bar=500 µm).

Figure 46:
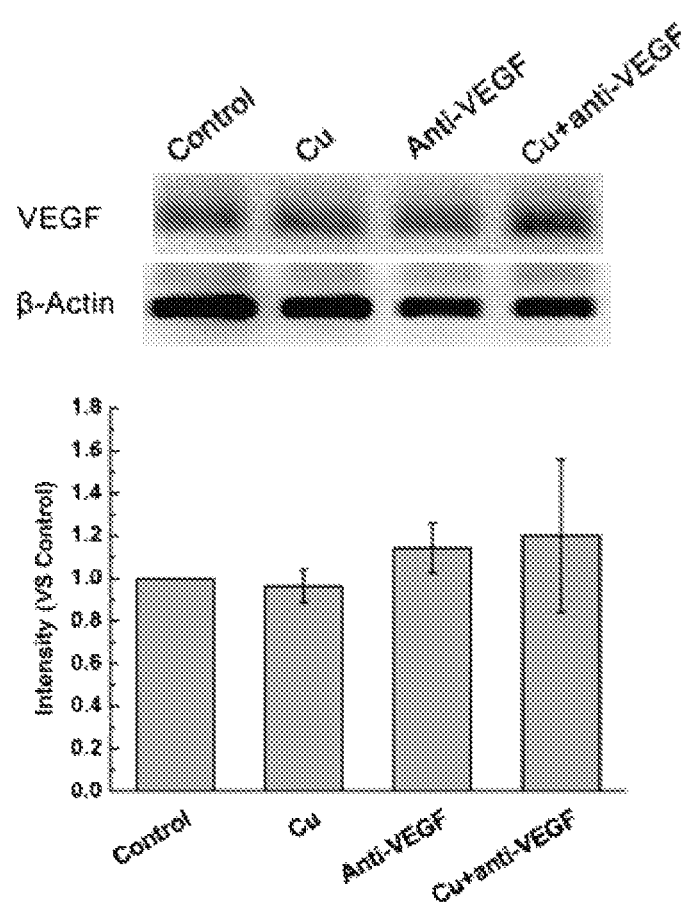
FIG. 46 shows the effect of anti-VEGF antibody on VEGF protein levels in isolated rat aortic rings.

However, either anti-VEGF antibody alone or its combination with 5 µM copper did not affect the production of VEGF (FIG. 46). FIG. 46 shows the effect of anti-VEGF antibody on VEGF protein levels in isolated rat aortic rings. The same treatment protocol described for FIG. 45 was applied. All of the quantitative data were obtained from three

Example 6

Zinc Supplementation Treatment for Liver Injury

Hepatic stellate cells secreted a large amount of collagen after persist stimulus of alcohol, virus and chemical substance. Liver fibrosis and damage was happened due to the excessive deposition of extracellular matrix. Due to the specific function of zinc to reverse fibrosis, this example utilizes the targeted zinc supplement therapy to activate the hepatic tissue inherent self-repair, mobilize stem cells (e.g. bone marrow mesenchymal stem cells) homing to the injury site of liver, differentiate to hepatic cells, and regenerate injury tissue. The targeted zinc supplement is achieved by ultrasound mediated zinc loaded microbubble explosion to delivery zinc to injured hepatic tissue. After targeted zinc supplement treatment, liver fibrosis is reversed, liver function is recovered.

This experiment was conduct to evaluate the therapeutic effect of ultrasound medicated zinc loaded microbubble explosion on liver fibrosis and fatty liver disease. Wister rat model of liver fibrosis was induced by injection of thiacetamide (TAA) 100 mg/kg on alternative days until the occurrence of liver fibrosis symptom. Then the models were divided into two groups, treated group and untreated group. In the treated group, the ultrasound medicated zinc loaded microbubble explosion treatment was conduct in every three days. After treatment, blood sample was collected for liver injury related markers, blood fat, hepatic lipid, collagen, activity of antioxidant enzymes and lipid over-oxidation metabolites examination. Liver injury state was judged according to the alanine aminotransferase (ALT) and aspartate transaminase (AST) detection. TNF-α and IL-β are secreted after liver injury, which in turn accelerate the liver damage. Thus, the levels of TNF-α and IL-β are indicators to assess the degree of liver injury. In addition, the reverse of liver fibrosis can also be evaluated by hepatic tissue slice and biopsy.

This experiment is conduct to evaluate the therapeutic effect of ultrasound medicated zinc loaded microbubble explosion on chemical liver injury. Sprague-Dawley rat model of liver injury is induced by intubation feeding of tetrachloride carbon (CCL4) 1 mL/kg (40%) on alternative days until the occurrence of liver injury symptom. Then the models are divided into two groups, treated group and untreated group. In the treated group, the ultrasound medicated zinc loaded microbubble explosion treatment is conduct in every three days. After treatment, blood sample is collected for liver injury related markers, blood fat, hepatic lipid, collagen, activity of antioxidant enzymes and lipid over-oxidation metabolites examination. Liver injury state is judged according to the alanine aminotransferase (ALT) and aspartate transaminase (AST) detection. TNF-α and IL-β are secreted after liver injury, which in turn accelerate the liver damage. Thus, the levels of TNF-α and IL-β are indicators to assess the degree of liver injury. In addition, the reverse of liver fibrosis can also be evaluated by hepatic tissue slice and biopsy.

Example 7

Targeted Replenishment of Cardiac Copper Content Using Ultrasound-Mediated Copper-Albumin Microbubble 1. Methods.

1.1 Copper Ultrasound Microbubble Treatment

An ultrasound-guided therapy of myocardial infarction was performed in normal mice. The copper microbubbles were infused via the tail vein. During each copper microbubble treatment, the ultrasound probe (Vivid 7, i13L, GE Healthcare Ultrasound) was placed on the precordium of the chest, so that the ultrasound wave could be directed to the infarction area of heart. The mechanical index was set to 1.2. After each injection, the copper microbubbles which arrived at the ventricles through the circulation system were exploded by triggering the ultrasound power. At the same time, the ultrasound probe was moved slightly back and forth along the short axis between the apex and the mitral valve of the heart. After copper microbubbles of each injection were blown up, next infusion was followed until the dose of each treatment (0.5 mg/kg) was completely administered. After injection, blood sample was collected and heart was harvested.

1.2. Cu Concentration Determination.

Samples were freshly frozen and stored at −80° C. before lyophilization. After lyophilization and digestion of the tissues with nitric acid, digests were colorless or light yellow and clear with no visible precipitate or residue. Ultrapure water was added to each vessel to dilute $HNO_3$ to 2% for subsequent analyses of copper. Copper concentrations were determined by graphite furnace atomic absorption spectrophotometry (ICE3500, Thermo) using the program shown in Table 10.

TABLE 10

| Graphite furnace atomic absorption spectrophotometry program | | |
|---|---|---|
| Temperature (° C.) | Time (s) | Argon Gas Flow(L/min) |
| 90 | 20 | 0.2 |
| 120 | 20 | 0.2 |
| 850 | 20 | 0.2 |
| 2100 | 3 | 0 |
| 2500 | 3 | 0.2 |

2. Results

Figure 47:
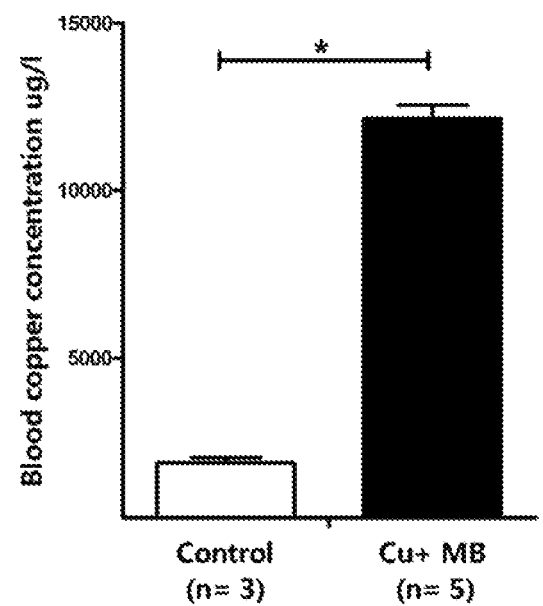
FIG. 47 shows significant increase in the blood copper concentration after injection of copper microbubbles.
Figure 48:
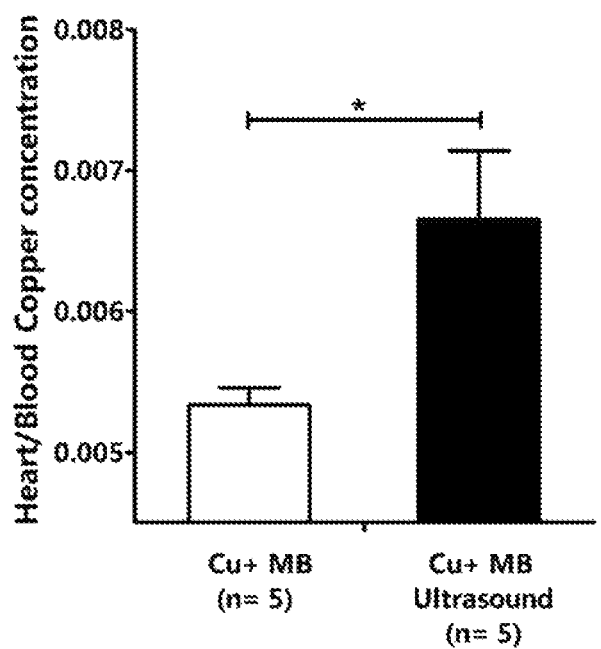
FIG. 48 shows significant increase in the ratio of heart copper concentration to blood copper concentration in ultrasound mediated copper microbubble treatment group as compared to the group treated with copper microbubbles without ultrasound.

After injection of the copper microbubbles, the blood copper concentration was increased significantly (FIG. 47). In addition, as the ultrasound probe released power, the copper microbubbles were exploded. Sonoporation induced by the ultrasound further led to formation of transient holes in the cell membrane and capillaries, which greatly facilitated the uptake of copper into the heart tissue in the ultrasound-mediated copper microbubble treatment group (Cu+MB ultrasound), as compared to the treatment group with the copper microbubbles without ultrasound mediation (Cu+MB) (FIG. 48).

---

What is claimed is:

1. A method of inducing at least two events of tissue repair in an individual having a tissue injury, comprising delivering to the site of injury an effective amount of copper, wherein the tissue is heart, liver or brain, wherein the at least two events of the tissue repair comprises inducing the migration of bone marrow mesenchymal stem cells to the site of injury, and at least one of:
   (i) inducing differentiation of stem cells at the site of injury;
   (ii) inducing tissue regeneration at the site of injury;
   (iii) inducing a signaling molecule that triggers tissue regeneration; and
   (iv) reconstruction of the microenvironment of neurofibril cells and neurosecretory cells at the site of injury.

2. The method of claim 1, wherein the tissue injury is an ischemic tissue injury.

3. The method of claim 1, further comprising administering to the individual an effective amount of stem cells.

4. The method of claim 1, further comprising delivering to the site of injury an effective amount of an inducer of stem cells.

5. The method of claim 1, wherein the individual has a compromised tissue repair system.

6. The method of claim 5, wherein the individual having a compromised tissue repair system is an individual having a chronic tissue injury.

7. The method of claim 5, wherein the individual having a compromised tissue repair system is an individual who is at least 60 years old.

8. The method of claim 5, wherein the individual having a compromised tissue repair system is an individual who is deficient in stem cells.

9. The method of claim 1, wherein copper is delivered via a microbubble.

10. The method of claim 9, wherein the microbubble comprising copper is administered intravenously, and copper is released through site-directed bursting of the microbubble at the site of the injury.

11. The method of claim 10, wherein the site-directed bursting of the microbubble is by ultrasound.

12. The method of claim 1, wherein copper is delivered by directly administering copper to the site of the injury.

13. The method of claim 1, wherein copper is delivered via injection and stays concentrated at the injection site upon injection.

14. The method of claim 1, wherein copper is delivered via an implant containing copper.

15. The method of claim 14, wherein the implant is coated with copper.

16. The method of claim 1, wherein the tissue injury is a chronic tissue injury.

17. The method of claim 16, wherein the tissue injury is an ischemic chronic tissue injury.

18. The method of claim 17, wherein the tissue is heart.

19. The method of claim 18, wherein copper is delivered via a microbubble.

20. The method of claim 19, wherein the individual has a myocardial infarction.

21. The method of claim 17, wherein the tissue is brain.

22. The method of claim 21, wherein the individual has a cerebral infarction.

* * * * *

SEQUENCE LISTING

<160> NUMBER OF SEQ ID NOS: 8

<210> SEQ ID NO 1
<211> LENGTH: 22

```
<212> TYPE: DNA
<213> ORGANISM: Artificial Sequence
<220> FEATURE:
<223> OTHER INFORMATION: Synthetic Construct

<400> SEQUENCE: 1
gtctgcaaca tggaaggtat tg                                             22

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
gcaggtcata ggtggtttct                                                20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
gagcttccta cagcacaaca                                                20

<210> SEQ ID NO 4
<211> LENGTH: 22
<212> TYPE: DNA
<213> ORGANISM: Artificial Sequence
<220> FEATURE:
<223> OTHER INFORMATION: Synthetic Construct

<400> SEQUENCE: 4
ccaggactta taccgggatt tc                                             22

<210> SEQ ID NO 5
<211> LENGTH: 22
<212> TYPE: DNA
<213> ORGANISM: Artificial Sequence
<220> FEATURE:
<223> OTHER INFORMATION: Synthetic Construct

<400> SEQUENCE: 5
gggtcacatc acctaacatc ac                                             22

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct

<400> SEQUENCE: 6
cctttctgct gtcccagatt ac                                             22

<210> SEQ ID NO 7
<211> LENGTH: 22
<212> TYPE: DNA
<213> ORGANISM: Artificial Sequence
<220> FEATURE:
<223> OTHER INFORMATION: Synthetic Construct

<400> SEQUENCE: 7
```

```
ccacgaaact accttcaact cc                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic Construct

<400> SEQUENCE: 8
gtgatctcct tctgcatcct gt                                              22
```